United States Patent
Kasturi et al.

(10) Patent No.: US 6,827,795 B1
(45) Date of Patent: Dec. 7, 2004

(54) DETERGENT COMPOSITION COMPRISING POLYMERIC SUDS ENHANCERS WHICH HAVE IMPROVED MILDNESS AND SKIN FEEL

(75) Inventors: Chandrika Kasturi, Cincinnati, OH (US); Michael Gayle Schafer, Alexandria, KY (US); Marsha Jean Spears, Ft. Thomas, KY (US); Howard David Hutton, III, Oregonia, OH (US); Mark Robert Sivik, Ft. Mitchell, KY (US); Bernard William Kluesener, Harrison, OH (US); William Michael Scheper, Lawrenceburg, IN (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/979,562
(22) PCT Filed: May 25, 2000
(86) PCT No.: PCT/US00/14405

§ 371 (c)(1),
(2), (4) Date: Nov. 14, 2001

(87) PCT Pub. No.: WO00/71658

PCT Pub. Date: Nov. 30, 2000

Related U.S. Application Data

(60) Provisional application No. 60/135,888, filed on May 26, 1999.

(51) Int. Cl.$^7$ .............................. C11D 3/30; C11D 3/37; A61K 7/48
(52) U.S. Cl. .......................... 134/42; 134/39; 510/130; 510/138; 510/159; 510/427; 510/433; 510/434; 510/476; 510/477; 424/70.11; 424/70.14; 424/70.16; 424/70.21

(58) Field of Search .................... 510/130, 138, 510/159, 427, 433, 434, 476, 477; 134/39, 42; 424/70.11, 70.14, 70.16, 70.21

(56) References Cited

U.S. PATENT DOCUMENTS

| 4,784,789 A | * | 11/1988 | Jeschke et al. ......... 252/174.23 |
| 6,207,631 B1 | * | 3/2001 | Kasturi et al. .............. 510/237 |
| 6,277,811 B1 | * | 8/2001 | Kasturi et al. .............. 510/475 |
| 6,369,012 B1 | * | 4/2002 | Kasturi et al. .............. 510/237 |
| 6,372,708 B1 | * | 4/2002 | Kasturi et al. .............. 510/475 |
| 6,521,577 B1 | * | 2/2003 | Clarke et al. ............... 510/237 |
| 6,528,476 B1 | * | 3/2003 | Bodet et al. ................ 510/476 |
| 6,528,477 B2 | * | 3/2003 | Kasturi et al. .............. 510/476 |
| 6,573,234 B1 | * | 6/2003 | Sivik et al. ................. 510/475 |
| 6,589,926 B1 | * | 7/2003 | Vinson et al. .............. 510/237 |

FOREIGN PATENT DOCUMENTS

| DE | 195 45 630 A1 | 6/1997 | |
| EP | 0 0 13 585 A1 | 7/1980 | |
| EP | 013585 | * 7/1980 | ............ C11D/3/37 |
| EP | 0 308 190 A2 | 3/1989 | |
| EP | 308190 | * 3/1989 | ............ A61K/7/50 |
| GB | 1 584 127 | 2/1981 | |
| JP | 11217588 | 10/1999 | |
| WO | WO 99/27053 | 6/1999 | |
| WO | WO 99/27054 | 6/1999 | |
| WO | WO 99/27058 | 6/1999 | |

* cited by examiner

Primary Examiner—Brian P Mruk
(74) Attorney, Agent, or Firm—Caroline Wei-Berk; C. Brant Cook; Kim W. Zerby

(57) ABSTRACT

Method of improving the skin feel or mildness to the skin of various detergent compositions, such as hand dish washing compositions, hand laundry bars, shampoos and other personal cleansing compositions.

29 Claims, No Drawings

DETERGENT COMPOSITION COMPRISING POLYMERIC SUDS ENHANCERS WHICH HAVE IMPROVED MILDNESS AND SKIN FEEL

This application claims the benefit of Provisional application Ser. No. 60/135,888 filed May 26, 1999.

FIELD OF THE INVENTION

The present invention relates to compositions comprising one or more polymeric suds volume and suds duration enhances which are mild on the users skin. The polymeric suds enhances are suitable for use in methods which in use as compositions light duty liquid, LDL compositions, hand dishwashing compositions, laundry bars, personal cleansing compositions and the like.

BACKGROUND OF THE INVENTION

In formulating detergent compositions which will foreseeable contact the users skin, such as Light-duty liquid or gel dishwashing detergent compositions laundry bars, personal cleansing compositions (such as shampoos and body washes) and the like the problem of mildness is of major concern. Furthermore, the formulator must also produce a composition which provides adequate cleaning for the desired end use. However, it is well know that the best cleaning surfactants, such as the anionic surfactants, for example LAS, AS etc., irritate the users skin. The alternative has been to use surfactants which do not irritate the users skin, however these are typically not the bets cleaning surfactants available. The formulator is presented with the difficult task of resolving these two seemingly conflicting, properties.

Consequently, their remains the need for a detergent composition which can have the best possible cleaning while being mild enough for prolonged contact with users skin.

SUMMARY OF THE INVENTION

It has now en found that the suds boosting polymers described herein when added to a added to a detergent composition improves the mildness of the composition, even those compositions containing harsh surfactants, and surprisingly improves skin mildness.

The present invention meets the aforementioned needs in that it has been surprisingly discovered that certain polymers serve not only as suds duration and suds volume extenders, but also enhance the mildness of a detergent composition. The effective polymers of the present invention provide both increased suds volume and suds duration when formulated in a detergent composition.

A first aspect of the present invention relates to a method for manually cleaning an object, preferably tableware, such as plates, glasses, flatware etc., fabrics, such as clothing, bed linen, carpets, etc., skin or hair, comprising contacting a user's hands with a washing solution comprising water and a detergent composition in which suds produced by the solution is maintained for an extended period of time by a polymeric suds stabilizer, said suds stabilizer is selected from the group consisting of:

(a) polymers comprising at least one monomeric unit of the formula:

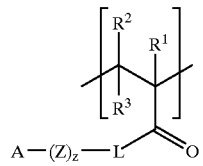

wherein each of $R^1$, $R^2$ and $R^3$ are independently selected from the group consisting of hydrogen, $C_1$ to $C_6$ alkyl, and mixtures thereof; L is selected from the group consisting of a bond, O, $NR^6$, $SR^7R^8$ and mixtures thereof, wherein $R^6$ is selected from the group consisting of hydrogen, $C_1$ to $C_8$ alkyl and mixtures thereof; each of $R^7$ and $R^8$ are independently hydrogen, O, $C_1$ to $C_8$ alkyl and mixtures thereof, or $SR^7R^8$ form a heterocyclic ring containing from 4 to 7 carbon atoms, optionally containing additional hetero atoms and optionally substituted; Z is selected from the group consisting of: —$(CH_2)$—, $(CH_2—CH=CH)$—, —$(CH_2—CHOH)$—, $(CH_2—CHNR^6)$—, —$(CH_2—CHR^{14}—O)$— and mixtures thereof; wherein $R^{14}$ is selected from the group consisting of hydrogen, $C_1$ to $C_6$ alkyl and mixtures thereof; z is an integer selected from about 0 to about 12; A is $NR^4R^5$, wherein each of $R^4$ and $R^5$ are independently selected from the group consisting of hydrogen, $C_1$ to $C_8$ alkyl, and mixtures thereof, or $NR^4R^5$ form an heterocyclic ring containing from 4 to 7 carbon atoms, optionally containing additional hetero atoms, optionally fused to a benzene ring, and optionally substituted by $C_1$ to $C_8$ hydrocarbyl; and wherein said polymeric suds stabilizer has a molecular weight of from about 1,000 to about 2,000,000 daltons;

(b) a proteinaceous suds stabilizer, said proteinaceous suds stabilizer having an isoelectric point of from about 7 to about 11.5; and (c) a zwitterionic polymeric suds stabilizer;

wherein said method further including the step of washing the object with said solution; and wherein said suds stabilizer is a, mild, suds enhancing, suds stabilizer such that a user's hands, after submersion in a solution containing said suds stabilizer, are not irritated.

A second aspect of the present invention relates to a method of enhancing mildness of a detergent composition comprising a surfactant system comprising an anionic surfactant or a mixture of anionic surfactants which method comprises adding a polymeric suds stabilizer to said composition, wherein said polymeric suds stabilizer is selected from the group consisting of:

(a) polymers comprising at least one monomeric unit of the formula:

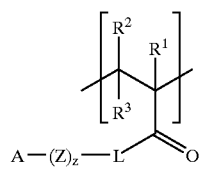

wherein each of $R^1$, $R^2$, $R^3$, L, Z, z and A are as hereinbefore defined; and wherein said polymeric suds stabilizer has a molecular weight of from about 1,000 to about 2,000,000 daltons;

(b) a proteinaceous suds stabilizer, said proteinaceous suds stabilizer having an isoelectric point of from about 7 to about 11.5; and (c) a zwitterionic polymeric suds stabilizer;

A third aspect of the present invention relates to a method of cleaning the skin while avoiding the harsh effects on the skin of an anionic surfactant by washing the skin with the composition comprising a polymeric suds stabilizer selected from the group consisting of:

(a) polymers comprising at least one monomeric unit of the formula:

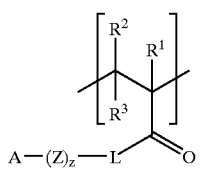

wherein each of $R^1$, $R^2$, $R^3$, L, Z, z and A are as hereinbefore defined; and wherein said polymeric suds stabilizer has a molecular weight of from about 1,000 to about 2,000,000 daltons;

(b) a proteinaceous suds stabilizer, said proteinaceous suds stabilizer having an isoelectric point of from about 7 to about 11.5; and (c) a zwitterionic polymeric suds stabilizer;

A fourth aspect of the present invention relates to a method for manually cleaning an object comprising contacting a user's hands with a washing solution comprising water and a detergent composition in which suds produced by the solution is maintained for an extended period of time by a suds stabilizer, said suds stabilizer comprising i) units capable of having a cationic charge at a pH of from about 4 to about 12;

provided that said suds stabilizer has an average cationic charge density of at least about 0.01 units per 100 daltons molecular weight at a pH of from about 4 to about 12; and wherein said method further including the step of washing the object with said solution; and wherein said suds stabilizer is a, mild, suds enhancing, suds stabilizer such that a user's hands, after submersion in a solution containing said suds stabilizer, are not irritated.

A fifth aspect of the present invention relates to a method of enhancing mildness of a detergent composition comprising a surfactant system comprising an anionic surfactant or a mixture of anionic surfactants which method comprises adding a polymeric suds stabilizer to said composition, wherein said polymeric suds stabilizer comprising:

i) units capable of having a cationic charge at a pH of from about 4 to about 12;

provided that said suds stabilizer has an average cationic charge density of at least about 0.01 units per 100 daltons molecular weight at a pH of from about 4 to about 12;

A sixth aspect of the present invention relates to a method of cleaning the skin while avoiding the harsh effects on the skin of an anionic surfactant by washing the skin with the composition comprising an effective amount of a polymeric suds stabilizer, said polymeric suds stabilizer comprising:

i) units capable of having a cationic charge at a pH of from about 4 to about 12;

provided that said suds stabilizer has an average cationic charge density of at least about 0.01 units per 100 daltons molecular weight at a pH of from about 4 to about 12;

These and other aspects, features and advantages will become apparent to those of ordinary skill in the art from a reading of the following detailed description and the appended claims.

In the description of the invention various embodiments and/or individual features are disclosed. As will be apparent for the skilled practitioner all combinations of such embodiments and features are possible and can result in preferred executions of the invention.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to methods which in addition to providing increased suds volume and increase suds duration, are mild. The methods of the present invention comprise suds boosting polymers selected from (1) polymers comprising at least one monomeric unit; (2) proteinaceous suds stabilizer; (3) zwitterionic polymeric suds stabilizer; and (4) polymers comprising units capable of having a cationic charge. Suitable polymeric suds stabilizers, include be a homopolymers, as well as copolymers, terpolymers, and higher multimers. Mixtures of the polymeric suds stabilizers are also within the scope of the invention.

In addition, the polymers of the present invention act together with surfactants and other adjunct ingredients to provide for efficient grease cutting and anti-redepositon of grease.

It is believed, while not wanting to be limited by theory, that the suds boosting polymers functions primarily by providing a desquamatory action to the composition. It is believed that the suds boosting polymers remove damaged (e.g. dry) skin cells on the surface of the skin, thereby reducing the rough feel associated therewith. The suds boosting polymers removes the effect of prior damage to the skin, giving the skin a fresher, more youthful appearance and feel. When the suds boosting polymers is combined with a detergent surfactant the overall effect is to promote the health of the skin and to provide the consumer with a perceived mildness or skin feel/appearance advantage over other similar compositions which do not contain the suds boosting polymers while still maintaining good cleaning performance.

Alternatively, the polymeric suds stabilizers may, again while not wanting to be limited by theory, just improve the overall feel of the composition to the user.

1. Polymers Comprising at Least One Monomeric Unit

In one aspect of the present invention the polymeric suds stabilizers comprise at least one monomeric unit of the formula:

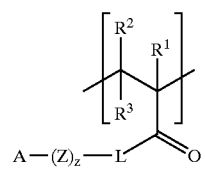

wherein each of $R^1$, $R^2$ and $R^3$ are independently selected from the group consisting of hydrogen, $C_1$ to $C_6$ alkyl, and mixtures thereof, preferably hydrogen, $C_1$ to $C_3$ alkyl, more preferably, hydrogen or methyl. L is selected from the group consisting of a bond, O, $NR^6$, $SR^7R^8$ and mixtures thereof, preferably, O, $NR^6$, wherein $R^6$ is selected from the group consisting of hydrogen, $C_1$ to $C_8$ alkyl and mixtures thereof, preferably, hydrogen, $C_1$ to $C_3$, and mixtures thereof, more preferably hydrogen, methyl; each of $R^7$ and $R^8$ are independently hydrogen, O, $C_1$ to $C_8$ alkyl and mixtures thereof, preferably, hydrogen, $C_1$ to $C_3$, and mixtures thereof, more preferably hydrogen or methyl. By "O", an oxygen linked via a double bond is meant, such as a carbonyl group. Furthermore this means that when either or both $R^7R^8$ is "O", $SR^7R^8$ can have the following structures:

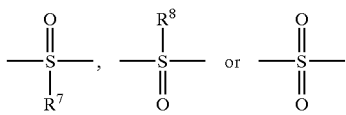

Alternatively, $SR^7R^8$ form a heterocyclic ring containing from 4 to 7 carbon atoms, optionally containing additional hetero atoms and optionally substituted. For example $SR^7R^8$ can be:

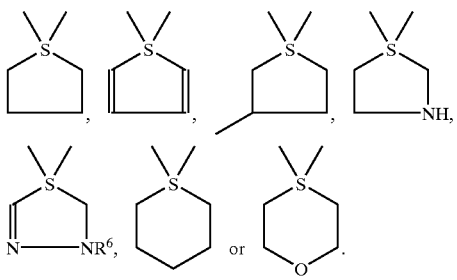

However, it is preferred that $SR^7R^8$, when present, is not a heterocycle.

When L is a bond it means that there is a direct link, or a bond, between the carbonyl carbon atom to Z, when z is not zero. For example:

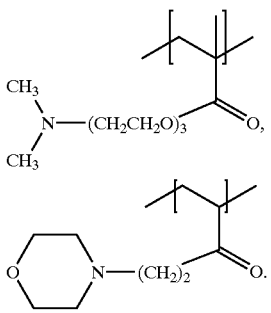

When L is a bond and z is zero, it means L is a bond from the carbonyl atom to A. For example:

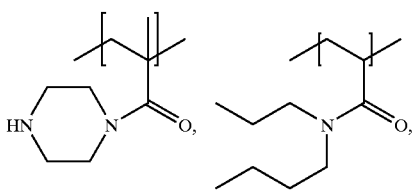

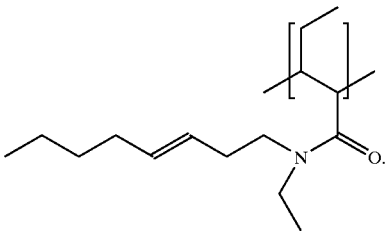

Z is selected from the group consisting of: —(CH$_2$)—, (CH$_2$—CH=CH)—, —(CH$_2$—CHOH)—, (CH$_2$—CHNR$^6$)—, —(CH$_2$—CHR$^{14}$—O)— and mixtures thereof, preferably —(CH$_2$)—. $R^{14}$ is selected from the group consisting of hydrogen, $C_1$ to $C_6$ alkyl and mixtures thereof, preferably hydrogen, methyl, ethyl and mixtures thereof; z is an integer selected from about 0 to about 12, preferably about 2 to about 10, more preferably about 2 to about 6.

A is $NR^4R^5$. Wherein each of $R^4$ and $R^5$ are is independently selected from the group consisting of hydrogen, $C_1$–$C_8$ linear or branched alkyl, alkyleneoxy having the formula:

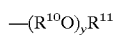

wherein $R^{10}$ is $C_2$–$C_4$ linear or branched alkylene, and mixtures thereof; $R^{11}$ is hydrogen, $C_1$–$C_4$ alkyl, and mixtures thereof; y is from 1 to about 10. Preferably $R^4$ and $R^5$ are independently, hydrogen, $C_1$ to $C_4$ alkyl. Alternatively, $NR^4R^5$ can form a heterocyclic ring containing from 4 to 7 carbon atoms, optionally containing additional hetero atoms, optionally fused to a benzene ring, and optionally substituted by $C_1$ to $C_8$ hydrocarbyl. Examples of suitable heterocycles, both substituted and unsubstituted, are indolyl, isoindolinyl imidazolyl, imidazolinyl, piperidinyl pyrazolyl, pyrazolinyl, pyridinyl, piperazinyl, pyrrolidinyl, pyrrolidinyl, guanidino, amidino, quinidinyl, thiazolinyl, morpholine and mixtures thereof, with morpholino and piperazinyl being preferred. Furthermore the polymeric suds stabilizer has a molecular weight of from about 1,000 to about 2,000,000 preferably from about 5,000 to about 1,000,000, more preferably from about 10,000 to about 750,000, more preferably from about 20,000 to about 500,000, even more preferably from about 35,000 to about 300,000 daltons. The molecular weight of the polymeric suds boosters, can be determined via conventional gel permeation chromatography.

While, it is preferred that the polymeric suds stabilizers be selected from homopolymer, copolymers and terpolymers, other polymers (or multimers) of the at least one monomeric unit, the polymeric suds stabilizers can also be envisioned via polymerization of the at least one monomeric unit with a wider selection of monomers. That is, all the polymeric suds stabilizers, can be a homopolymers, copolymers, terpolymers, etc. of the at least one monomeric unit, or the polymeric suds stabilizer can be copolymers, terpolymers, etc. containing one, two or more of the at least one monomeric unit and one, two or more monomeric units other than the at least one monomeric unit. For example a suitable homopolymer is:

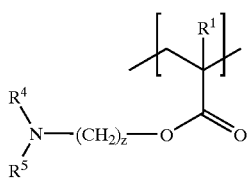

wherein $R^1$, $R^4$, $R^5$ and z are as hereinbefore defined. For example a suitable copolymer is:

(i)

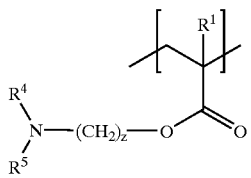

wherein $R^1$, $R^4$, $R^5$ and z are as hereinbefore defined; and (ii)

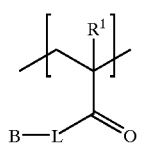

wherein $R^1$ and L are as hereinbefore defined, and B is selected from the group consisting of hydrogen, $C_1$ to $C_8$ hydrocarbyl, $NR^4R^5$, and mixtures thereof; wherein each of $R^4$ and $R^5$ are independently selected from the group consisting of hydrogen, $C_1$ to $C_8$ alkyl, and mixtures thereof, or $NR^4R^5$ form a heterocyclic ring containing from 4 to 7 carbon atoms, optionally containing additional hetero atoms, optionally fused to a benzene ring, and optionally substituted by $C_1$ to $C_8$ hydrocarbyl;

wherein ratio of (i) to (ii) is from about 99:1 to about 1:10. Some preferred examples of

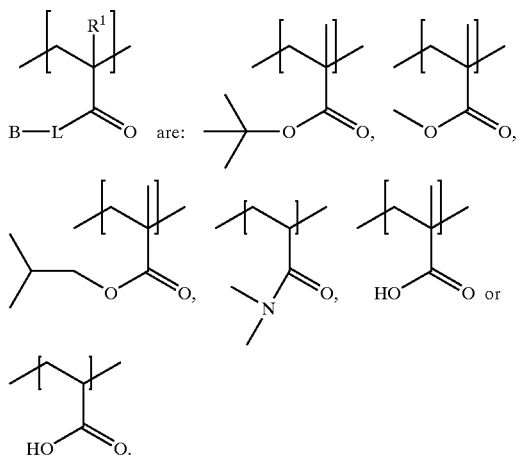

For example a copolymer can be made from two monomers, G and H, such that G and H are randomly distributed in the copolymer, such as GHGGHGGGGGHHG . . . etc.

or G and H can be in repeating distributions in the copolymer, for example

GHGHGHGHGHGHGH . . . etc., or

GGGGGHHGGGGGHH . . . etc.,

The same is true of the terpolymer, the distribution of the three monomers can be either random or repeating.

For example a suitable polymeric suds stabilizer, which is a copolymer is:

(i)

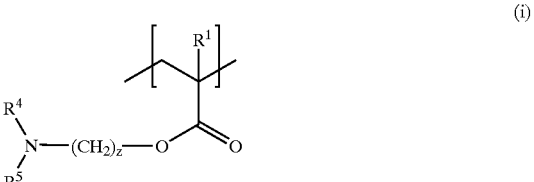

wherein $R^1$, $R^4$, $R^5$ and z are as hereinbefore defined; and ii) either

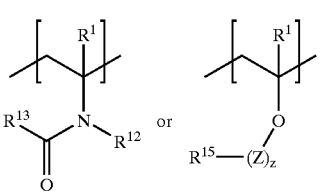

wherein $R^1$ Z and z are as hereinbefore defined, each of $R^{12}$ and $R^{13}$ are independently selected from the group consisting of hydrogen, $C_1$ to $C_8$ alkyl and mixtures thereof, preferably, hydrogen, $C_1$ to $C_3$, and mixtures thereof, more preferably hydrogen, methyl, or $R^{12}$ and $R^{13}$ form a heterocyclic ring containing from 4 to 7 carbon atoms; and $R^{15}$ is selected from the group consisting of hydrogen, $C_1$ to $C_8$ alkyl and mixtures thereof, preferably, hydrogen, $C_1$ to $C_3$, and mixtures thereof, more preferably hydrogen, methyl, wherein ratio of (i) to (ii) is from about 99:1 to about 1:10.

Some preferred at least one monomeric units, which can be additionally combined together to from copolymers and terpolymers include:

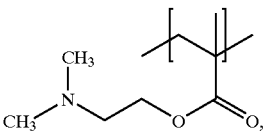

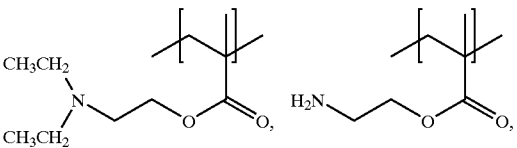

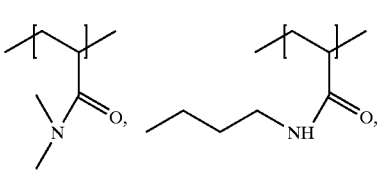

-continued

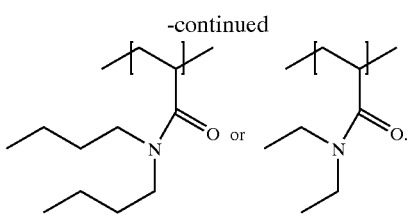

An example of a preferred homopolymer is 2-dimethylaminoethyl methacrylate (DMAM) having the formula:

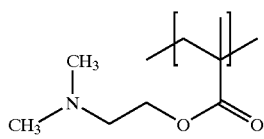

Some preferred copolymers include:

copolymers of

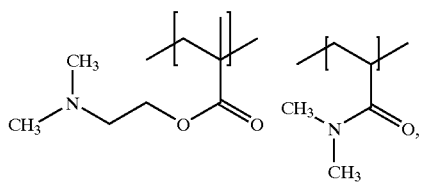

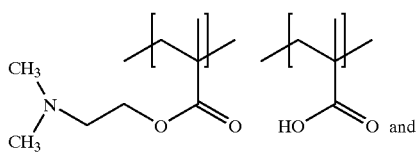

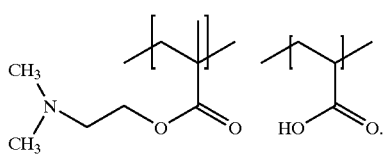

An example of a preferred copolymer is the (DMA)/(DMAM) copolymer having the general formula:

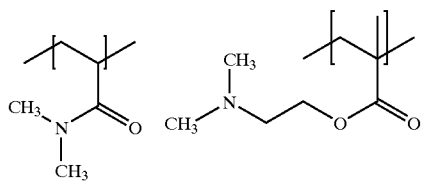

wherein the ratio of (DMA) to (DMAM) is about 1 to about 10, preferably about 1 to about 5, more preferably about 1 to about 3.

An example of a preferred copolymer is the (DMAM)/(DMA) copolymer having the general formula:

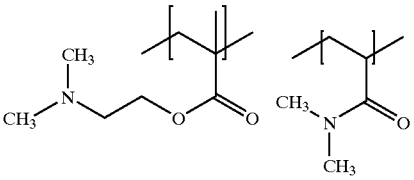

wherein the ratio of (DMAM) to (DMA) is about 1 to about 5, preferably about 1 to about 3.

These polymeric suds stabilizers when used in the methods of the present invention are present at an effective amount of the polymeric suds stabilizers, (i) described herein, preferably from about 0.01% to about 10%, more preferably from about 0.05% to about 5%, most preferably from about 0.1% to about 2% by weight, of said composition. What is meant herein by "an effective amount polymeric suds stabilizers" is that the suds volume and suds duration produced by the presently described compositions are sustained for an increased amount of time relative to a composition which does not comprise one or more of the polymeric suds stabilizer described herein. Additionally, the polymeric suds stabilizer can be present as the free base or as a salt. Typical counter ions include, citrate, maleate, sulfate, chloride, etc.

These and other suitable polymeric suds stabilizers and methods of preparing them, can be found in PCT/US98/24853 filed Nov. 20, 1998.

2. Proteinaceous Suds Stabilizer

The proteinaceous suds stabilizers of the present invention can be peptides, polypeptides, amino acid containing copolymers, and mixtures thereof. Any suitable amino acid can be used to form the backbone of the peptides, polypeptides, or amino acid containing copolymers of the present invention provided at least 10% to about 40% of said amino acids which comprise the peptides are capable of being protonated at a pH of from 7 to about 11.5.

The proteinaceous suds stabilizers of the present invention comprise at least about 10% by weight of one or more amino acid residues, preferably amino acid residues having a proton accepting or proton donor moiety. The proteinaceous suds stabilizers can comprise any other amino acid compatible units which provide for extended suds formation and suds volume.

For the purposes of the present invention the term "peptide" and "polypeptide" stand equally well for polymers which comprise 100% amino acids as described herein below and which have a molecular weight of at least about 1500 daltons. For the purposes of the present invention the term "amino acid containing co-polymers" is defined as "polymeric material comprising at least about 10% by weight of one or more amino acids as defined herein provided said polymeric material has a molecular weight of at least about 1500 daltons".

The preferred proteinaceous suds stabilizers according to the present invention have an isoelectric point of form 7 to about 11.5, preferably from about 8.5 to about 11.5, more preferably form about 9.5 to about 11.

In general, the amino acids suitable for use in forming the proteinaceous suds stabilizers of the present invention have from 2 to 22 carbon atoms, said amino acids having the formula:

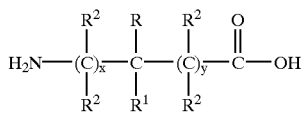

wherein R and $R^1$ are each independently hydrogen, $C_1$–$C_6$ linear or branched alkyl, $C_1$–$C_6$ substituted alkyl, and mixtures thereof. Non-limiting examples of suitable moieties for substitution on the $C_1$–$C_6$ alkyl units include amino, hydroxy, carboxy, amido, thio, thioalkyl, phenyl, substituted phenyl, wherein said phenyl substitution is hydroxy, halogen, amino, carboxy, amido, and mixtures thereof. Further non-limiting examples of suitable moieties for substitution on the R and $R^1$ $C_1$–$C_6$ alkyl units include 3-imidazolyl, 4-imidazolyl, 2-imidazolinyl, 4-imidazolinyl, 2-piperidinyl, 3-piperidinyl, 4-piperidinyl, 1-pyrazolyl, 3-pyrazoyl, 4-pyrazoyl, 5-pyrazoyl, 1-pyrazolinyl, 3-pyrazolinyl, 4-pyrazolinyl, 5-pyrazolinyl, 2-pyridinyl, 3-pyridinyl, 4-pyridinyl, piperazinyl, 2-pyrrolidinyl, 3-pyrrolidinyl, guanidino, amidino, and mixtures thereof. Preferably $R^1$ is hydrogen and at least 10% of R units are moieties which are capable of having a positive or negative charge at a pH of from about 7 to about 11.5. Each $R^2$ is independently hydrogen, hydroxy, amino, guanidino, $C_1$–$C_4$ alkyl, or comprises a carbon chain which can be taken together with R, $R^1$ any $R^2$ units to form an aromatic or non-aromatic ring having from 5 to 10 carbon atoms wherein said ring may be a single ring or two fused rings, each ring being aromatic, non-aromatic, or mixtures thereof. When the amino acids according to the present invention comprise one or more rings incorporated into the amino acid backbone, then R, $R^1$, and one or more $R^2$ units will provide the necessary carbon—carbon bonds to accommodate the formation of said ring. Preferably when R is hydrogen, $R^1$ is not hydrogen, and vice versa; preferably at least one $R^2$ is hydrogen. The indices x and y are each independently from 0 to 2.

An example of an amino acid according to the present invention which contains a ring as part of the amino acid backbone is 2-aminobenzoic acid (anthranilic acid) having the formula:

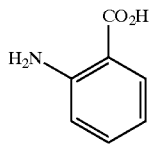

wherein x is equal to 1, y is equal to 0 and R, $R^1$, and 2 $R^2$ units from the same carbon atom are taken together to form a benzene ring.

A further example of an amino acid according to the present invention which contains a ring as part of the amino acid backbone is 3-aminobenzoic acid having the formula:

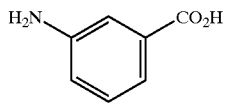

wherein x and y are each equal to 1, R is hydrogen and $R^1$ and four $R^2$ units are taken together to form a benzene ring.

Non-limiting examples of amino acids suitable for use in the proteinaceous suds stabilizers of the present invention wherein at least one x or y is not equal to 0 include 2-aminobenzoic acid, 3-aminobenzoic acid, 4-aminobenzoic acid, b-alanine, and b-hydroxyaminobutyric acid.

The preferred amino acids suitable for use in the proteinaceous suds stabilizers of the present invention have the formula:

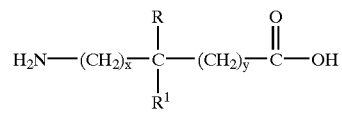

wherein R and $R^1$ are independently hydrogen or a moiety as describe herein above preferably $R^1$ is hydrogen and at least from about 10% to about 40% of R units comprise a moiety having a positive charge at a pH of from about 7 to about 11.5.

More preferred amino acids which comprise the proteinaceous suds stabilizers of the present invention have the formula:

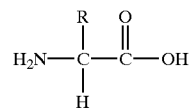

wherein R is hydrogen, $C_1$–$C_6$ linear or branched alkyl, $C_1$–$C_6$ substituted alkyl, and mixtures thereof. R is preferably $C_1$–$C_6$ substituted alkyl wherein preferred moieties which are substituted on said $C_1$–$C_6$ alkyl units include amino, hydroxy, carboxy, amido, thio, $C_1$–$C_4$ thioalkyl, 3-imidazolyl, 4-imidazolyl, 2-imidazolinyl, 4-imidazolinyl, 2-piperidinyl, 3-piperidinyl, 4-piperidinyl, 1-pyrazolyl, 3-pyrazoyl, 4-pyrazoyl, 5-pyrazoyl, 1-pyrazolinyl, 3-pyrazolinyl, 4-pyrazolinyl, 5-pyrazolinyl, 2-pyridinyl, 3-pyridinyl, 4-pyridinyl, piperazinyl, 2-pyrrolidinyl, 3-pyrrolidinyl, guanidino, amidino, phenyl, substituted phenyl, wherein said phenyl substitution is hydroxy, halogen, amino, carboxy, and amido.

An example of a more preferred amino acid according to the present invention is the amino acid lysine having the formula:

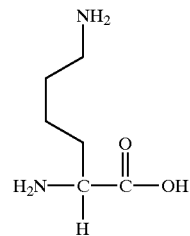

wherein R is a substituted $C_1$ alkyl moiety, said substituent is 4-imidazolyl.

Non-limiting examples of preferred amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and mixtures thereof. The aforementioned amino acids are typically referred to as the "primary a-amino acids", however, the proteinaceous suds stabilizers of the present invention may comprise any amino acid having an R unit which together with the aforementioned amino acids serves to adjust the isoelectric point of the proteinaceous suds stabilizers to a range of from about 7 to about 11.5. For example, further non-limiting examples of amino acids include homoserine, hydroxyproline, norleucine, norvaline, ornithine, penicillamine, and phenylglycine, preferably ornithine. R units preferably comprise moieties which are capable of a cationic or anionic charges within the range of pH from about 7 to about 11.5. Non-limiting examples of preferred amino acids having anionic R units include glutamic acid, aspartic acid, and g-carboxyglutamic acid.

For the purposes of the present invention, both optical isomers of any amino acid having a chiral center serve equally well for inclusion into the backbone of the peptide, polypeptide, or amino acid copolymers. Racemic mixtures of one amino acid may be suitably combined with a single optical isomer of one or more other amino acids depending upon the desired properties of the final proteinaceous suds stabilizer. The same applies to amino acids capable of forming diasteriomeric pairs, for example, threonine.

Polyamino Acid Proteinaceous Suds Stabilizer—One type of suitable proteinaceous suds stabilizer according to the present invention is comprised entirely of the amino acids described herein above. Said polyamino acid compounds may be naturally occurring peptides, polypeptides, enzymes, and the like, provided said compounds have an isoelectric point of from about 7 to about 11.5 and a molecular weight greater than or equal to about 1500 daltons. Preferably the proteinaceous suds stabilizers of the present invention which are comprised entirely of amino acids, comprise from about 10% to about 40% by weight, of amino acids which are capable of being protonated at a pH of from about 7 to about 11.5. An example of a polyamino acid which is suitable as a proteinaceous suds stabilizer according to the present invention is the enzyme lysozyme.

An exception may, from time to time, occur in the case where naturally occurring enzymes, proteins, and peptides are chosen as proteinaceous suds stabilizers. Without wishing to be limited by theory, the unique secondary, tertiary, or quaternary structure of said naturally occurring polypeptides may permit their use even though the amount of protonatable amino acids within the pH range of from about 7 to about 11.5 is outside the range of from about 10% to about 40% by weight. For example an enzyme having an isoelectric point in the range of from about 7 to about 11.5 which only comprises 5% by weight amino acids having R units which are protonated at a pH of from about 7 to about 11.5 may suitably serve as an effective proteinaceous suds stabilizer according to the present invention.

Another class of suitable polyamino acid compound is the synthetic peptide having a molecular weight of at least about 1500 daltons and further comprising from about 10% to about 40% by weight of amino acids capable of being protonated at a pH of form about 7 to about 11.5. In addition, said polyamino acid peptides must have an isoelectric point of form 7 to about 11.5, preferably from about 8.5 to about 11.5, more preferably form about 9.5 to about 11. An example of a polyamino acid synthetic peptide suitable for use as a proteinaceous suds stabilizer according to the present invention is the copolymer of the amino acids lysine, alanine, glutamic acid, and tyrosine having an average molecular weight of 52,000 daltons and a ratio of lys:ala:glu:tyr of approximately 5:6:2:1.

Without wishing to be limited by theory, the presence of one or more cationic amino acids, for example, histidine, ornithine, lysine and the like, is required to insure increased suds stabilization and suds volume. However, the relative amount of cationic amino acid present, as well as the resulting isoelectric point of the polyamino acid, are key to the effectiveness of the resulting material. For example, poly L-lysine having a molecular weight of approximately 18,000 daltons comprises 100% amino acids which have the capacity to possess a positive charge in the pH range of from about 7 to about 11.5, with the result that this material is ineffective as a suds extender and as a greasy soil removing agent.

Peptide Copolymers—Another class of materials suitable for use as proteinaceous suds stabilizers according to the present invention are peptide copolymers. For the purposes of the present invention "peptide copolymers" are defined as "polymeric materials with a molecular weight greater than or equal to about 1500 daltons having an isoelectric point of from about 7 to about 11.5 wherein at least about 10% by weight of said polymeric material comprises one or more amino acids".

Peptide copolymers suitable for use as proteinaceous suds stabilizers may include segments of polyethylene oxide which are linked to segments of peptide or polypeptide to form a material which has increased suds retention as well as formulatability.

Nonlimiting examples of amino acid copolymer classes include the following.

A. Polyalkyleneimine Copolymers.

Polyalkyleneimine copolymers comprise random segments of polyalkyleneimine, preferably polyethyleneimine, together with segments of amino acid residues. For example, tetraethylenepentamine is reacted together with polyglutamic acid and polyalanine to form a copolymer having the formula:

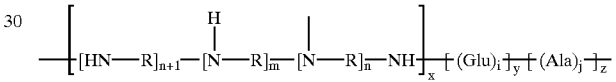

wherein in is equal to 3, n is equal to 0, i is equal to 3, j is equal to 5, x is equal to 3, y is equal to 4, and z is equal to 7.

However, the formulator may substitute other polyamines for polyalkyleneimines, for example, polyvinyl amines, or other suitable polyamine which provides for a source of cationic charge at a pH of from 7 to abut 11.5 and which results in a copolymer having an isoelectric point of from about 7 to about 11.5.

The formulator may combine non-amine polymers with protonatable as well as non-protonatable amino acids. For example, a carboxylate-containing homo-polymer may be reacted with one or more amino acids, for example, histidine and glycine, to form an amino acid containing amido copolymer having the formula:

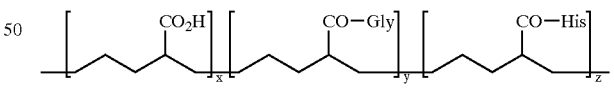

wherein said copolymer has a molecular weight of at least 1500 daltons and a ratio of x:y:z of approximately 2:3:6.

The proteinaceous polymeric suds stabilizers when used in the methods of the present invention are present at an effective amount of one or more proteinaceous suds stabilizers described herein, preferably from about 0.3% to about 5%, more preferably from about 0.4% to about 4%, most preferably from about 0.5% to about 3% by weight, of said composition. What is meant herein by "an effective amount of proteinaceous suds stabilizer" is that the suds produced by the presently described compositions are sustained for an increased amount of time relative to a composition which does not comprise a proteinaceous suds stabilizer described herein.

These and other suitable polymeric suds stabilizers and methods for preparing them, can be found in PCT/US98/24707 filed Nov. 20, 1998.

3. Zwitterionic Polymeric Suds Stabilizers

The zwitterionic polymeric suds stabilizers of the present invention comprise monomeric units which have at least one moiety capable of sustaining a negative charge at a pH of from about 4 to about 12 and at least one moiety capable of sustaining a positive charge within the same pH range. The zwitterionic polymers may be homopolymers or copolymers, each of which may be suitably crosslinked.

The polymeric suds stabilizers of the present invention are zwitterionic polymers. For the purposes of the present invention the term "zwitterionic polymer" is defined as "a polymeric material comprised of one or more monomers wherein each monomer has one or more moieties capable of sustaining a positive or negative charge at a pH of from about 4 to about 12 such that the number of positively charged moieties is equal to the number of negatively charged moieties at the isoelectric point of said polymer."

The polymeric suds stabilizers of the present invention are homopolymers or copolymers wherein the monomers which comprise said homopolymers or copolymers contain a moiety capable of being protonated at a pH of from about 4 to about 12, or a moiety capable of being de-protonated at a pH of from about 4 to about 12, of a mixture of both types of moieties.

A preferred class of zwitterionic polymer suitable for use as a suds volume and suds duration enhancer has the formula:

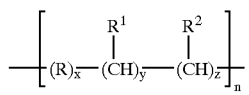

wherein R is $C_1$–$C_{12}$ linear alkylene, $C_1$–$C_{12}$ branched alkylene, and mixtures thereof; preferably $C_1$–$C_4$ linear alkylene, $C_3$–$C_4$ branched alkylene; more preferably methylene and 1,2-propylene. $R^1$ and $R^2$ are defined herein after. The index x is from 0 to 6; y is 0 or 1; z is 0 or 1.

The index n has the value such that the zwitterionic polymers of the present invention have an average molecular weight of from about 1,000 to about 2,000,000 preferably from about 5,000 to about 1,000,000, more preferably from about 10,000 to about 750,000, more preferably from about 20,000 to about 500,000, even more preferably from about 35,000 to about 300,000 daltons. The molecular weight of the polymeric suds boosters, can be determined via conventional gel permeation chromatography.

Anionic Units—$R^1$ is a unit capable of having a negative charge at a pH of from about 4 to about 12. Preferred $R^1$ has the formula:

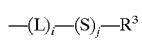

wherein L is a linking unit independently selected from the following:

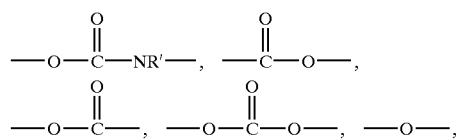

and mixtures thereof, wherein R' is independently hydrogen, $C_1$–$C_4$ alkyl, and mixtures thereof; preferably hydrogen or alternatively R' and S can form a heterocycle of 4 to 7 carbon atoms, optionally containing other hetero atoms and optionally substituted. Preferably the linking group L can be introduced into the molecule as part of the original monomer backbone, for example, a polymer having L units of the formula:

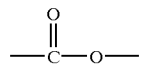

can suitably have this moiety introduced into the polymer via a carboxylate containing monomer, for example, a monomer having the general formula:

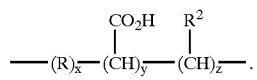

When the index i is 0, L is absent.

For anionic units S is a "spacing unit" wherein each S unit is independently selected from $C_1$–$C_{12}$ linear alkylene, $C_1$–$C_{12}$ branched alkylene, $C_3$–$C_{12}$ linear alkenylene, $C_3$–$C_{12}$ branched alkenylene, $C_3$–$C_{12}$ hydroxyalkylene, $C_4$–$C_{12}$ dihydroxyalkylene, $C_6$–$C_{10}$ arylene, $C_8$–$C_{12}$ dialkylarylene, —$(R^5O)_kR^5$—, —$(R^5O)_kR^6(OR^5)_k$—, —$CH_2CH(OR^7)CH_2$—, and mixtures thereof; wherein $R^5$ is $C_2$–$C_4$ linear alkylene, $C_3$–$C_4$ branched alkylene, and mixtures thereof, preferably ethylene, 1,2-propylene, and mixtures thereof, more preferably ethylene; $R^6$ is $C_2$–$C_{12}$ linear alkylene, and mixtures thereof, preferably ethylene; $R^7$ is hydrogen, $C_1$–$C_4$ alkyl, and mixtures thereof, preferably hydrogen. The index k is from 1 to about 20.

Preferably S is $C_1$–$C_{12}$ linear alkylene, —$(R^5O)_kR^5$—, and mixtures thereof. When S is a —$(R^5O)_kR^5$— unit, said units may be suitably formed by the addition an alkyleneoxy producing reactant (e.g. ethylene oxide, epichlorohydrin) or by addition of a suitable polyethyleneglycol. More preferably S is $C_2$–$C_4$ linear alkylene. When the index j is 0 the S unit is absent.

$R^3$ is independently selected from hydrogen, —$CO_2M$, —$SO_3M$, —$OSO_3M$, —$CH_2P(O)(OM)_2$, —$OP(O)(OM)_2$, units having the formula:

wherein each $R^8$, $R^9$, and $R^{10}$ is independently selected from the group consisting of hydrogen, —$(CH_2)_mR^{11}$, and mixtures thereof, wherein $R^{11}$ is —$CO_2H$, —$SO_3M$, —$OSO_3M$, —$CH(CO_2H)CH_2CO_2H$, —$CH_2P(O)(OH)_2$, —$OP(O)(OH)_2$, and mixtures thereof, preferably —$CO_2H$, —$CH(CO_2H)CH_2CO_2H$, and mixtures thereof, more preferably —$CO_2H$; provided that one $R^8$, $R^9$, or $R^{10}$ is not a hydrogen atom, preferably two $R^8$, $R^9$, or $R^{10}$ units are hydrogen. M is hydrogen or a salt forming cation, preferably hydrogen. The index m has the value from 0 to 10.

Cationic Units—$R^2$ is a unit capable of having a positive charge at a pH of from about 4 to about 12. Preferred $R^2$ has the formula:

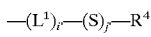

wherein $L^1$ is a linking unit independently selected from the following:

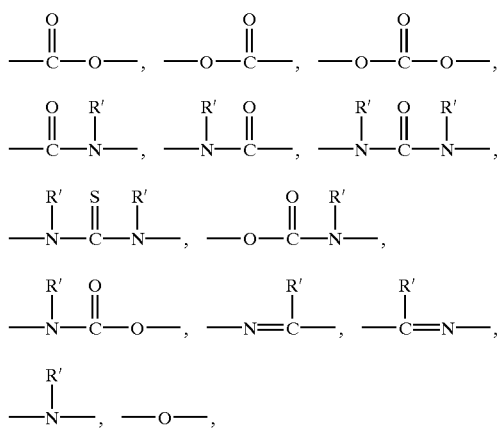

and mixtures thereof; wherein R' is independently hydrogen, $C_1$–$C_4$ alkyl, and mixtures thereof; preferably hydrogen or alternatively R' and S can form a heterocycle of 4 to 7 carbon atoms, optionally containing other hetero atoms and optionally substituted. Preferably $L^1$ has the formula:

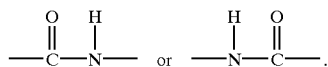

When the index i' is equal to 0, $L^1$ is absent.

For cationic units S is a "spacing unit" wherein each S unit is independently selected from $C_1$–$C_{12}$ linear alkylene, $C_1$–$C_{12}$ branched alkylene, $C_3$–$C_{12}$ linear alkenylene, $C_3$–$C_{12}$ branched alkenylene, $C_3$–$C_{12}$ hydroxyalkylene, $C_4$–$C_{12}$ dihydroxyalkylene, $C_6$–$C_{10}$ arylene, $C_8$–$C_{12}$ dialkylarylene, —$(R^5O)_kR^5$—, —$(R^5O)_kR^6(OR^5)_k$—, —$CH_2CH(OR^7)CH_2$—, and mixtures thereof; wherein $R^5$ is $C_2$–$C_4$ linear alkylene, $C_3$–$C_4$ branched alkylene, and mixtures thereof, preferably ethylene, 1,2-propylene, and mixtures thereof, more preferably ethylene; $R^6$ is $C_2$–$C_{12}$ linear alkylene, and mixtures thereof, preferably ethylene; $R^7$ is hydrogen, $C_1$–$C_4$ alkyl, and mixtures thereof, preferably hydrogen. The index k is from 1 to about 20.

Preferably S is $C_1$–$C_{12}$ linear alkylene, and mixtures thereof. Preferably S is $C_2$–$C_4$ linear alkylene. When the index j' is 0 the S unit is absent.

$R^4$ is independently selected from amino, alkylamino carboxamide, 3-imidazolyl, 4-imidazolyl, 2-imidazolinyl, 4-imidazolinyl, 2-piperidinyl, 3-piperidinyl, 4-piperidinyl, 1-pyrazolyl, 3-pyrazoyl, 4-pyrazoyl, 5-pyrazoyl, 1-pyrazolinyl, 3-pyrazolinyl, 4-pyrazolinyl, 5-pyrazolinyl, 2-pyridinyl, 3-pyridinyl, 4-pyridinyl, piperazinyl, 2-pyrrolidinyl, 3-pyrrolidinyl, guanidino, amidino, and mixtures thereof, preferably dialkylamino having the formula:

—$N(R^{11})_2$ wherein each $R^{11}$ is independently hydrogen, $C_1$–$C_4$ alkyl, and mixtures thereof, preferably hydrogen or methyl or alternatively the two $R^{11}$ can form a heterocycle of 4 to 8 carbon atoms, optionally containing other hetero atoms and optionally substituted.

An example of a preferred zwitterionic polymer according to the present invention has the formula:

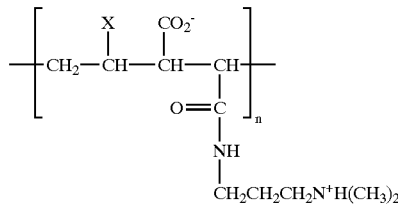

wherein X is $C_6$, n has a value such that the average molecular weight is from about 5,000 to about 1,000,000 daltons.

Further preferred zwitterionic polymers according to the present invention are polymers comprising monomers wherein each monomer has only cationic units or anionic units, said polymers have the formula:

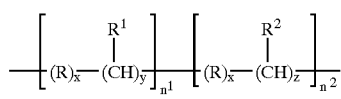

wherein R, $R^1$, x, y, and z are the same as defined herein above; $n^1+n^2=n$ such that n has a value wherein the resulting zwitterionic polymer has a molecular weight of form about 5,000 to about 1,000,000 daltons.

An example of a polymer having monomers with only an anionic unit or a cationic unit has the formula:

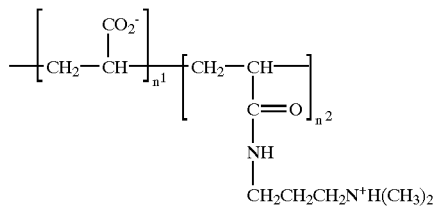

wherein the sum of $n^1$ and $n^2$ provide a polymer with an average molecular weight of from about 5,000 to about 750,000 daltons.

Another preferred zwitterionic polymer according to the present invention are polymers which have limited crosslinking, said polymers having the formula:

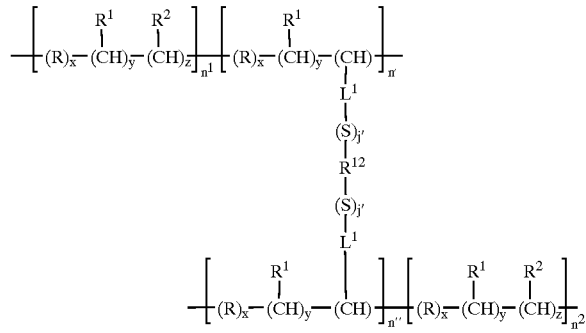

wherein R, $R^1$, $L^1$, S, j', x, y, and z are the same as defined herein above; n' is equal to n", and the value n'+n" is less than or equal to 5% of the value of $n^1+n^2=n$; n 2,000,000 daltons. $R^{12}$ is nitrogen, $C_1$–$C_{12}$ linear alkylene amino alkylene having the formula:

$$—R^{13}—N—R^{13}—$$

$L^1$, and mixtures thereof, wherein each $R^{13}$ is independently $L^1$ or ethylene.

The zwitterionic polymers of the present invention may comprise any combination of monomer units, for example, several different monomers having various $R^1$ and $R^2$ groups can be combined to form a suitable suds stabilizer. Alternatively the same $R^1$ unit may be used with a selection of different $R^2$ units and vice versa.

The zwitterionic polymeric suds stabilizers when used in the methods of the present invention are present at an effective amount, preferably from about 0.01% to about 10%, more preferably from about 0.05% to about 5%, most preferably from about 0.1% to about 2% by weight, of said composition. What is meant herein by "an effective amount of zwitterionic polymeric suds stabilizer" is that the suds produced by the presently described compositions are sustained for an increased amount of time relative to a composition which does not comprise a zwitterionic polymeric suds stabilizer described herein. Additionally, the polymeric suds stabilizer can be present as the free base or as a salt. Typical counter ions include, citrate, maleate, sulfate, chloride, etc.

These and other suitable polymeric suds stabilizers and methods of preparing them, can be found in PCT/US98/24699 filed Nov. 20, 1998.

4. Polymers Comprising Units Capable of Having a Cationic Charge

The fourth aspect of the present invention rela to polymeric materials which provide enhanced suds duration and enhanced suds volume when formulated into detergent compositions. The polymeric material may comprise any material provided the final polymers have an average cationic charge density of from about 0.0005 to about 0.05 units per 100 daltons molecular weight at a pH of from about 4 to about 12. Preferably the average cationic charge density is from about 0.005 to about 0.03 unit per 100 daltons molecular weight.

It is preferred that the polymeric suds stabilizer further comprises:
  ii) units capable of having an anionic charge at a pH of from about 4 to about 12;
  iii) units capable of having an anionic charge and a cationic charge at a pH of from about 4 to about 12;
  iv) units having no charge at a pH of from about 4 to about 12; and
  v) mixtures of units (i), (ii), (iii), and (iv);

The polymeric suds stabilizers of the present invention can be polymers which contain units capable of having a cationic charge at a pH of from about 4 to about 12, provided that the suds stabilizer has an average cationic charge density from about 0.0005 to about 0.05 units per 100 daltons molecular weight at a pH of from about 4 to about 12. Additionally, the polymeric suds stabilizer can be present as the free base or as a salt. Typical counter ions include, citrate, maleate, sulfate, chloride, etc.

For the purposes of the present invention the term "cationic unit" is defined as "a moiety which when incorporated into the structure of the suds stabilizers of the present invention, is capable of maintaining a cationic charge within the pH range of from about 4 to about 12. The cationic unit is not required to be protonated at every pH value within the range of about 4 to about 12." Non-limiting examples of units which comprise a cationic moiety include lysine, ornithine, the monomeric unit having the formula:

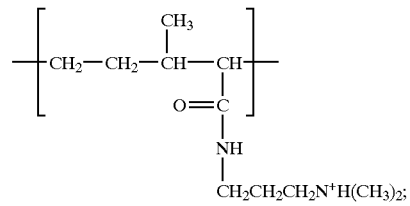

the monomeric unit having the formula:

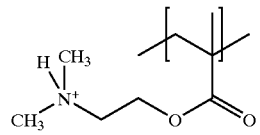

the monomeric unit having the formula:

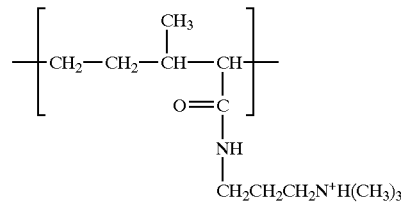

the monomeric unit having the formula:

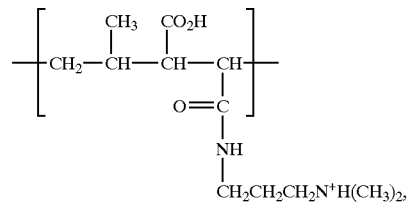

and the monomeric unit having the formula:

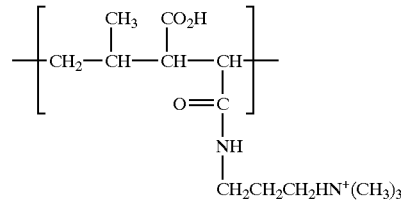

the latter of which also comprises a moiety capable of having an anionic charge at a pH of about 4 to about 12.

For the purposes of the present invention the term "anionic unit" is defined as "a moiety which when incorporated into the structure of the suds stabilizers of the present invention, is capable of maintaining an anionic charge within the pH range of from about 4 to about 12. The anionic unit is not required to be de-protonated at every pH value within the range of about 4 to about 12." Non-limiting examples of units which comprise a anionic moiety include, acrylic acid, methacrylic acid, glutamic acid, aspartic acid, the monomeric unit having the formula:

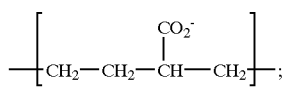

and the monomeric unit having the formula:

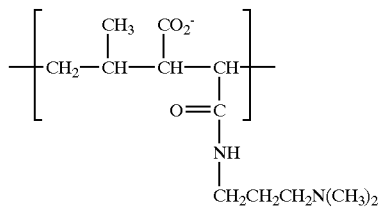

the latter of which also comprises a moiety capable of having a cationic charge at a pH of about 4 to about 12. This latter unit is defined herein as "a unit capable of having an anionic and a cationic charge at a pH of from about 4 to about 12."

For the purposes of the present invention the term "non-charged unit" is defined as "a moiety which when incorporated into the structure of the suds stabilizers of the present invention, has no charge within the pH range of from about 4 to about 12." Non-limiting examples of units which are "non-charged units" are styrene, ethylene, propylene, butylene, 1,2-phenylene, esters, amides, ketones, ethers, and the like.

The units which comprise the polymers of the present invention may, as single units or monomers, have any $pK_a$ value.

The following are non-limiting examples of suitable polymeric materials according to the present invention. The following examples are presented in "classes", however, the formulator may combine any suitable monomers or units to form a polymeric suds stabilizer, for example, amino acids may be combined with polyacrylate units.

The polymeric suds stabilizers polymers which contain units capable of having a cationic charge also include polymers comprising at least one monomeric unit of the formula:

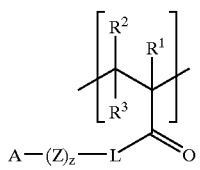

wherein each of $R^1$, $R^2$, $R^3$, $R^4$, L, Z, z, and A are hereinbefore defined. Furthermore, suitable polymers include copolymers of

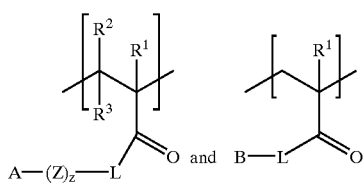

wherein $R^1$ L and B are as hereinbefore defined, and copolymers of

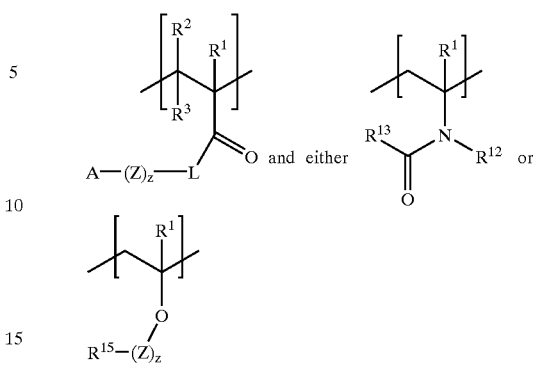

wherein $R^1$, $R^{12}$, $R^{13}$, Z and z are as hereinbefore defined,

The suds stabilizers polymers which contain units capable of having a cationic charge may proteinaceous suds stabilizers, as herein before described, including peptides, polypeptides, amino acid containing copolymers, terpolymers etc., and mixtures thereof. Any suitable amino acid can be used to form the backbone of the peptides, polypeptides, or amino acid, wherein the polymers have an average cationic charge density from about 0.0005 to about 0.05 units per 100 daltons molecular weight at a pH of from about 4 to about 12.

In general, the amino acids suitable for use in forming the proteinaceous suds stabilizers of the present invention have the formula:

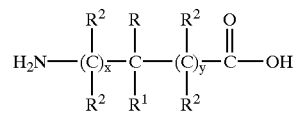

wherein R, $R^1$, $R^2$, x and y and are as hereinbefore defined.

The polymeric suds stabilizers polymers which contain units capable of having a cationic charge may be homopolymers or copolymers wherein the monomers which comprise said homopolymers or copolymers contain a moiety capable of being protonated at a pH of from about 4 to about 12, or a moiety capable of being de-protonated at a pH of from about 4 to about 12, of a mixture of both types of moieties. These suitable zwitterionic polymers are hereinbefore defined.

A Preferred class of suitable for use as a suds volume and suds duration enhancer has the formula:

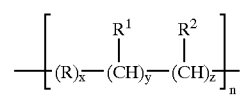

wherein R, $R^1$, $R^2$, x, y, z, and n are hereinbefore defined. Furthermore suitable anionic, cationic and, zwitterionic monomers are also herein before described.

Cationic Charge Density—For the purposes of the methods of the present invention the term "cationic charge density" is defined as "the number of units that are protonated at a specific pH per 100 daltons mass of polymer."

For illustrative purposes only, a polypeptide comprising 10 units of the amino acid lysine has a molecular weight of approximately 1028 daltons, wherein there are 11 —$NH_2$ units. If at a specific pH within the range of from about 4 to about 12, 2 of the —$NH_2$ units are protonated in the form of —$NH_3^+$, then the cationic charge density is 2 cationic charge units÷by 1028 daltons molecular weight=approximately 0.002 units of cationic charge per 100 daltons. This would, therefore, have sufficient cationic charge to suffice the cationic charge density of the present invention, but insufficient molecular weight to be a suitable suds enhancer.

Polymers have been shown to be effective for delivering sudsing benefits provided the polymer contains a cationic moiety, either permanent via a quaternary nitrogen or temporary via protonation. Without being limited by theory, it is believed that the cationic charge must be sufficient to attract the polymer to negatively charged soils but not so large as to cause negative interactions with available anionic surfactants. Herewithin the term cationic charge density is defined as the amount of cationic charge on a given polymer, either by permanent cationic groups or via protonated groups, as a weight percent of the total polymer at the desired wash pH. For example, with poly(-DMAM), we have experimentally determined the pKa, see hereinafter as to how pKa is measured, of this polymer to be 7.0. Thus, if the wash pH is 7.0, then half of the available nitrogens will be protonated (and count as cationic) and the other half will not be protonated (and not be counted in the "cationic charge density"). Thus, since the Nitrogen has a molecular weight of approximately 14 grams/mole, and the DMAM monomer has a molecular weight of approximately 157 grams/mole, the can be calculated:

Cationic Charge Density=(14/157)*50%=0.0446 or 4.46%.

Thus, 4.46% of the polymer contains cationic charges. As another example, one could make a copolymer of DMAM with DMA, where the ratio of monomers is 1 mole of DMAM for 3 moles of DMA. The DMA monomer has a molecular weight of 99 grams/mole. In this case the pKa has been measured to be 7.6. Thus, if the wash pH is 5.0, all of the available nitrogens will be protonated. The cationic charge density is then calculated:

Cationic Charge Density=14/(157+99+99+99)*100%=0.0103, or 1.03%.

Notice that in this example, the minimum repeating unit is considered 1 DMAM monomer plus 3 DMA monomers.

A key aspect of this calculation is the pKa measurement for any protonatable species which will result in a cationic charge on the heteroatom. Since the pKa is dependent on the polymer structure and various monomers present, this must be measure to determine the percentage of protonatable sites to count as a function of the desired wash pH. This is an easy exercise for one skilled in the art.

Based on this calculation, the percent of cationic charge is independent of polymer molecular weight.

The pKa of a polymeric suds booster is determined in the following manner. Make at least 50 mls of a 5% polymer solution, such as a polymer prepared according to any of Examples 1 to 5 as described hereinafter, in ultra pure water (i.e. no added salt). At 25° C., take initial pH of the 5% polymer solution with a pH meter and record when a steady reading is achieved. Maintain temperature throughout the test at 25° C. with a water bath and stir continuously. Raise pH of 50 mls of the aqueous polymer solution to 12 using NaOH (1 N, 12.5 M). Titrate 5 mls of 0.1 N HCl into the polymer solution. Record pH when steady reading is achieved. Repeat steps 4 and 5 until pH is below 3. The pKa was determined from a plot of pH vs. volume of titrant using the standard procedure as disclosed in Quantitative Chemical Analysis, Daniel C. Harris, W. H. Freeman & Chapman, San Francisco, USA 1982.

The detergent compositions for use in the methods of the present invention comprising polymers which contain units capable of having a cationic charge comprise at least an effective amount of one or more polymeric suds stabilizers described herein, preferably from about 0.01% to about 10%, more preferably from about 0.05% to about 5%, most preferably from about 0.1% to about 2% by weight, of said composition. What is meant herein by "an effective amount of polymeric suds stabilizer" is that the suds produced by the presently described compositions are sustained for an increased amount of time relative to a composition which does not comprise a polymeric suds stabilizer described herein.

These and other suitable polymeric suds stabilizers and methods of preparing them, can be found in PCT/US98/24852 filed Nov. 20, 1998.

Detersive Surfactants

The compositions of the present invention preferably contain a detersive surfactant. The detersive surfacatnt is typically selected from the group consisting of anionic, nonionics, cationics, ampholytics, zwitterionics, and mixtures thereof. By selecting the type and amount of detersive surfactant, along with other adjunct ingredients disclosed herein, the present detergent compositions can be formulated to be used in the context of laundry cleaning or in other different cleaning applications, particularly including dishwashing. The particular surfactants used can therefore vary widely depending upon the particular end-use envisioned. Suitable surfactants are described below. Examples of suitable nonionic, anionic, cationic amphoteric and zwitterionic surfactants are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Anionic Surfactants—Anionic surfactants useful in the present invention are preferably selected from the group consisting of, linear alkylbenzene sulfonate, alpha olefin sulfonate, paraffin sulfonates, alkyl ester sulfonates, alkyl sulfates, alkyl alkoxy sulfate, alkyl sulfonates, alkyl alkoxy carboxylate, alkyl alkoxylated sulfates, sarcosinates, taurinates, and mixtures thereof. An effective amount, typically from about 0.5% to about 90%, preferably about 5% to about 60%, more preferably from about 10 to about 30%, by weight of anionic detersive surfactant can be used in the present invention.

Alkyl sulfate surfactants are another type of anionic surfactant of importance for use herein. In addition to providing excellent overall cleaning ability when used in combination with polyhydroxy fatty acid amides (see below), including good grease/oil cleaning over a wide range of temperatures, wash concentrations, and wash times, dissolution of alkyl sulfates can be obtained, as well as improved formulability in liquid detergent formulations are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali (Group IA) metal cation (e.g., sodium, potassium, lithium), substituted or unsubstituted ammonium cations such as methyl-, dimethyl-, and trimethyl ammonium and quaternary ammonium cations, e.g., tetramethyl-ammonium and dimethyl piperdinium, and cations derived from alkanolamines such as ethanolamine, diethanolamine, triethanolamine, and mixtures thereof, and the like. Typically, alkyl chains of $C_{12-16}$ are preferred for lower wash temperatures (e.g., below about 50° C.) and $C_{16-18}$ alkyl chains are preferred for higher wash temperatures (e.g., above about 50° C.).

Alkyl alkoxylated sulfate surfactants are another category of useful anionic surfactant. These surfactants are water soluble salts or acids typically of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperidinium and cations derived from alkanolamines, e.g. monoethanolamine, diethanolamine, and triethanolamine, and mixtures thereof. Exemplary surfactants are $C_{12}$–$C_{18}$ alkyl polyethoxylate (1.0) sulfate, $C_{12}$–$C_{18}$ alkyl polyethoxylate (2.25) sulfate, $C_{12}$–$C_{18}$ alkyl polyethoxylate (3.0) sulfate, and $C_{12}$–$C_{18}$ alkyl polyethoxylate (4.0) sulfate wherein M is conveniently selected from sodium and potassium. Surfactants for use herein can be made from natural or synthetic alcohol feedstocks. Chain lengths represent average hydrocarbon distributions, including branching.

Additionally and preferably, the surfactant may be a midchain branched alkyl sulfate, midchain branched alkyl alkoxylate, or midchain branched alkyl alkoxylate sulfate. These surfactants are further described in No. 60/061,971, Oct. 14, 1997, No. 60/061,975, Oct. 14, 1997, No. 60/062,086, Oct. 14, 1997, No. 60/061,916, Oct. 14, 1997, No. 60/061,970, Oct. 14, 1997, No. 60/062,407, Oct. 14, 1997. Other suitable mid-chain branched surfactants can be found in U.S. Patent application Serial Nos. 60/032,035, 60/031,845, 60/031,916, 60/031,917, 60/031,761, 60/031,762 and 60/031,844. Mixtures of these branched surfactants with conventional linear surfactants are also suitable for use in the present compositions.

Another prefered anionic surfactant are the so-called modified alkyl benzene sulfonate surfactants, or MLAS. Some suitable MLAS surfactants, methods of making them and exempliary compositions are further described in copending U.S. Patent applications Serial Nos. 60/053,319, 60/053,318, 60/053,321, 60/053,209, 60/053,328, 60/053,186, 60/055,437, 60/105,017, and 60/104,962.

Examples of suitable anionic surfactants are given in "Surface Active Agents and Detergents" (Vol. I and II by Schwartz, Perry and Berch).

Nonionic Detergent Surfactants—Suitable nonionic detergent surfactants are generally disclosed in U.S. Pat. No. 3,929,678, Laughlin et al., issued Dec. 30, 1975, at column 13, line 14 through column 16, line 6, incorporated herein by reference. Exemplary, non-limiting classes of useful non-ionic surfactants include: amine oxides, alkyl ethoxylate, alkanoyl glucose amide, alkyl betaines, sulfobetaine and mixtures thereof.

Amine oxides are semi-polar nonionic surfactants and include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula

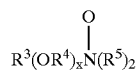

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides. Preferably the amine oxide is present in the composition in an effective amount, more preferably from about 0.1% to about 20%, even more preferably about 0.1% to about 15%, even more preferably still from about 0.5% to about 10%, by weight.

The polyethylene, polypropylene, and polybutylene oxide condensates of alkyl phenols. In general, the polyethylene oxide condensates are preferred. These compounds include the condensation products of alkyl phenols having an alkyl group containing from about 6 to about 12 carbon atoms in either a straight chain or branched chain configuration with the alkylene oxide. In a preferred embodiment, the ethylene oxide is present in an amount equal to from about 5 to about 25 moles of ethylene oxide per mole of alkyl phenol. Commercially available nonionic surfactants of this type include Igepal® CO-630, marketed by the GAF Corporation; and Triton® X-45, X-114, X-100, and X-102, all marketed by the Rohm & Haas Company. These compounds are commonly referred to as alkyl phenol alkoxylates, (e.g., alkyl phenol ethoxylates).

The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 2 to about 18 moles of ethylene oxide per mole of alcohol. Examples of commercially available nonionic surfactants of this type include Tergitol® 15-S-9 (the condensation product of $C_{11}$–$C_{15}$ linear secondary alcohol with 9 moles ethylene oxide), Tergitol® 24-L-6 NMW (the condensation product of $C_{12}$–$C_{14}$ primary alcohol with 6 moles ethylene oxide with a narrow molecular weight distribution), both marketed by Union Carbide Corporation; Neodol® 45-9 (the condensation product of $C_{14}$–$C_{15}$ linear alcohol with 9 moles of ethylene oxide), Neodol® 23-6.5 (the condensation product of $C_{12}$–$C_{13}$ linear alcohol with 6.5 moles of ethylene oxide), Neodol® 45-7 (the condensation product of $C_{14}$–$C_{15}$ linear alcohol with 7 moles of ethylene oxide), Neodol® 45-4 (the condensation product of $C_{14}$–$C_{15}$ linear alcohol with 4 moles of ethylene oxide), marketed by Shell Chemical Company, and Kyro® EOB (the condensation product of $C_{13}$–$C_{15}$ alcohol with 9 moles ethylene oxide), marketed by The Procter & Gamble Company. Other commercially available nonionic surfactants include Dobanol 91-8® marketed by Shell Chemical Co. and Genapol UD-080® marketed by Hoechst. This category of nonionic surfactant is referred to generally as "alkyl ethoxylates."

The preferred alkylpolyglycosides have the formula $$R^2O(C_nH_{2n}O)_t(glycosyl)_x$$

wherein $R^2$ is selected from the group consisting of alkyl, alkyl-phenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Fatty acid amide surfactants having the formula:

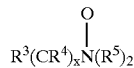

wherein $R^6$ is an alkyl group containing from about 7 to about 21 (preferably from about 9 to about 17) carbon atoms and each $R^7$ is selected from the group consisting of hydrogen, $C_1$–$C_4$ alkyl, $C_1$–$C_4$ hydroxyalkyl, and —$(C^2H_4O)_xH$ where x varies from about 1 to about 3.

Preferred amides are $C_8$–$C_{20}$ ammonia amides, monoethanolamides, diethanolamides, and isopropanolamides.

Preferably the nonionic surfactant, when present in the composition, is present in an effective amount, more preferably from about 0.1% to about 20%, even more preferably about 0.1% to about 15%, even more preferably still from about 0.5% to about 10%, by weight.

Polyhydroxy Fatty Acid Amide Surfactant—The detergent compositions hereof may also contain an effective amount of polyhydroxy fatty acid amide surfactant. By "effective amount" is meant that the formulator of the composition can select an amount of polyhydroxy fatty acid amide to be incorporated into the compositions that will improve the cleaning performance of the detergent composition. In general, for conventional levels, the incorporation of about 1%, by weight, polyhydroxy fatty acid amide will enhance cleaning performance.

The detergent compositions herein will typically comprise about 1% weight basis, polyhydroxy fatty acid amide surfactant, preferably from about 3% to about 30%, of the polyhydroxy fatty acid amide. The polyhydroxy fatty acid amide surfactant component comprises compounds of the structural formula:

wherein: $R^1$ is H, $C_1$–$C_4$ hydrocarbyl, 2-hydroxy ethyl, 2-hydroxy propyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{31}$ hydrocarbyl, preferably straight chain $C_7$–$C_{19}$ alkyl or alkenyl, more preferably straight chain $C_9$–$C_{17}$ alkyl or alkenyl, most preferably straight chain $C_{11}$–$C_{15}$ alkyl or alkenyl, or mixtures thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z will be a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')(CHOH)$—$CH_2OH$, and alkoxylated derivatives thereof, where n is an integer from 3 to 5, inclusive, and R' is H or a cyclic or aliphatic monosaccharide. Most preferred are glycityls wherein n is 4, particularly —$CH_2$—$(CHOH)_4$—$CH_2OH$.

R' can be, for example, N-methyl, N-ethyl, N-propyl, N-isopropyl, N-butyl, N-2-hydroxy ethyl, or N-2-hydroxy propyl.

$R^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

Methods for making polyhydroxy fatty acid amides are known in the art. In general, they can be made by reacting an alkyl amine with a reducing sugar in a reductive amination reaction to form a corresponding N-alkyl polyhydroxyamine, and then reacting the N-alkyl polyhydroxyamine with a fatty aliphatic ester or triglyceride in a condensation/amidation step to form the N-alkyl, N-polyhydroxy fatty acid amide product. Processes for making compositions containing polyhydroxy fatty acid amides are disclosed, for example, in G.B. Patent Specification 809,060, published Feb. 18, 1959, by Thomas Hedley & Co., Ltd., U.S. Pat. No. 2,965,576, issued Dec. 20, 1960 to E. R. Wilson, and U.S. Pat. No. 2,703,798, Anthony M. Schwartz, issued Mar. 8, 1955, and U.S. Pat. No. 1,985,424, issued Dec. 25, 1934 to Piggott, each of which is incorporated herein by reference.

Diamines—The preferred liquid detergent compositions, such as light duty liquid, LDL compositions, useful in the methods of the present invention may further comprise one or more diamines, preferably an amount of diamine such that the ratio of anionic surfactant present to the diamine is from about 40:1 to about 2:1. Said diamines provide for increased removal of grease and greasy food material while maintaining suitable levels of suds.

The diamines suitable for use in the compositions of the present invention have the formula:

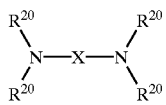

wherein each $R^{20}$ is independently selected from the group consisting of hydrogen, $C_1$–$C_4$ linear or branched alkyl, alkyleneoxy having the formula:

$$-(R^{21}O)_y R^{22}$$

wherein $R^{21}$ is $C_2$–$C_4$ linear or branched alkylene, and mixtures thereof; $R^{22}$ is hydrogen, $C_1$–$C_4$ alkyl, and mixtures thereof; y is from 1 to about 10; X is a unit selected from:
  i) $C_3$–$C_{10}$ linear alkylene, $C_3$–$C_{10}$ branched alkylene, $C_3$–$C_{10}$ cyclic alkylene, $C_3$–$C_{10}$ branched cyclic alkylene, an alkyleneoxyalkylene having the formula:

$$-(R^{21}O)_y R^{21}-$$

wherein $R^{21}$ and y are the same as defined herein above;
  ii) $C_3$–$C_{10}$ linear, $C_3$–$C_{10}$ branched linear, $C_3$–$C_{10}$ cyclic, $C_3$–$C_{10}$ branched cyclic alkylene, $C_6$–$C_{10}$ arylene, wherein said unit comprises one or more electron donating or electron withdrawing moieties which provide said diamine with a $pK_a$ greater than about 8; and
  iii) mixtures of (i) and (ii)
provided said diamine has a $pK_a$ of at least about 8.

The preferred diamines of the present invention have a $pK_1$ and $pK_2$ which are each in the range of from about 8 to about 11.5, preferably in the range of from about 8.4 to about 11, more preferably from about 8.6 to about 10.75. For the purposes of the present invention the term "$pK_a$" stands equally well for the terms "$pK_1$" and "$pK_2$" either separately or collectively. The term $pK_a$ as used herein throughout the present specification in the same manner as used by those of ordinary skill in the art. $pK_a$ values are readily obtained from standard literature sources, for example, "Critical Stability Constants: Volume 2, Amines" by Smith and Martel, Plenum Press, N.Y. and London, (1975).

As an applied definition herein, the $pK_a$ values of the diamines are specified as being measured in an aqueous solution at 25° C. having an ionic strength of from about 0.1 to about 0.5 M. As used herein, the $pK_a$ is an equilibrium constant dependent upon temperature and ionic strength, therefore, value reported by literature references, not measured in the above described manner, may not be within full agreement with the values and ranges which comprise the present invention. To eliminate ambiguity, the relevant conditions and/or references used for $pK_a$'s of this invention are as defined herein or in "Critical Stability Constants: Volume 2, Amines". One optical method of measurement is the potentiometric titration of the acid with sodium hydroxide and determination of the $pK_a$ by suitable methods as described and referenced in "The Chemist's Ready Reference Handbook" by Shugar and Dean, McGraw Hill, NY, 1990.

Preferred diamines for performance and supply considerations are 1,3-bis(methylamino)cyclohexane, 1,3-diaminopropane ($pK_1$=10.5; $pK_2$=8.8), 1,6-diaminohexane ($pK_1$=11; $pK_2$=10), 1,3-diaminopentane (Dytek EP) ($pK_1$= 10.5; $pK_2$=8.9), 2-methyl 1,5-diaminopentane (Dytek A) ($pK_1$=11.2; $pK_2$=10.0). Other preferred materials are the primary/primary diamines having alkylene spacers ranging from $C_4$–$C_8$. In general, primary diamines are preferred over secondary and tertiary diamines.

The following are non-limiting examples of diamines suitable for use in the present invention.

1-N,N-dimethylamino-3-aminopropane having the formula:

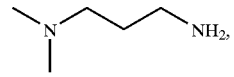

1,6-diaminohexane having the formula:

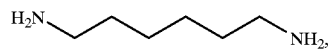

1,3-diaminopropane having the formula:

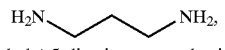

2-methyl-1,5-diaminopentane having the formula:

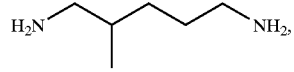

1,3-diaminopentane, available under the tradename Dytek EP, having the formula:

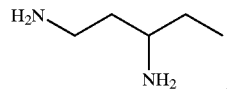

1,3-diaminobutane having the formula:

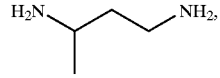

Jeffamine EDR 148, a diamine having an alkylenoxy backbone, having the formula:

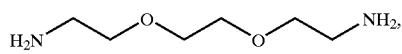

3-methyl-3-aminoethyl-5-dimethyl-1-aminocyclohexane (isophorone diamine) having the formula:

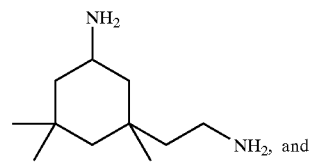

1,3-bis(methylamino)cyclohexane having the formula:

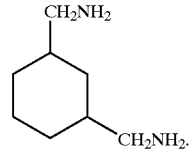

Adjunct Ingredients

The compositions used in the methods of the present invention may further comprise an adjunct ingredient. These will be selected depending upon the desired form and/or application, LDL, personal cleansing composition, etc., of the composition. More than one adjunct ingredient can be incorporated in to the compositions used in the methods.

One highly prefered composition suitable for use in the methods of the present invention includes in addition to the polymeric suds stabilizer, an anionic surfactant, more preferably an alky ethoxy sulfonate, even more preferably an alky ethoxy sulfonate which contains about 0.6 ethoxylates, an amine oxide surfactant, and an enzyme selected from the group consisting of amylase, protease, and mixtures thereof.

Builder—The compositions used in the methods of the according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylene-phosphonic acid. Though less preferred for obvious environmental reasons, phosphate builders can also be used herein.

Suitable polycarboxylates builders for use herein include citric acid, preferably in the form of a water-soluble salt, derivatives of succinic acid of the formula R—CH(COOH)CH$_2$(COOH) wherein R is C10–20 alkyl or alkenyl, preferably C12–16, or wherein R can be substituted with hydroxyl, sulfo sulfoxyl or sulfone substituents. Specific examples include lauryl succinate, myristyl succinate, palmityl succinate 2-dodecenylsuccinate, 2-tetradecenyl succinate. Succinate builders are preferably used in the form of their water-soluble salts, including sodium, potassium, ammonium and alkanolammonium salts.

Other suitable polycarboxylates are oxodisuccinates and mixtures of tartrate monosuccinic and tartrate disuccinic acid such as described in U.S. Pat. No. 4,663,071.

Especially for the liquid execution herein, suitable fatty acid builders for use herein are saturated or unsaturated C10–18 fatty acids, as well as the corresponding soaps. Preferred saturated species have from 12 to 16 carbon atoms in the alkyl chain. The prefer unsaturated fatty acid is oleic acid. Other preferred builder system for liquid compositions is based on dodecenyl succinic acid and citric acid.

Detergency builder salts are normally included in amounts of from 3% to 50% by weight of the composition preferably from 5% to 30% and most usually from 5% to 25% by weight.

Enzymes—Detergent compositions used in the methods of the present invention may further comprise one or more enzymes which provide cleaning performance benefits. Said enzymes include enzymes selected from cellulases, hemicellulases, peroxidases, proteases, gluco-amylases, amylases, lipases, cutinases, pectinases, xylanases, reductases, oxidases, phenoloxidases, lipoxygenases, ligninases, pullulanases, tannases, pentosanases, malanases, β-glucanases, arabinosidases or mixtures thereof. A preferred combination is a detergent composition having a cocktail of conventional applicable enzymes like protease, amylase, lipase, cutinase and/or cellulase. Enzymes when present in the compositions, at from about 0.0001% to about 5% of active enzyme by weight of the detergent composition.

Proteolytic Enzyme—The proteolytic enzyme can be of animal, vegetable or microorganism (preferred) origin. The proteases for use in the detergent compositions herein include (but are not limited to) trypsin, subtilisin, chymotrypsin and elastase-type proteases. Preferred for use herein are subtilisin-type proteolytic enzymes. Particularly preferred is bacterial serine proteolytic enzyme obtained from *Bacillus subtilis* and/or *Bacillus licheniformis*.

Suitable proteolytic enzymes include Novo Industri A/S Alcalase® (preferred), Esperase®, Savinase® (Copenhagen, Denmark), Gist-brocades' Maxatase®, Maxacal® and Maxapem 15® (protein engineered Maxacal®) (Delft, Netherlands), and subtilisin BPN and BPN' (preferred), which are commercially available. Preferred proteolytic enzymes are also modified bacterial serine proteases, such as those made by Genencor International, Inc. (San Francisco, Calif.) which are described in European Patent 251,446B, granted Dec. 28, 1994 (particularly pages 17, 24 and 98) and which are also called herein "Protease B". U.S. Pat. No. 5,030,378, Venegas, issued Jul. 9, 1991, refers to a modified bacterial serine proteolytic enzyme (Genencor International) which is called "Protease A" herein (same as BPN'). In particular see columns 2 and 3 of U.S. Pat. No. 5,030,378 for a complete description, including amino sequence, of Protease A and its variants. Other proteases are sold under the tradenames: Primase, Durazym, Opticlean and Optimase. Preferred proteolytic enzymes, then, are selected from the group consisting of Alcalase® (Novo Industri A/S), BPN', Protease A and Protease B (Genencor), and mixtures thereof. Protease B is most preferred.

Of particular interest for use herein are the proteases described in U.S. Pat. No. 5,470,733.

Also proteases described in our co-pending application U.S. Ser. No. 08/136,797 can be included in the detergent composition of the invention.

Another preferred protease, referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135, +156, +166, +195, +197, +204, +206, +210, +216, +217, +218, +222, +260, +265, and/or +274 according to the numbering of *Bacillus amyloliquefaciens subtilisin*, as described in WO 95/10615 published Apr. 20, 1995 by Genencor International (A. Baeck et al. entitled "Protease-Containing Cleaning Compositions" having U.S. Ser. No. 08/322,676, filed Oct. 13, 1994).

Useful proteases are also described in PCT publications: WO 95/30010 published Nov. 9, 1995 by The Procter & Gamble Company; WO 95/30011 published Nov. 9, 1995 by The Procter & Gamble Company; WO 95/29979 published Nov. 9, 1995 by The Procter & Gamble Company.

Protease enzyme may be incorporated into the compositions in accordance with the invention at a level of from 0.0001% to 2% active enzyme by weight of the composition.

Amylase—Amylases (α and/or β) can be included for removal of carbohydrate-based stains. Suitable amylases are Termamyl® (Novo Nordisk), Fungamyl® and BAN® (Novo Nordisk). The enzymes may be of any suitable origin, such as vegetable, animal, bacterial, fungal and yeast origin. Amylase enzymes are normally incorporated in the detergent composition at levels from 0.0001% to 2%, preferably from about 0.0001% to about 0.5%, more preferably from about 0.0005% to about 0.1%, even more preferably from about 0.001% to about 0.05% of active enzyme by weight of the detergent composition.

Amylase enzymes also include those described in WO95/26397 and in co-pending application by Novo Nordisk PCT/DK96/00056. Other specific amylase enzymes for use in the detergent compositions of the present invention therefore include:

(a) α-amylases characterised by having a specific activity at least 25% higher than the specific activity of Termamyl® at a temperature range of 25° C. to 55° C. and at a pH value in the range of 8 to 10, measured by the Phadebas® α-amylase activity assay. Such Phadebas® α-amylase activity assay is described at pages 9–10, WO95/26397.

(b) α-amylases according (a) comprising the amino sequence shown in the SEQ ID listings in the above cited reference, or an α-amylase being at least 80% homologous with the amino acid sequence shown in the SEQ ID listing.

(c) α-amylases according (a) obtained from an alkalophilic *Bacillus* species, comprising the following amino sequence in the N-terminal: His-His-Asn-Gly-Thr-Asn-Gly-Thr-Met-Met-Gln-Tyr-Phe-Glu-Trp-Tyr-Leu-Pro-Asn-Asp.

A polypeptide is considered to be X % homologous to the parent amylase if a comparison of the respective amino acid sequences, performed via algorithms, such as the one described by Lipman and Pearson in Science 227, 1985, p. 1435, reveals an identity of X %.

(d) α-amylases according (a–c) wherein the α-amylase is obtainable from an alkalophilic *Bacillus* species; and in particular, from any of the strains NCIB 12289, NCIB 12512, NCIB 12513 and DSM 935.

In the context of the present invention, the term "obtainable from" is intended not only to indicate an amylase produced by a *Bacillus* strain but also an amylase encoded by a DNA sequence isolated from such a *Bacillus* strain and produced in an host organism transformed with said DNA sequence.

(e) α-amylase showing positive immunological cross-reactivity with antibodies raised against an α-amylase having an amino acid sequence corresponding respectively to those α-amylases in (a–d).

(f) Variants of the following parent α-amylases which (i) have one of the amino acid sequences shown in corresponding respectively to those α-amylases in (a–e), or (ii) displays at least 80% homology with one or more of said amino acid sequences, and/or displays immunological cross-reactivity with an antibody raised against an α-amylase having one of said amino acid sequences, and/or is encoded by a DNA sequence which hybridizes with the same probe as a DNA sequence encoding an α-amylase having one of said amino acid sequence; in which variants:

1. at least one amino acid residue of said parent α-amylase has been deleted; and/or
2. at least one amino acid residue of said parent α-amylase has been replaced by a different amino acid residue; and/or
3. at least one amino acid residue has been inserted relative to said parent α-amylase;

said variant having an α-amylase activity and exhibiting at least one of the following properties relative to said parent α-amylase: increased thermostability, increased stability towards oxidation, reduced Ca ion dependency, increased stability and/or α-amylolytic activity at neutral to relatively high pH values, increased α-amylolytic activity at relatively high temperature and increase or decrease of the isoelectric point (pI) so as to better match the pI value for α-amylase variant to the pH of the medium.

Said variants are described in the patent application PCT/DK96/00056.

Other amylases suitable herein include, for example, α-amylases described in GB 1,296,839 to Novo; RAPIDASE®, International Bio-Synthetics, Inc. and TERMAMYL®, Novo. FUNGAMYL® from Novo is especially useful. Engineering of enzymes for improved stability, e.g., oxidative stability, is known. See, for example J. Biological Chem., Vol. 260, No. 11, June 1985, pp. 6518–6521. Certain preferred embodiments of the present compositions can make use of amylases having improved stability in detergents such as automatic dishwashing types, especially improved oxidative stability as measured against a reference-point of TERMAMYL® in commercial use in 1993. These preferred amylases herein share the characteristic of being "stability-enhanced" amylases, characterized, at a minimum, by a measurable improvement in one or more of: oxidative stability, e.g., to hydrogen peroxide/tetraacetylethylenediamine in buffered solution at pH 9–10; thermal stability, e.g., at common wash temperatures such as about 60° C.; or alkaline stability, e.g., at a pH from about 8 to about 11, measured versus the above-identified reference-point amylase. Stability can be measured using any of the art-disclosed technical tests. See, for example, references disclosed in WO 9402597. Stability-enhanced amylases can be obtained from Novo or from Genencor International. One class of highly preferred amylases herein have the commonality of being derived using site-directed mutagenesis from one or more of the *Bacillus* amylases, especially the *Bacillus* α-amylases, regardless of whether one, two or multiple amylase strains are the immediate precursors. Oxidative stability-enhanced amylases vs. the above-identified reference amylase are preferred for use, especially in bleaching, more preferably oxygen bleaching, as distinct from chlorine bleaching, detergent compositions herein. Such preferred amylases include (a) an amylase according to the hereinbefore incorporated WO 9402597, Novo, Feb. 3, 1994, as further illustrated by a mutant in which substitution is made, using alanine or threonine, preferably threonine, of the methionine residue located in position 197 of the *B. licheniformis* alpha-amylase, known as TERMAMYL®, or the homologous position variation of a similar parent amylase, such as *B. amyloliquefaciens*, *B. subtilis*, or *B. stearothermophilus*; (b) stability-enhanced amylases as described by Genencor International in a paper entitled "Oxidatively Resistant alpha-Amylases" presented at the 207th American Chemical Society National Meeting, Mar. 13–17, 1994, by C. Mitchinson. Therein it was noted that bleaches in automatic dishwashing detergents inactivate alpha-amylases but that improved oxidative stability amylases have been made by Genencor from *B. licheniformis* NCIB8061. Methionine (Met) was identified as the most likely residue to be modified. Met was substituted, one at a time, in positions 8, 15, 197, 256, 304, 366 and 438 leading to specific mutants, particularly important being M197L and M197T with the M197T variant being the most stable expressed variant. Stability was measured in CASCADE® and SUNLIGHT®; (c) particularly preferred amylases herein include amylase variants having additional modification in the immediate parent as described in WO 9510603 A and are available from the assignee, Novo, as DURAMYL®. Other particularly preferred oxidative stability enhanced amylase include those described in WO 9418314 to Genencor International and WO 9402597 to Novo. Any other oxidative stability-enhanced amylase can be used, for example as derived by site-directed mutagenesis from known chimeric, hybrid or simple mutant parent forms of available amylases. Other preferred enzyme modifications are accessible. See WO 9509909 A to Novo.

Various carbohydrase enzymes which impart antimicrobial activity may also be included in the present invention. Such enzymes include endoglycosidase, Type II endoglycosidase and glucosidase as disclosed in U.S. Pat. Nos. 5,041,236, 5,395,541, 5,238,843 and 5,356,803 the disclosures of which are herein incorporated by reference. Of course, other enzymes having antimicrobial activity may be employed as well including peroxidases, oxidases and various other enzymes.

It is also possible to include an enzyme stabilization system into the compositions of the present invention when any enzyme is present in the composition.

Perfumes—Perfumes and perfumery ingredients useful in the present methods comprise a wide variety of natural and synthetic chemical ingredients, including, but not limited to, aldehydes, ketones, esters, and the like. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes typically comprise from about 0.01% to about 2%, by weight, of the detergent compositions herein, and individual perfumery ingredients can comprise from about 0.0001% to about 90% of a finished perfume composition.

Non-limiting examples of perfume ingredients useful herein include: 7-acetyl-1,2,3,4,5,6,7,8-octahydro-1,1,6,7-tetramethyl naphthalene; ionone methyl; ionone gamma methyl; methyl cedrylone; methyl dihydrojasmonate; methyl 1,6,10-trimethyl-2,5,9-cyclododecatrien-1-yl ketone; 7-acetyl-1,1,3,4,4,6-hexamethyl tetralin; 4-acetyl-6-tert-butyl-1,1-dimethyl indane; para-hydroxy-phenyl-butanone; benzophenone; methyl beta-naphthyl ketone; 6-acetyl-1,1,2,3,3,5-hexamethyl indane; 5-acetyl-3-isopropyl-1,1,2,6-tetramethyl indane; 1-dodecanal, 4-(4-hydroxy-4-methylpentyl)-3-cyclohexene-1-carboxaldehyde; 7-hydroxy-3,7-dimethyl ocatanal; 10-undecen-1-al; iso-hexenyl cyclohexyl carboxaldehyde; formyl tricyclodecane; condensation products of hydroxy-citronellal and methyl anthranilate, condensation products of hydroxycitronellal and indol, condensation products of phenyl acetaldehyde and indol; 2-methyl-3-(para-tert-butylphenyl)-propionaldehyde; ethyl vanillin; heliotropin; hexyl cinnamic aldehyde; amyl cinnamic aldehyde; 2-methyl-2-(para-iso-propylphenyl)-propionaldehyde; coumarin; decalactone gamma; cyclopentadecanolide; 16-hydroxy-9-hexadecenoic acid lactone; 1,3,4,6,7,8-hexahydro-4,6,6,7,8,8-hexamethylcyclopenta-gamma-2-benzopyrane; beta-naphthol methyl ether; ambroxane; dodecahydro-3a,6,6,9a-tetramethylnaphtho[2,1b]furan; cedrol, 5-(2,2,3-trimethylcyclopent-3-enyl)-3-methylpentan-2-ol; 2-ethyl-4-(2,2,3-trimethyl-3-cyclopenten-1-yl)-2-buten-1-ol; caryophyllene alcohol; tricyclodecenyl propionate; tricyclodecenyl acetate; benzyl salicylate; cedryl acetate; and para-(tert-butyl)cyclohexyl acetate.

Particularly preferred perfume materials are those that provide the largest odor improvements in finished product compositions containing cellulases. These perfumes include but are not limited to: hexyl cinnamic aldehyde; 2-methyl-3-(para-tert-butylphenyl)-propionaldehyde; 7-acetyl-1,2,3,4,5,6,7,8-octahydro-1,1,6,7-tetramethyl naphthalene; benzyl salicylate; 7-acetyl-1,1,3,4,4,6-hexamethyl tetralin; para-tert-butyl cyclohexyl acetate; methyl dihydro jasmonate; beta-napthol methyl ether; methyl beta-naphthyl ketone; 2-methyl-2-(para-iso-propylphenyl)-propionaldehyde; 1,3,4,6,7,8-hexahydro-4,6,6,7,8,8-hexamethyl-cyclopenta-gamma-2-benzopyrane; dodecahydro-3a,6,6,9a-tetramethylnaphtho[2,1b]furan; anisaldehyde; coumarin cedrol; vanillin; cyclopentadecanolide; tricyclodecenyl acetate; and tricyclodecenyl propionate.

Other perfume materials include essential oils, resinoids, and resins from a variety of sources including, but not limited to: Peru balsam, Olibanum resinoid, styrax, labdanum resin, nutmeg, cassia oil, benzoin resin, coriander and lavandin. Still other perfume chemicals include phenyl ethyl alcohol, terpineol, linalool, linalyl acetate, geraniol, nerol, 2-(1,1-dimethylethyl)-cyclohexanol acetate, benzyl acetate, and eugenol. Carriers such as diethylphthalate can be used in the finished perfume compositions.

Chelating Agents—The detergent compositions used in the methods herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetrace-tates, N-hydroxyethyl-ethylenediaminetriacetates, nitrilo-triacetates, ethylenediamine tetrapro-prionates, triethylenetetraaminehexacetates, diethylenetriaminepentaacetates, and ethanoldi-glycines, alkali metal, ammonium, and substituted ammonium salts therein and mixtures therein.

Amino phosphonates are also suitable for use as chelating agents in the compositions of the invention when at lease low levels of total phosphorus are permitted in detergent compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisul-fobenzenes such as 1,2-dihydroxy-3,5-disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

The compositions herein may also contain water-soluble methyl glycine diacetic acid (MGDA) salts (or acid form) as a chelant or co-builder. Similarly, the so called "weak" builders such as citrate can also be used as chelating agents.

If utilized, these chelating agents will generally comprise from about 0.1% to about 15% by weight of the detergent compositions herein. More preferably, if utilized, the chelating agents will comprise from about 0.1% to about 3.0% by weight of such compositions.

Composition pH—The compositions used in the methods of the invention will be subjected to acidic stresses created by soils, such as food, when put to use, i.e., diluted and applied to soiled dishes. If a composition with a pH greater than 7 is to be more effective, it preferably should contain a buffering agent capable of providing a generally more alkaline pH in the composition and in dilute solutions, i.e., about 0.1% to 0.4% by weight aqueous solution, of the composition. The pKa value of this buffering agent should be about 0.5 to 1.0 pH units below the desired pH value of the composition (determined as described above). Preferably, the pKa of the buffering agent should be from about 7 to about 10. Under these conditions the buffering agent most effectively controls the pH while using the least amount thereof.

The buffering agent may be an active detergent in its own right, or it may be a low molecular weight, organic or inorganic material that is used in this composition solely for maintaining an alkaline pH. Preferred buffering agents for compositions of this invention are nitrogen-containing materials. Some examples are amino acids such as lysine or lower alcohol amines like mono-, di-, and tri-ethanolamine. Other preferred nitrogen-containing buffering agents are Tri (hydroxymethyl)amino methane $(HOCH_2)_3CNH_3$ (TRIS), 2-amino-2-ethyl-1,3-propanediol, 2-amino-2-methyl-propanol, 2-amino-2-methyl-1,3-propanol, disodium glutamate, N-methyl diethanolamide, 1,3-diamino-propanol N,N'-tetra-methyl-1,3-diamino-2-propanol, N,N-bis(2-hydroxyethyl)glycine (bicine) and N-tris (hydroxymethyl) methyl glycine (tricine). Mixtures of any of the above are also acceptable. Useful inorganic buffers/alkalinity sources include the alkali metal carbonates and alkali metal phosphates, e.g., sodium carbonate, sodium polyphosphate. For additional buffers see McCutcheon's EMULSIFIERS AND DETERGENTS, North American Edition, 1997, McCutcheon Division, MC Publishing Company Kirk and WO 95/07971 both of which are incorporated herein by reference.

The buffering agent, if used, is present in the compositions of the invention herein at a level of from about 0.1% to 15%, preferably from about 1% to 10%, most preferably from about 2% to 8%, by weight of the composition.

Calcium and/or Magnesium Ions—For LDL compositions the presence of calcium and/or magnesium (divalent) ions improves the cleaning of greasy soils for various compositions, i.e., compositions containing alkyl ethoxy sulfates and/or polyhydroxy fatty acid amides. This is especially true when the compositions are used in softened water that contains few divalent ions. It is believed that calcium and/or magnesium ions increase the packing of the surfactants at the oil/water interface, thereby reducing interfacial tension and improving grease cleaning.

Compositions used in the methods of the invention herein containing magnesium and/or calcium ions exhibit good grease removal, manifest mildness to the skin, and provide good storage stability. These ions may be optionally present in the compositions herein at an active level of from about 0.1% to 4%, preferably from about 0.3% to 3.5%, more preferably from about 0.5% to 1%, by weight.

Preferably, the magnesium or calcium ions are added as a hydroxide, chloride, acetate, formate, oxide or nitrate salt to the compositions of the present invention. Calcium ions may also be added as salts of the hydrotrope.

The amount of calcium or magnesium ions present in compositions of the invention will be dependent upon the amount of total surfactant present therein. When calcium ions are present in the compositions of this invention, the molar ratio of calcium ions to total anionic surfactant should be from about 0.25:1 to about 2:1.

Formulating such divalent ion-containing compositions in alkaline pH matrices may be difficult due to the incompatibility of the divalent ions, particularly magnesium, with hydroxide ions. When both divalent ions and alkaline pH are combined with the surfactant mixture of this invention, grease cleaning is achieved that is superior to that obtained by either alkaline pH or divalent ions alone. Yet, during storage, the stability of these compositions becomes poor due to the formation of hydroxide precipitates. Therefore, chelating agents discussed hereinbefore may also be necessary.

Other Ingredients—The detergent compositions used in the methods of the present invention may further preferably comprise one or more detersive adjuncts selected from the following: soil release polymers, polymeric dispersants, polysaccharides, abrasives, bactericides, tarnish inhibitors, builders, enzymes, opacifiers, dyes, buffers, antifungal or mildew control agents, insect repellents, perfumes, hydrotropes, thickeners, processing aids, suds boosters, brighteners, anti-corrosive aids, stabilizers antioxidants and chelants. A wide variety of other ingredients useful in detergent compositions can be included in the compositions herein, including other active ingredients, carriers, hydrotropes, antioxidants, processing aids, dyes or pigments, solvents for liquid formulations, solid fillers for bar compositions, etc. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous.

An antioxidant can be optionally added to the detergent compositions of the present invention. They can be any conventional antioxidant used in detergent compositions, such as 2,6-di-tert-butyl-4-methylphenol (BHT), carbamate, ascorbate, thiosulfate, monoethanolamine(MEA), diethanolamine, triethanolamine, etc. It is preferred that the antioxidant, when present, be present in the composition from about 0.001% to about 5% by weight.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT D10, DeGussa) is admixed with a proteolytic enzyme solution containing 3%–5% of $C_{13-15}$ ethoxylated alcohol (EO 7) nonionic surfactant. Typically, the enzyme/surfactant solution is 2.5× the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Further, these hand dishwashing detergent embodiments preferably further comprises a hydrotrope. Suitable hydrotropes include sodium, potassium, ammonium or water-soluble substituted ammonium salts of toluene sulfonic acid, naphthalene sulfonic acid, cumene sulfonic acid, xylene sulfonic acid.

The detergent compositions of this invention can be in any form, including granular, paste, gel or liquid. Highly preferred embodiments are in liquid or gel form. Liquid detergent compositions can contain water and other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carriers.

An example of the procedure for making granules of the detergent compositions herein is as follows:—Linear aklylbenzenesulfonate, citric acid, sodium silicate, sodium sulfate perfume, diamine and water are added to, heated and mixed via a crutcher. The resulting slurry is spray dried into a granular form.

An example of the procedure for making liquid detergent compositions herein is as follows:—To the free water and citrate are added and dissolved. To this solution amine oxide, betaine, ethanol, hydrotrope and nonionic surfactant are added. If free water isn't available, the citrate are added to the above mix then stirred until dissolved. At this point, an acid is added to neutralize the formulation. It is preferred that the acid be chosen from organic acids such as maleic and citric, however, inorganic mineral acids may be employed as well. In preferred embodiments these acids are added to the formulation followed by diamine addition. AExS is added last.

Non-Aqueous Liquid Detergents

The manufacture of liquid detergent compositions which comprise a non-aqueous carrier medium can be prepared according to the disclosures of U.S. Pat. Nos. 4,753,570; 4,767,558; 4,772,413; 4,889,652; 4,892,673; GB-A-2,158,838; GB-A-2,195,125; GB-A-2,195,649; U.S. Pat. No. 4,988,462; U.S. Pat. No. 5,266,233; EP-A-225,654 (Jun. 16, 1987); EP-A-510,762 (Oct. 28, 1992); EP-A-540,089 (May 5, 1993); EP-A-540,090 (May 5, 1993); U.S. Pat. No. 4,615,820; EP-A-565,017 (Oct. 13, 1993); EP-A-030,096 (Jun. 10, 1981), incorporated herein by reference. Such compositions can contain various particulate detersive ingredients stably suspended therein. Such non-aqueous compositions thus comprise a LIQUID PHASE and, optionally but preferably, a SOLID PHASE, all as described in more detail hereinafter and in the cited references.

The compositions of this invention can be used to form aqueous washing solutions for use hand dishwashing. Generally, an effective amount of such compositions is added to water to form such aqueous cleaning or soaking solutions. The aqueous solution so formed is then contacted with the dishware, tableware, flatware and cooking utensils.

An effective amount of the detergent compositions herein added to water to form aqueous cleaning solutions can comprise amounts sufficient to form from about 500 to 20,000 ppm of composition in aqueous solution. More preferably, from about 800 to 5,000 ppm of the detergent compositions herein will be provided in aqueous cleaning liquor.

Personal Cleansing Compositions

The compositions used in the methods of the present invention may also be a personal cleansing composition. That is a composition for direct application to a persons, skin, hair etc. Examples of personal cleansing compositions includes, but is not limited to, body washes, facial scrubs, shampoos, conditions, medicated shampoos, anti-dandruff shampoos, so-called 2-in-1 shampoos and conditioners, toilet bars, hand soap (including liquid or bar), deodorant soap, and the like.

The conventional personal cleansing composition used in the methods of the present invention additionally contains a conventional personal cleansing additive. The conventional personal cleansing additive is present from about 0.001% to about 49.9% by weight. Preferably, the conventional personal cleansing additive will be present from at least about 0.5%, more preferably, at least about 1%, even more preferably at least about 2%, by weight. Additionally, the conventional personal cleansing additives can also be present at least about 5%, at least about 8% and at least about 10%, by weight but it is more preferable that the conventional personal cleansing additive be present in at least about 2% by weight. Furthermore, the conventional personal cleansing additive will be preferably present in the personal cleansing composition at preferably at less than about 45%, more preferably less than about 40%, even more preferably less than about 35%, even more preferably less than about 30%, even more preferably less than about 20%, by weight. This conventional personal cleansing additive is selected from the group comprising;

a) conditioning agent b) conventional personal care polymer;

c) antidandruff agent d) cosurfactant; and e) mixtures thereof.

These conventional personal cleansing additives are just some of the possible ingredients which can be conventionally added to personal cleansing compositions.

The conditioning agents, (a), useful in the present invention can be further selected from the group comprising 1) non-volatile hydrocarbons conditioning agents;

2) silicone conditioning agents; and 3) mixtures thereof.

The conventional personal care polymers, (b), useful in the present invention can be further selected from the group comprising i) deposition polymers;

ii) styling polymers and solvent;

iii) dispersed phase polymers; and iv) mixtures thereof.

a) Conditioning Agent

The personal cleansing compositions used in the methods of the present invention comprise from about 0.005% to about 20%, preferably from about 0.01% to about 10%, more preferably from about 0.1% to about 5%, and even more preferably from about 0.5% to about 3% of dispersed particles of a nonvolatile hair or skin conditioning agent. Suitable hair or skin conditioning agents include nonvolatile silicone conditioning agents, nonvolatile hydrocarbon conditioning agents, and mixtures thereof.

As used herein, average particle size of the conditioning agent particles may be measured within the personal cleansing compositions by light scattering methods well known in the art for determining average particle size for emulsified liquids. One such method involves the use of a Horiba LA-910 particle size analyzer.

For more information and additional examples of conditioning agents see copending U.S. patent application Ser. No. 08/733,046, filed on Oct. 16, 1996 and U.S. patent application Ser. No. 08/738,156, filed on Oct. 25, 1996. See also U.S. Pat. No. 4,741,855. All three of these references are incorporated herein by reference.

1) Nonvolatile Silicone Conditioning Agents—Preferred conditioning agents useful herein include nonvolatile, dispersed silicone conditioning agents. By nonvolatile is meant that the silicone conditioning agent exhibits very low or no significant vapor pressure at ambient conditions, e.g., 1 atmosphere at 25° C. The nonvolatile silicone conditioning agent preferably has a boiling point at ambient pressure of above about 250° C., preferably of above about 260° C., and more preferably of above about 275° C. By dispersed is meant that the conditioning agent forms a separate, discontinuous phase from the aqueous carrier such as in the form of an emulsion or a suspension of droplets.

The nonvolatile silicone hair conditioning agents suitable for use herein preferably have a viscosity of from about 1,000 to about 2,000,000 centistokes at 25° C., more preferably from about 10,000 to about 1,800,000, and even more preferably from about 100,000 to about 1,500,000. The viscosity can be measured by means of a glass capillary viscometer as set forth in Dow Corning Corporate Test Method CTM0004, Jul. 20, 1970, which is incorporated by reference herein in its entirety. Suitable silicone fluids include polyalkyl siloxanes, polyaryl siloxanes, polyalkylaryl siloxanes, polyether siloxane copolymers, and mixtures thereof. Other nonvolatile silicones having hair conditioning properties can also be used.

The silicones herein also include polyalkyl or polyaryl siloxanes with the following structure:

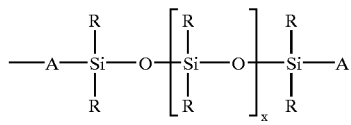

wherein R is alkyl or aryl, and x is an integer from about 7 to about 8,000. "A" represents groups which block the ends of the silicone chains. The alkyl or aryl groups substituted on the siloxane chain (R) or at the ends of the siloxane chains (A) can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable A groups include hydroxy, methyl, methoxy, ethoxy, propoxy, and aryloxy. The two R groups on the silicon atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicones are available, for example, from the General Electric Company in their ViscasilR and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicones, such as highly phenylated polyethyl silicone having refractive indices of about 1.46 or higher, especially about 1.52 or higher. When these high refractive index silicones are used, they should be mixed with a spreading agent, such as a surfactant or a silicone resin, as described below to decrease the surface tension and enhance the film forming ability of the material.

The silicones that can be used include, for example, a polypropylene oxide modified polydimethylsiloxane although ethylene oxide or mixtures of ethylene oxide and propylene oxide can also be used. The ethylene oxide and polypropylene oxide level should be sufficiently low so as not to interfere with the dispersibility characteristics of the silicone. These material are also known as dimethicone copolyols.

Other silicones include amino substituted materials. Suitable alkylamino substituted silicones include those represented by the following structure (II)

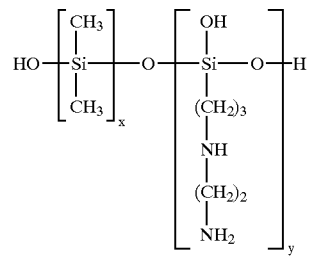

wherein x and y are integers which depend on the molecular weight, the average molecular weight being approximately between 5,000 and 10,000. This polymer is also known as "amodimethicone".

Suitable cationic silicone fluids include those represented by the formula (III)
$(R_1)_a G_{3-a}$—Si—$(-OSiG_2)_n$—$(-OSiG_b(R_1)_{2-b})_m$—O—$SiG_{3-a}(R_1)_a$ in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R^1$ is a monovalent radical of formula $CqH_{2q}L$ in which q is an integer from 2 to 8 and L is chosen from the groups —$N(R_2)CH_2$—$CH_2$—$N(R_2)_2$
—$N(R_2)_2$
—$N(R_2)_3A^-$
—$N(R_2)CH_2$—$CH_2$—$NR_2H_2A^-$ in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

An especially preferred cationic silicone corresponding to formula (III) is the polymer known as "trimethylsilylamodimethicone", of formula (IV):

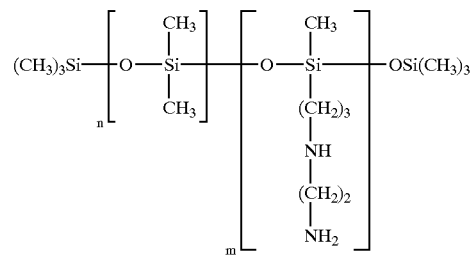

In this formula n and m are selected depending on the exact molecular weight of the compound desired.

Other silicone cationic polymers which can be used in the personal cleansing compositions are represented by the formula (V):

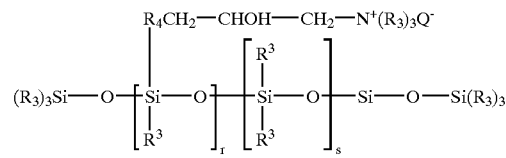

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

References disclosing suitable silicones include U.S. Pat. No. 2,826,551, to Geen; U.S. Pat. No. 3,964,500, to Drakoff, issued Jun. 22, 1976; U.S. Pat. No. 4,364,837, to Pader; and British Patent No. 849,433, to Woolston, all of which are incorporated herein by reference in their entirety. Also incorporated herein by reference in its entirety is "Silicon Compounds" distributed by Petrarch Systems, Inc., 1984. This reference provides an extensive, though not exclusive, listing of suitable silicones.

Another silicone hair conditioning material that can be especially useful is a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicones. This overlap is not intended as a limitation on any of these materials. Silicone gums are described by Petrarch, Id., and others including U.S. Pat. No. 4,152,416, to Spitzer et al., issued May 1, 1979 and Noll, Walter, *Chemistry and Technology of Silicones*, New York: Academic Press 1968. Also describing silicone gums are General Electric Silicone Rubber Product Data Sheets SE 30, SE 33, SE 54 and SE 76. All of these described references are incorporated herein by reference in their entirety. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Also useful are silicone resins, which are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being limited by theory, it is believed that the silicone resins can enhance deposition of other silicones on the hair and can enhance the glossiness of hair with high refractive index volumes.

Other useful silicone resins are silicone resin powders such as the material given the CTFA designation polymethylsilsequioxane, which is commercially available as Tospearl™ from Toshiba Silicones.

Background material on silicones, including sections discussing silicone fluids, gums, and resins, as well as the manufacture of silicones, can be found in Encyclopedia of Polymer Science and Engineering, Volume 15, Second Edition, pp 204–308, John Wiley & Sons, Inc., 1989, which is incorporated herein by reference in its entirety.

Silicone materials and silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

2) Nonvolatile Hydrocarbon Conditioning Agents—Other suitable hair conditioning agents suitable for use in the personal cleansing composition include nonvolatile organic conditioning agents. Suitable nonvolatile organic conditioning agents for use in the composition are those conditioning agents that are known or otherwise effective for use as hair or skin conditioning agent.

The nonvolatile hydrocarbons for use in the personal cleansing composition may be saturated or unsaturated, and may be straight, cyclic or branched chain. By nonvolatile is meant that the hydrocarbon conditioning agent exhibits very low or no significant vapor pressure at ambient conditions, e.g., 1 atmosphere at 25° C. The nonvolatile hydrocarbon agent preferably has a boiling point at ambient pressure of above about 250° C., preferably above about 260° C., and more preferably of above about 275° C. The nonvolatile hydrocarbons preferably have from about 12 to about 40 carbon atoms, more preferably from about 12 to about 30 carbon atoms, and most preferably from about 12 to about 22 carbon atoms. Also encompassed herein are polymeric hydrocarbons of alkenyl monomers, such as polymers of $C_2$–$C_{12}$ alkenyl monomers, including 1-alkenyl monomers such as polyalphaolefin monomers. These polymers can be straight or branched chain polymers. The straight chain polymers will typically be relatively short in length, having a total number of carbon atoms as described above in this paragraph. The branched chain polymers can have substantially higher chain lengths. Also useful herein are the various grades of mineral oils. Mineral oils are liquid mixtures of hydrocarbons that are obtained from petroleum.

Specific examples of suitable nonvolatile hydrocarbons include, but are not limited to, paraffin oil, mineral oil, dodecane, isododecane, hexadecane, isohexadecane, eicosene, isoeicosene, tridecane, triglyceride oils, tetradecane, polyoctene, polydecene, polydodecene, products of polymerization of mixtures of $C_{2-12}$ monomers, for example the polymer produced by the polymerization of polyoctene, polydecene and polydodecene, and mixtures thereof. Isododecane, isohexadeance, and isoeicosene are commercially available as Permethyl 99A, Permethyl 101A, and Permethyl 1082, from Presperse, South Plainfield, N.J. A copolymer of isobutene and normal butene is commercially available as Indopol H-100 from Amoco Chemicals. Preferred among these hydrocarbons are mineral oil, isododecane, isohexadecane, polybutene, polyisobutene, and mixtures thereof.

Optional Suspending Agent—The personal cleansing compositions used in the methods of the present invention may further comprise a suspending agent at concentrations effective for suspending the optional conditioning agent, or other water-insoluble material, in dispersed form in the personal cleansing compositions. Such concentrations range from about 0.1% to about 10%, preferably from about 0.5% to about 5.0%, by weight of the personal cleansing compositions.

Optional suspending agents include crystalline suspending agents that can be categorized as acyl derivatives, long chain amine oxides, or combinations thereof, concentrations of which range from about 0.3% to about 5.0%, preferably from about 0.5% to about 3.0%, by weight of the personal cleansing compositions. When used in the personal cleansing compositions, these suspending agents are present in crystalline form. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl ($C_{16}$–$C_{22}$) dimethyl amine oxides, e.g., stearyl dimethyl amine oxide.

Other suitable suspending agents include xanthan gum at concentrations ranging from about 0.3% to about 3%, preferably from about 0.4% to about 1.2%, by weight of the personal cleansing compositions. The use of xanthan gum as a suspending agent in silicone containing personal cleansing compositions is described, for example, in U.S. Pat. No. 4,788,006, which description is incorporated herein by reference. Combinations of long chain acyl derivatives and xanthan gum may also be used as a suspending agent in the personal cleansing compositions. Such combinations are described in U.S. Pat. No. 4,704,272, which description is incorporated herein by reference.

Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956, available from B. F. Goodrich Company.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other suitable suspending agents may be used in the personal cleansing compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydorxethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

b) Conventional Personal Care Polymer:

The personal cleansing compositions used in the methods of the present invention comprise from about 0.01% to about 20%, preferably from about 0.05% to about 10%, more preferably from about 0.1% to about 5%, and even more preferably from about 0.1% to about 3% of a conventional personal care polymer. Suitable conventional personal care polymers include:

i) deposition polymers;

ii) styling polymers and solvent;

iii) dispersed phase polymers; and iv) mixtures thereof.

i) Deposition Polymer—The personal cleansing compositions used in the methods of the present invention can additionally comprise an organic deposition polymer as a deposition aid. It can be present at levels of from about 0.01 to about 5%, preferably from about 0.05 to about 1%, more preferably from about 0.08% to about 0.5% by weight. The polymer may be a homopolymer or be formed from two or more types of monomers. The molecular weight of the polymer will generally be between about 25,000 and about 10,000,000, preferably between about 100,000 and about 5,000,000, more preferably in the range between about 300,000 to about 3,000,000 and most preferably from about 500,000 to about 2,000,000. Preferably the deposition polymer is a cationic polymer and preferably will have cationic nitrogen containing groups such as quaternary ammonium or protonated amino groups, or a mixture thereof. It is preferred that when the deposition polymer is present there is additionally present in the composition a hair conditioning agent, antidandruff agent, styling polymer or mixtures thereof, all of which are defined hereafter. Alternatively the deposition polymer can be used independently, that is on its own, in the personal cleansing composition.

See copending U.S. patent application Ser. Nos. 07/960,473, 08/738,156, filed on Oct. 25, 1996, 60/053,319, filed on Jul. 21, 1997, all of which are incorporated herein by reference, for exemplification of deposition polymers.

The cationic charge density has been found to need to be at least 0.1 meq/g, preferably above 0.5 and most preferably above 0.8 or higher. The cationic charge density should not exceed 5 meq/g, it is preferably less than 3 and more preferably less than 2 meq/g. The charge density can be measured using the Kjeldahl method and should be within the above limits at the desired pH of use, which will in general be from about 3 to 9 and preferably between 4 and 8.

The concentration of the deposition polymer in the personal cleansing when it is a cationic polymer is preferably from about 0.025% to about 3%, more preferably from about 0.05% to about 2%, even more preferably from about 0.1% to about 1%, by weight of the personal cleansing composition.

Any anionic counterions can be use in association with the cationic polymers so long as the polymers remain soluble in water, in the personal cleansing composition, or in a coacervate phase of the personal cleansing composition, and so long as the counterions are physically and chemically compatible with the essential components of the personal cleansing composition or do not otherwise unduly impair product performance, stability or aesthetics. Non limiting examples of such counterions include halides (e.g., chlorine, fluorine, bromine, iodine), sulfate and methylsulfate.

The cationic nitrogen-containing moiety of the cationic polymer is generally present as a substituent on all, or more typically on some, of the monomer units thereof. Thus, the cationic polymer for use in the personal cleansing composition includes homopolymers, copolymers, terpolymers, and so forth, of quaternary ammonium or cationic amine-substituted monomer units, optionally in combination with non-cationic monomers referred to herein as spacer monomers. Non limiting examples of such polymers are described in the *CTFA Cosmetic Ingredient Dictionary,* 3rd edition, edited by Estrin, Crosley, and Haynes, (The Cosmetic, Toiletry, and Fragrance Association, Inc., Washington, D.C. (1982)), which description is incorporated herein by reference.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$–$C_7$ alkyl groups, more preferably $C_1$–$C_3$ alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the personal cleansing. In general secondary and tertiary amines, especially tertiary, are preferred.

Amines substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium sale, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$ alkyls.

The cationic polymers hereof can comprise mixtures of monomer units derived from amine- and/or quaternary ammonium-substituted monomer and/or compatible spacer monomers.

Suitable cationic deposition polymers include, for example: copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA" as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA and Polyquaternium-11) such as those commercially from ISP Corporation (Wayne, N.J., USA) under the GAFQUAT tradename (e.g., GAFQAT 755N); cationic diallyl quaternary ammonium-containing polymers including, for example, dimethyldiallyammonium chloride homopolymer and copolymers of acrylamide and dimethyldiallyammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives. Cationic polysaccharide polymer materials suitable for use herein include those of the formula:

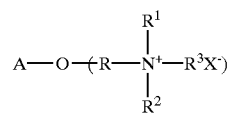

wherein: A is an anhydroglucose residual group, such as starch or cellulose anhydroglucose residual, R is an alkylene oxyalklene, polyoxyalkylene, or hydroxyalkylene group, or combination thereof, $R^1$, $R^2$ and $R^3$ independently are alkyl, aryl, alkylaryl, arylalkyl, alkoxyalkyl, or alkoxyaryl ups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer JR (trademark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other cationic polymers that can be used include cationic guar gum derivatives, such as guar hydroxypropyltrimonium chloride (commercially available from Celanese Corp. in their Jaguar trade mark series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

The deposition polymer does not have to be soluble in the personal cleansing composition. Preferably, however, the cationic polymer is either soluble in the personal cleansing composition, or in a complex coacervate phase in the personal cleansing composition formed by the cationic polymer and anionic material. Complex coacervates of the cationic polymer can be formed with anionic surfactants or with anionic polymers that can optionally be added to the composition hereof (e.g., sodium polystyrene sulfonate).

Coacervate formation is dependent upon a variety of criteria such as molecular weight, concentration, and ratio of interacting ionic materials, ionic strength (including modification of ionic strength, for example, by addition of salts), charge density of the cationic and anionic species, pH, and temperature. Coacervate systems and the effect of these parameters have been described, for example, by J. Caelles, et al., "Anionic and Cationic Compounds in Mixed Systems", *Cosmetics & Toiletries*, Vol. 106, April 1991, pp 49–54, C. J. van Oss, "Coacervation, Complex-Coacervation and Flocculation", *J. Dispersion Science and Technology*, Vol. 9 (5, 6), 1988–89, pp 561–573, and D. J. Burgess, "Practical Analysis of Complex Coacervate Systems", *J. of Colloid and Interface Science*, Vol. 140, No. 1, November 1990, pp 227–238, which descriptions are incorporated herein by reference.

It is believe to be particularly advantageous for the cationic polymer to be present in the personal cleansing in a coacervate phase, or to form a coacervate phase upon application or rinsing of the personal cleansing to or from the hair. Complex coacervates are believed to more readily deposit on the hair. Thus, in general, it is preferred that the cationic polymer exist in the personal cleansing as a coacervate phase or form a coacervate phase upon dilution. If not already a coacervate in the personal cleansing, the cationic polymer will preferably exist in a complex coacervate form in the personal cleansing upon dilution with water to a water:personal cleansing composition rate ratio of about 20:1, more preferably at about 10:1, even more preferably at about 8:1.

Techniques for analysis of formation of complex coacervates are known in the art. For example, microscopic analyses of the personal cleansing compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phase dispersed in the composition.

Preferably the deposition polymer is selected from the group comprising cationic hydroxyalkyl cellulose ethers and cationic guar derivatives. Particularly preferred deposition polymers are Jaguar C13S, Jaguar C15, Jaguar C17 and Jaguar C16 and Jaguar C162. Other preferred cationic cellulose ethers include Polymer JR400, JR30M and JR125.

Surfactant soluble Conditioning Oil—The shampoo compositions used in the methods of the present invention may additionally comprise a low viscosity, surfactant soluble conditioning oil which is solubilized in the surfactant component as an additional hair conditioning agent for use in combination with the cationic hair conditioning polymer described hereinbefore. The concentration of the low viscosity, surfactant soluble oil ranges from about 0.05% to about 3%, preferably from about 0.08% to about 1.5%, more preferably from about 0.1% to about 1%, by weight of the shampoo composition.

The low viscosity, surfactant soluble, conditioning oils are water insoluble, water dispersible, liquids selected from the group consisting of hydrocarbon oils and fatty esters, or combinations thereof, wherein the surfactant soluble conditioning oil has a viscosity of from about 1 to about 300 centipoise, preferably from about 1 to about 150 centipoise, more preferably from about 2 to about 50 centipoise, as measured at 40° C. according to ASTM D-445.

It has been found that these low viscosity surfactant soluble conditioning oils provide the shampoo composition with improved conditioning performance when used in combination with the deposition polymers described herein. These surfactant soluble conditioning oils are believed to be solubilized in the surfactant micelles of the shampoo composition. It is also believed that this solubilization into the surfactant micelles contributes to the improved hair conditioning performance of the shampoo compositions herein.

Suitable surfactant soluble conditioning oils for use in the shampoo composition include hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers thereof. Straight chain hydrocarbon oils preferably contain from about 12 to about 19 carbon atoms. Branched chain hydrocarbon oils, including hydrocarbon polymers, can and typically will contain more than 19 carbon atoms. Specific non limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and combinations thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, sold by Permethyl Corporation. Hydrocarbon polymers such as polybutene and polydecene, especially polybutene, can also be used.

Other surfactant soluble conditioning oils for use in the shampoo composition include a liquid polyolefin such as a liquid polyalphaolefin or a hydrogenated liquid polyalphaolefin. Polyolefins suitable for use in the shampoo composition herein are prepared by polymerization of olefenic monomers containing from about 4 to about 14 carbon atoms, preferably from about 6 to about 12 carbon atoms. Polyalphaolefins are preferred, and are prepared by polymerization of 1-alkene monomers having from about 4 to about 14 carbon atoms, preferably from about 6 to about 12 carbon atoms.

Non limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and combinations thereof. Also suitable for preparing the polyolefin liquids are olefin-containing refinery feedstocks or effluents. Preferred, however, are the hydrogenated alpha-olefin monomers having from about 4 to about 14 carbon atoms, or combinations thereof, examples of which include 1-hexene to 1-hexadecenes and combinations thereof, and preferably are 1-octene to 1-tetradecene or combinations thereof.

(ii) Styling polymer—The personal cleansing compositions used in the methods of the present invention may additionally contain a water-insoluble hair styling polymer, concentrations of which range from about 0.1% to about 10%, preferably from about 0.3% to about 7%, more preferably from about 0.5% to about 5%, by weight of the composition. These styling polymers provide the personal cleansing composition of the present invention with hair styling performance by providing a thin polymeric film on the hair after application from a personal cleansing composition. The polymeric film deposited on the hair has adhesive and cohesive strength, as is understood by those skilled in the art. It is essential that when a styling polymer is present in the personal cleansing compositions of the invention that a solvent, defined hereafter, is also present in the It is preferred that when a styling polymer is present a deposition polymer be also present. This combination improves deposition and retention of the styling polymer. Furthermore, it is preferd that when the personal cleansing composition contains a styling polymer it is preferred that a cationic spreading agent be present.

Many such polymers are known in the art, including water-insoluble organic polymers and water-insoluble silicone-grafted polymers, all of which are suitable for use in the personal cleansing composition herein provided that they also have the requisite features or characteristics described hereinafter. Such polymers can be made by conventional or otherwise known polymerization techniques well known in the art, an example of which includes free radical polymerization.

See copending U.S. patent application Ser. Nos. 08/738,211, filed on Oct. 25, 1996 and 60/053,319, filed on Oct. 25, 1996 both of which are incorporated herein by reference.

Examples of suitable organic and silicone grafted polymer for use in the personal cleansing composition of the present invention are described in greater detail hereinafter.

Organic styling polymer—The styling polymers suitable for use in the methods of the present invention include organic styling polymers well known in the art. The organic styling polymers may be homopolymers, copolymers, terpolymers or other higher polymers, but must comprise one or more polymerizable hydrophobic monomers to thus render the resulting styling polymer hydrophobic and water-insoluble as defined herein. The styling polymers may therefore further comprise other water soluble, hydrophilic monomers provided that the resulting styling polymers have the requisite hydrophobicity and water insolubility.

As used herein, the term "hydrophobic monomer" refers to polymerizable organic monomers that can form with like monomers a water-insoluble homopolymer, and the term "hydrophilic monomer" refers to polymerizable organic monomers that can form with like monomers a water-soluble homopolymer.

The organic styling polymers preferably have a weight average molecular weight of at least about 20,000, preferably greater than about 25,000, more preferably greater than about 30,000, most preferably greater than about 35,000.

There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 2,000,000. Preferably, the weight average molecular weight will be between about 20,000 and about 2,000,000, more preferably between about 30,000 and about 1,000,000, and most preferably between about 40,000 and about 500,000.

The organic styling polymers also preferably have a glass transition temperature (Tg) or crystalline melting point (Tm) of at least about −20° C., preferably from about 20° C. to about 80° C., more preferably from about 20° C. to about 60° C. Styling polymers having these Tg or Tm values form styling films on hair that are not unduly sticky or tacky to the touch. As used herein, the abbreviation "Tg" refers to the glass transition temperature of the backbone of the polymer, and the abbreviation "Tm" refers to the crystalline melting point of the backbone, if such a transition exists for a given polymer. Preferably, both the Tg and the Tm, if any, are within the ranges recited hereinabove.

The organic styling polymers are carbon chains derived from polymerization of hydrophobic monomers such as ethylenically unsaturated monomers, cellulosic chains or other carbohydrate-derived polymeric chains. The backbone may comprise ether groups, ester groups, amide groups, urethanes, combinations thereof, and the like.

The organic styling polymers may further comprise one or more hydrophilic monomers in combination with the hydrophobic monomers described herein, provided that the resulting styling polymer has the requisite hydrophobic character and water-insolubility. Suitable hydrophilic monomers include, but are not limited to, acrylic acid, methacrylic acid, N,N-dimethylacrylamide, dimethyl aminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), salts of any acids and amines listed above, and mixtures thereof. Preferred hydrophilic monomers include acrylic acid, N,N-dimethyl acrylamide, dimethylaminoethyl methacrylate, quaternized dimethyl aminoethyl methacrylate, vinyl pyrrolidone, salts of acids and amines listed above, and combinations thereof.

Suitable hydrophobic monomers for use in the organic styling polymer include, but are not limited to, acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri methyl-1-hexanol, 1-decanol, 1-dodecanol, 1-hexadecanol, 1-octa decanol, and the like, the alcohols having from about 1 to about 18 carbon atoms, preferably from about 1 to about 12 carbon atoms; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred hydrophobic monomers include n-butyl methacrylate, isobutyl methacrylate, t-butyl acrylate, t-butyl methacrylate, 2-ethylhexyl methacrylate, methyl methacrylate, vinyl acetate, and mixtures thereof, more preferably t-butyl acrylate, t-butyl methacrylate, or combinations thereof.

The styling polymers for use in the personal cleansing composition preferably comprise from about 20% to 100%, more preferably from about 50% to about 100%, even more preferably from about 60% to about 100%, by weight of the hydrophobic monomers, and may further comprise from zero to about 80% by weight of hydrophilic monomers. The particular selection and combination of monomers for incorporation into the styling polymer will help determine its formulational properties. By appropriate selection and combination of, for example, hydrophilic and hydrophobic monomers, the styling polymer can be optimized for physical and chemical compatibility with the selected styling polymer solvent described hereinafter and other components of the personal cleansing composition. The selected monomer composition of the organic styling polymer must, however, render the styling polymer water-insoluble but may be soluble in the selected solvent described hereinafter. In this context, the organic styling polymer is soluble in the solvent if the organic polymer is solubilized in the solvent at 25° C. at the polymer and solvent concentrations of the personal cleansing formulation selected. However, a solution of the organic styling polymer and solvent may be heated to speed up solubility of the styling polymer in the solvent. Such styling polymer and solvent formulation, including the selection of monomers for use in the styling polymer, to achieve the desired solubility is well within the skill of one in the art.

Examples of preferred organic styling polymers include t-butyl acrylate/2-ethylhexyl acrylate copolymers having a weight/weight ratio of monomers of about 95/5, about 90/10, about 80/20, about 70/30, about 60/40, and about 50/50; t-butyl acrylate/2-ethylhexyl methacrylate copolymers having a weight/weight ratio of monomers of about 95/5, about 90/10, about 80/20, about 70/30, about 60/40, and about 50/50; t-butyl methacrylate/2-ethylhexyl acrylate copolymers having a weight/weight ratio of monomers of about 95/5, about 90/10, about 80/20, about 70/30, about 60/40, and about 50/50; t-butyl methacrylate/2-ethylhexyl methacrylate copolymers having a weight/weight ratio of monomers of about 95/5, about 90/10, about 80/20, about 70130, about 60/40, and about 50/50; t-butyl ethacrylate/2-ethylhexyl methacrylate copolymers having a weight/weight ratio of monomers of about 95/5, about 90/10, about 80/20, about 70/30, about 60/40, and about 50/50; vinyl pyrrolidone/vinyl acetate copolymers having a weight/weight ratio of monomers of about 10/90, and about 5/95; and mixtures thereof.

Especially preferred polymers are t-butyl acrylate/2-ethylhexyl methacrylate copolymers having a weight/weight ratio of monomers of about 95/5, about 90/10, about 80/20, about 70/30, about 60/40, and about 50/50; 1-butyl methacrylate/2-ethylhexyl methacrylate copolymers having a weight/weight ratio of monomers of about 95/5, about 90/10, about 80/20, about 70/30, about 60/40, and about 50/50, and mixtures thereof.

Examples of other suitable styling polymers are described in U.S. Pat. No. 5,120,531, to Wells et at., issued Jun. 9, 1992; U.S. Pat. No. 5,120,532, to Wells et al., issued Jun. 9, 1992; U.S. Pat. No. 5,104,642, to Wells et al., issued Apr. 14, 1992; U.S. Pat. No. 4,272,511, to Papantoniou et al., issued Jun. 9, 1981; U.S. Pat. No. 4,963,348, to Bolich et al., issued Oct. 16, 1990 and U.S. Pat. No. 4,196,190, to Gehman et al., issued Apr. 1, 1980, which descriptions are incorporated herein by reference.

Silicone-grafted styling polymer—Other suitable styling polymers for use in the methods of the present invention are silicone-grafted hair styling resins. These polymers may be used alone or in combination with the organic styling polymers described hereinbefore. Many such polymers suitable for use in the personal cleansing composition herein are known in the art. These polymers are characterized by polysiloxane moieties covalently bonded to and pendant from a polymeric carbon-based backbone.

The backbone of the silicone-grafted polymer is preferably a carbon chain derived from polymerization of ethylenically unsaturated monomers, but can also be cellulosic chains or other carbohydrate-derived polymeric chains to which polysiloxane moieties are pendant. The backbone can also include ether groups, ester groups, amide groups, urethane groups and the like. The polysiloxane moieties can be substituted on the polymer or can be made by co-polymerization of polysiloxane-containing polymerizable monomers (e.g. ethylenically unsaturated monomers, ethers, and/or epoxides) with non-polysiloxane-containing polymerizable monomers.

The silicone-grafted styling polymers for use in the personal cleansing composition comprise "silicone-containing" (or "polysiloxane-containing") monomers, which form the silicone macromer pendant from the backbone, and non-silicone-containing monomers, which form the organic backbone of the polymer. That is a siloxane monomer grafted to the ha styling polymer.

Preferred silicone-grafted polymers comprise an organic backbone, preferably a carbon backbone derived from ethylenically unsaturated monomers, such as a vinyl polymeric backbone, and a polysiloxane macromer (especially preferred are polydialkylsiloxane, most preferably polydimethylsiloxane) grafted to the backbone. The polysiloxane macromer should have a weight average molecular weight of at least about 500, preferably from about 1,000 to about 100,000, more preferably from about 2,000 to about 50,000, most preferably about 5,000 to about 20,000. Organic backbones contemplated include those that are derived from polymerizable, ethylenically unsaturated monomers, including vinyl monomers, and other condensation monomers (e.g., those that polymerize to form polyamides and polyesters), ring-opening monomers (e.g., ethyl oxazoline and caprolactone), etc. Also contemplated are backbones based on cellulosic chains, ether-containing backbones, etc.

Preferred silicone grafted polymers for use in the personal cleansing composition comprise monomer units derived from: at least one free radically polymerizable ethylenically unsaturated monomer or monomers and at least one free radically polymerizable polysiloxane-containing ethylenically unsaturated monomer or monomers.

The silicone grafted polymers suitable for use in the personal cleansing composition generally comprise from about 1% to about 50%, by weight, of polysiloxane-containing monomer units and from about 50% to about 99% by weight, of non-polysiloxane-containing monomers. The non-polysiloxane-containing monomer units can be derived from the hydrophilic and/or hydrophobic monomer units described hereinbefore.

The styling polymer for use in the personal cleansing composition can therefore comprise combinations of the hydrophobic and/or polysiloxane-containing monomer units described herein, with or without hydrophilic comonomers as described herein, provided that the resulting styling polymer has the requisite characteristics as described herein.

Suitable polymerizable polysiloxane-containing monomers include, but are not limited to, those monomers that conform to the formula:

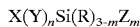

$$X(Y)_n Si(R)_{3-m} Z_m$$

wherein X is an ethylenically unsaturated group copolymerizable with the hydrophobic monomers described herein, such as a vinyl group; Y is a divalent linking group; R is a hydrogen, hydroxyl, lower alkyl (e.g. $C_1$–$C_4$), aryl, alkaryl, alkoxy, or alkylamino; Z is a monovalent siloxane polymeric moiety having a number average molecular weight of at least about 500, which is essentially unreactive under copolymerization conditions, and is pendant from the vinyl polymeric backbone described above; n is 0 or 1; and m is an integer from 1 to 3. These polymerizable polysiloxane-containing monomers have a weight average molecular weight as described above.

A preferred polysiloxane-containing monomer conforms to the formula:

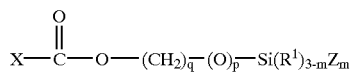

wherein m is 1, 2 or 3 (preferably m=1); p is 0 or 1; q is an integer from 2 to 6; $R^1$ is hydrogen, hydroxyl, lower alkyl, alkoxy, alkylamino, aryl, or alkaryl (preferably $R^1$ is alkyl); X conforms to the formula

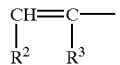

wherein $R^2$ is hydrogen or —COOH (preferably $R^2$ is hydrogen); $R^3$ is hydrogen, methyl or —CH$_2$COOH (preferably $R^3$ is methyl); Z conforms to the formula:

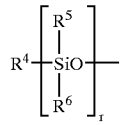

wherein $R^4$, $R^5$, and $R^6$ independently are lower alkyl, alkoxy, alkylamino, aryl, arylalkyl, hydrogen or hydroxyl (preferably $R^4$, $R^5$, and $R^6$ are alkyls); and r is an integer of about 5 or higher, preferably about 10 to about 1500 (most preferably r is from about 100 to about 250). Most preferably, $R^4$, $R^5$, and $R^6$ are methyl, p=0, and q=3.

Another preferred polysiloxane monomer conforms to either of the following formulas

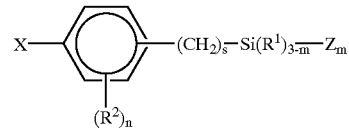

or

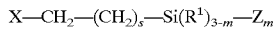

wherein: s is an integer from 0 to about 6, preferably 0, 1, or 2, more preferably 0 or 1; m is an integer from 1 to 3, preferably 1; $R^2$ is $C_1$–$C_{10}$ alkyl or $C_7$–$C_{10}$ alkylaryl, preferably $C_1$–$C_6$ alkyl or $C_7$–$C_{10}$ alkylaryl, more preferably $C_1$–$C_2$ alkyl; n is an integer from 0 to 4, preferably 0 or 1, more preferably 0.

The silicone grafted styling polymers suitable for use in the personal cleansing composition preferably comprise from about 50% to about 99%, more preferably from about 60% to about 98%, most preferably from about 75% to about 95%, by weight of the polymer, of non-silicone macromer-containing monomer units, e.g. the total hydrophobic and hydrophilic monomer units described herein, and from about 1% to about 50%, preferably from about 2% to about 40%, more preferably from about 5% to about 25%, of silicone macromer-containing monomer units, e.g. the polysiloxane-containing monomer units described herein. The level of hydrophilic monomer units can be from about 0% to about 70%, preferably from about 0% to about 50%, more preferably from about 0% to about 30%, most preferably from about 0% to about 15%; the level of hydrophobic monomer units, can be from 30% to about 99%, preferably from about 50% to about 98%, more preferably from about 70% to about 95%, most preferably from about 85% to about 95%.

Examples of some suitable silicone grafted polymers for use in the personal cleansing composition herein are listed below. Each listed polymer is followed by its monomer composition as weight part of monomer used in the synthesis:

(i) t-butylacrylatye/t-butyl-methacrylate/2-ethylhexyl-methacrylate/PDMS macromer-20,000 molecular weight macromer 31/27/32/10

(ii) t-butylmethacrylate/2-ethylhexyl-methacrylate/PDMS macromer-15,000 molecular weight macromer 75/10/15

(iii) t-butylmethacrylate/2-ethylhexyl-acrylate/PDMS macromer-10,000 molecular weight macromer 65/15/20

(iv) t-butylacrylate/2-ethylhexyl-acrylate/PDMS macromer-14,000 molecular weight macromer 77/11/12

(v) t-butylacrylate/2-ethylhexyl-methacrylate/PDMS macromer-13,000 molecular weight macromer 81/9/10

Examples of other suitable silicone grafted polymers for use in the personal cleansing composition of the present invention are described in EPO Application 90307528.1, published as EPO Application 0 408 311 A2 on Jan. 11, 1991, Hayama, et al.; U.S. Pat. No. 5,061,481, issued Oct. 29, 1991, Suzuki et al.; U.S. Pat. No. 5,106,609, Bolich et al., issued Apr. 21, 1992; U.S. Pat. No. 5,100,658, Bolich et al., issued Mar. 31, 1992; U.S. Pat. No. 5,100,657, Ansher-Jackson, et al., issued Mar. 31, 1992; U.S. Pat. No. 5,104, 646, Bolich et al., issued Apr. 14, 1992; U.S. Ser. No.

07/758,319, Bolich et al, filed Aug. 27, 1991, U.S. Ser. No. 07/758,320, Torgerson et al., filed Aug. 27, 1991, which descriptions are incorporated herein by reference.

Solvent—The personal cleansing composition used in the methods of the present invention must additionally comprise a volatile solvent for solubilizing the styling polymers, described hereinbefore, when such a styling polymer is present. The solvent helps disperse the styling polymer as water-insoluble fluid particles throughout the personal cleansing composition, wherein the dispersed particles comprise the styling polymer and the volatile solvent. Solvents suitable for this purpose include hydrocarbons, ethers, esters, amines, alkyl alcohols, volatile silicone derivatives and combinations thereof, many examples of which are well known in the art.

The volatile solvent must be water-insoluble or have a low water solubility. The selected styling polymer, however, must also be sufficiently soluble in the selected solvent to allow dispersion of the hair styling polymer and solvent combination as a separate, dispersed fluid phase in the personal cleansing composition.

The solvent suitable for use in the personal cleansing composition must also be a volatile material. In this context, the term volatile means that the solvent has a boiling point of less than about 300° C., preferably from about 90° C. to about 260° C., more preferably from about 100° C. to about 200° C. (at about one atmosphere of pressure).

The concentration of the volatile solvent in the personal cleansing composition must be sufficient to solubilize the hair styling polymer and disperse it as a separate fluid phase in the personal cleansing composition. Such concentrations generally range from about 0.10% to about 10%, preferably from about 0.5% to about 8%, most preferably from about 1% to about 6%, by weight of the personal cleansing composition, wherein the weight ratio of styling polymer to solvent is preferably from about 10:90 to about 70:30, more preferably from about 20:80 to about 65:35, even more preferably from about 30:70 to about 60:40. If the weight ratio of styling polymer to solvent is too low, the lathering performance of the personal cleansing composition is negatively affected. If the ratio of polymer to solvent is too high, the composition becomes too viscous and causes difficulty in the dispersion of the styling polymer. The hair styling agents should have an average particle diameter in the final personal cleansing product of from about 0.05 to about 100 microns, preferably from about 0.2 micron to about 25 microns. Particle size can be measured according to methods known in the art, including, for example optical microscopy.

Preferred volatile solvents for use in the personal cleansing composition are the hydrocarbon solvents, especially branched chain hydrocarbon solvents. The hydrocarbon solvents may be linear or branched, saturated or unsaturated, hydrocarbons having from about 8 to about 18 carbon atoms, preferably from about 10 to about 16 carbon atoms. Saturated hydrocarbons are preferred, as are branched hydrocarbons. Nonlimiting examples of some suitable linear hydrocarbons include decane, dodecane, decene, tridecene, and combinations thereof. Suitable branched hydrocarbons include isoparaffins, examples of which include commercially available isoparaffins from Exxon Chemical Company such as Isopar H and K ($C_{11}$–$C_{12}$ isoparaffins), and Isopar L ($C_{11}$–$C_{13}$ isoparaffins). Preferred branched hydrocarbons are isohexadecane, isododecane, 2,5-dimethyl decane, isotetradecane, and combinations thereof. Commercially available branched hydrocarbons include Permethyl 99A and 101A (available from Preperse, Inc., South Plainfield, N.J., USA).

Other suitable solvents include isopropanol, butyl alcohol, amyl alcohol, phenyl ethanol, benzyl alcohol, phenyl propanol, ethyl butyrate, isopropyl butyrate, diethyl phthalate, diethyl malonate, diethyl succinate, dimethyl malonate, dimethyl succinate, phenyl ethyl dimethyl carbinol, ethyl-6-acetoxyhexanoate, and methyl (2-pentanyl-3-oxy)cyclopentylacetate, and mixtures thereof. Preferred among such other suitable solvents are diethyl phthalate, diethyl malonate, diethyl succinate, dimethyl malonate, dimethyl succinate, phenylethyl dimethyl carbinol, ethyl-6-acetoxyhexanoate, and mixtures thereof.

Suitable ether solvents are the di($C_5$–$C_7$) alkyl ethers and diethers, especially the di($C_5$–$C_6$) alkyl ethers such as isoamyl ether, dipentyl ether and dihexyl ether.

Other suitable solvents for use in the personal cleansing composition the volatile silicon derivatives such as cyclic or linear polydialkylsiloxane, linear siloxy compounds or silane. The number of silicon atoms in the cyclic silicones is preferably from about 3 to about 7, more preferably about 3 to about 5.

The general formula for such silicones is:

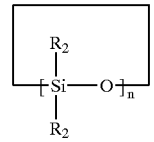

wherein $R_1$ and $R_2$ are independently selected from $C_1$ to $C_8$ alkyl, aryl or alkylaryl and wherein n=3–7. The linear polyorgano siloxanes have from about 2 to 7 silicon atoms and have the general formula:

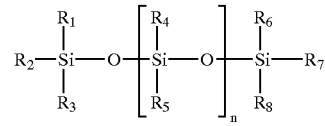

wherein $R_1$, $R_2$, $R_3$, $R_4$, $R_5$, $R_6$, $R_7$ and $R_8$ can independently be saturated or unsaturated $C_1$–$C_8$ alkyl, aryl, alkylaryl, hydroxyalkyl, amino alkyl or alkyl siloxy.

Linear siloxy compounds have the general formula:

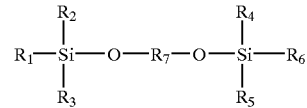

wherein $R_1$, $R_2$, $R_3$, $R_4$, $R_5$, and $R_6$ are independently selected from saturated or unsaturated $C_1$ to $C_7$ alkyl, aryl and alkyl aryl and $R_7$ is $C_1$ to $C_4$ alkylene.

Silane compounds have the general formula:

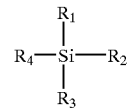

wherein $R_1$, $R_2$, $R_3$, and $R_4$ can independently be selected from $C_1$–$C_8$ alkyl, aryl, alkylaryl, hydroxyalkyl and alkylsiloxy.

Silicones of the above type, both cyclic and linear, are offered by Dow Corning Corporation, Dow Corning 344, 345 and 200 fluids, Union Carbide, Silicone 7202 and Silicone 7158, and Stauffer Chemical, SWS-03314.

The linear volatile silicones generally have viscosities of less than about 5 centistokes at 25° C. while the cyclic materials have viscosities less than about 10 centistokes. Examples of volatile silicones are described in Todd and Byers, "Volatile Silicone Fluids for Cosmetics", Cosmetics and Toiletries, Vol. 91, January, 1976, pp. 27–32, and also in Silicon Compounds, pages 253–295, distributed by Petrarch Chemicals, which descriptions are incorporated herein by reference.

Cationic Spreading Agent—The personal cleansing compositions used in the methods of the present invention may additionally comprise select cationic materials which act for use as spreading agents. The spreading agents for use in the composition are select quaternary ammonium or protonated amino compounds defined in greater detail hereinafter. These select spreading agents are useful to improve spreadability of the water-insoluble styling polymer on the body, for example on the hair. The concentration of the select spreading agents in the composition range from about 0.05% to about 5%, preferably from about 0.1% to about 2%, more preferably from about 0.2% to about 1%, by weight of the personal cleansing composition.

It has been found that the select spreading agents will improve spreadability of a water-insoluble styling polymer when used in the personal cleansing composition of the present invention. In particular, the improved insoluble solvent, water-insoluble styling polymer, and cationic deposition polymer, are especially effective at improving styling performance of the composition. The improved styling performance results from the improved spreading efficiency of water-insoluble styling polymer attributed to the use of the select spreading agent in the composition onto hair. This improved spreading results in improved styling performance, or allows for formulation of the personal cleansing composition using reduced amounts of styling polymer or cationic deposition polymer.

The select spreading agents are quaternary ammonium or amino compounds having 2, 3 or 4 N-radicals which are substituted or unsubstituted hydrocarbon chains having from about 12 to about 30 carbon atoms, wherein the substituents includes nonionic hydrophilic moieties selected from alkoxy, polyoxalkylene, alkylamido, hydroxyalkyl, alkylester moieties, and mixtures thereof. Suitable hydrophile-containing radicals include, for example, compounds having nonionic hydrophile moieties selected from the group consisting of ethoxy, propoxy, polyoxyethylene, polyoxypropylene, ethylamido, propylamido, hydroxymethyl, hydroxyethyl, hydroxypropyl, methylester, ethylester, propylester, or mixtures thereof. The select spreading agents are cationic and must be positively charged at the pH of the personal cleansing compositions. Generally, the pH of the personal cleansing composition will be less than about 10, typically from about 3 to about 9, preferably from about 4 to about 8.

Select cationic spreading agents for use in the composition include those corresponding to the to the formula:

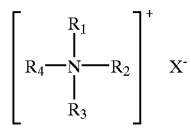

wherein $R_1$, and $R_2$ are independently a saturated or unsaturated, substituted or unsubstituted, linear or branched hydrocarbon chain having from about 12 to about 30 carbon atoms, preferably from about 18 to about 22 carbon atoms, and wherein the hydrocarbon chain can contain one or more hydrophilic moieties selected from the alkoxy, polyoxyalkylene, alkylamido, hydroxyalkyl, alkylester, and mixtures thereof; $R_3$ and $R_4$ are independently a hydrogen, or a saturated or unsaturated, substituted or unsubstituted, linear or branched hydrocarbon chain having from about 1 to about 30 carbon atoms, or a hydrocarbon having from about 1 to about 30 carbon atoms containing one or more aromatic, ester, ether, amido, amino moieties present as substitutents or as linkages in the chain, and wherein the hydrocarbon chain can contain one or more hydrophilic moieties selected from the alkoxy, polyoxyalkylene, alkylamido, hydroxyalkyl, alkylester, and mixtures thereof; and X is a soluble salt forming anion preferably selected from halogen (especially chlorine), acetate, phosphate, nitrate, sulfonate, and alkylsulfate radicals.

An example of a select spreading agent for use in the composition include those corresponding to the formula:

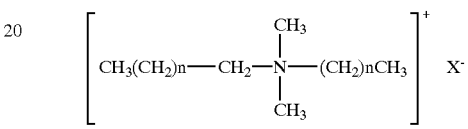

wherein n is from 10–28, preferably 16, and X is a water soluble salt forming anion (e.g., Cl, sulfate, etc.).

Other examples of select cationic spreading agents for use in the composition include those corresponding to the formula:

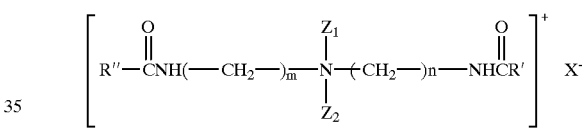

wherein $Z_1$ and $Z_2$ are independently saturated or unsaturated, substituted or unsubstituted, linear or branched hydrocarbons, and preferably $Z_1$ is an alkyl, more preferably methyl, and $Z_2$ is a short chain hydroxyalkyl, preferably hydroxymethyl or hydroxyethyl; n and m are independently integers from 1 to 4, inclusive, preferably from 2 to 3, inclusive, more preferably 2; R' and R" are independently substituted or unsubstituted hydrocarbons, preferably $C_{12}$–$C_{20}$ alkyl or alkenyl; and X is a soluble salt forming anion (e.g., Cl, sulfate, etc.).

Nonlimiting examples of suitable cationic spreading agents include ditallowdimethyl ammonium chloride, ditallowdimethyl ammonium methyl sulfate, dihexadecyl dimethyl ammonium chloride, di-(hydrogenated tallow) dimethyl ammonium chloride, dioctadecyl dimethyl ammonium chloride, dieicosyl dimethyl ammonium chloride, didocosyl dimethyl ammonium chloride, di-(hydrogenated tallow) dimethyl ammonium acetate, dihexadecyl dimethyl ammonium acetate, ditallow dipropyl ammonium phosphate, ditallow dimethyl ammonium nitrate, di-(coconutalkyl) dimethyl ammonium chloride, ditallowamidoethyl hydroxypropylmonium methosulfate (commercially available as Varisoft 238), dihydrogenated tallowamidoethyl hydroxyethylmonium methosulfate (commercially available as Varisoft 110), ditallowamidoethyl hydroxyethylmonium methosulfate (commercially available as Varisoft 222), and di(partially hardened soyoylethyl) hydroxyethylmonium methosulfate (commercially available as Armocare EQ-S). Ditallowdimethyl ammonium chloride, ditallowamidoethyl hydroxypropylmonium methosulfate, dihydrogenated tallowamidoethyl hydroxyethylmonium methosulfate, ditallowamidoethyl hydroxyethylmonium methosulfate, and di(partially hardened soyoylethyl)hydroxyethylmonium methosulfate are particularly preferred quaternary ammonium cationic surfactants useful herein.

Other suitable quaternary ammonium cationic surfactants are described in M.C. Publishing Co., *McCutcheion's Detergents & Emulsifiers*, (North American edition 1979); Schwartz, et al., *Surface Active Agents. Their Chemistry and Technology*, New York: Interscience Publishers, 1949; U.S. Pat. No. 3,155,591, to Hilfer, issued Nov. 3, 1964; U.S. Pat. No. 3,929,678 to Laughlin et al., issued Dec. 30, 1975; U.S. Pat. No. 3,959,461 to Bailey et al, issued May 25, 1976; and U.S. Pat. No. 4,387,090 to Bolich Jr., issued Jun. 7, 1983, which descriptions are incorporated herein by reference.

iii) Dispersed Phase Polymers

Another optional component of the personal cleansing compositions used in the methods of the present invention is a dispersed phase polymer. Suitable dispersed phase polymers include water soluble nonionic polymers and water soluble anionic polymers. Suitable nonionic polymers include cellulose ethers (e.g., hydroxybutyl methylcellulose, hydroxypropylcellulose, hydroxypropyl methylcellulose, ethylhydroxy ethylcellulose and hydroxyethylcellulose), propylene glycol alginates, polyacrylamide, poly(ethylene oxide), polyvinyl alcohol, polyvinylpyrrolidone, hydroxypropyl guar gum, locust bean gum, amylose, hydroxyethyl amylose, starch and starch derivatives and mixtures thereof. Preferred nonionic polymers include hydroxyethyl cellulose, polyethylene oxide, polyvinyl pyrrolidone, polyvinyl alcohol, polyacrylamide, hydroxypropyl cellulose, ethylhydroxyethyl cellulose, dextran, polypropyleneoxide and hydroxypropyl guar or mixtures thereof.

Suitable anionic water-soluble polymers include carboxymethyl cellulose, carrageenan, xanthum gum polystyrene sulfonate, gum agar, gum ghatti, gum karaya, pectins, alginate salts, as well as poly(acrylic acid) and acrylic or methacrylic acid derivatives such as the alkali metal and ammonium salts of acrylic acid, methacrylic acid. Mixtures of the above anionic water-soluble polymers may also be used.

These polymeric compositions may be homopolymers or they may be copolymers or terpolymers with other copolymerizing monomers known in the art. Examples of copolymerizing monomers known in the art include but are not limited to ethylene, propylene, isobutylene, styrene, polystyrene, alphamethylstyrene, vinyl acetate, vinyl formate, alkyl ethers, acrylonitrile, methacrylonitrile, vinyl chloride, vinylidene chloride, the alkyl acrylates, the alkylmethacrylates, the alkyl fumarates, the alkyl maleates, and other olefinic monomers copolymerizable therewith as long as the resulting polymers are water soluble and phase separate in the compositions of this invention. Copolymers of anionic and nonionic monomers such as acrylic acid and methacrylic acid with acrylamide, methacrylamide, the N-alkyl substituted amides, the N-aminoalkylamides, the corresponding N-alkylaminoalkyl substituted amides, the aminoalkyl acrylates, the aminoalkyl methacrylamides, and the N-alkyl substituted aminoalkyl esters of either acrylic or methacrylic acids.

Preferred anionic polymers include polyacrylic acid; sodium carboxy methyl cellulose; polyacrylates; polymethyl acrylate; polysulphates such as polyvinyl sulfate, polystyrene sulfonate, polyphosphates, sodium dextran sulfate, alginate salts and pectate.

When combined with the aqueous surfactant system and phase separation initiator, described below, the water-soluble nonionic or anionic polymer separates to form aqueous droplets suspended in a continuous aqueous phase. The number average particle size of the polymer droplets can be from 0.1 microns to about 10,000 microns, preferably from about 1.0 micron to about 5000 microns, most preferably from about 5 microns to about 1000 microns.

Most preferred for use in the present invention are ethyl hydroxyethyl cellulose, hydroxyethyl cellulose, hydroxypropyl guar and polystyrene sulfonate.

The herein described polymers are preferably present at a concentration level of above about 0.1%, more preferably from about 0.15% to about 10%, most preferably from about 0.2% to about 2%. Mixtures of the anionic and nonionic water-soluble polymers may also be used.

See also copending U.S. patent application Ser. No. 08/786,521, which is incorporated herein by reference.

The personal care compositions of the invention when a dispersed phase polymers is present preferably contain a phase separation initiator, defined herein after.

Phase Separation Initiators The compositions used in the methods of the present invention may additionally contain a phase separation initiator. By the term "phase separation initiators", as used herein, means electrolytes, amphiphiles or mixtures thereof capable of inducing phase separation when combined with compositions comprising a surfactant system and a nonionic or anionic water-soluble polymer.

By the term "amphiphile" as used herein, means, generally, substances which contain both hydrophilic and hydrophobic (lipophilic) groups. Amphiphiles preferred for use in the present invention are those which generally do not form micelles or liquid crystal phases and include, but are not limited to: amides of fatty acids; fatty alcohols; fatty esters, glycol mono- and di-esters of fatty acids; glyceryl esters.

Amides, including alkanol amides, are the condensation products of fatty acids with primary and secondary amines or alkanolamines to yield products of the general formula:

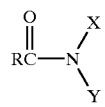

wherein RCO is a fatty acid radical and R is $C_{8-20}$; X is an alkyl, aromatic or alkanol ($CHR'CH_2OH$ wherein R' is H or $C_{1-6}$ alkyl); Y is H, alkyl, alkanol or X. Suitable amides include, but are not limited to, cocamide, lauramide, oleamide and stearamide. Suitable alkanolamides include, but are not limited to, cocamide DEA, cocamide MEA, cocamide MIPA, isostearamide DEA, isostearamide MEA, isostearamide MIPA, lanolinamide DEA, lauramide DEA, lauramide MEA, lauramide MIPA, linoleamide DEA, linoleamide MEA, linoleamide MIPA, myristamide DEA, myristamide MEA, myristamide MIPA, Oleamide DEA, Oleamide MEA, Oleamide MIPA, palmamide DEA, palmamide MEA, palmamide MIPA, palmitamide DEA, palmitamide MEA, palm kernelamide DEA, palm kernelamide MEA, palm kernelamide MIPA, peanutamide MEA, peanutamide MIPA, soyamide DEA, stearamide DEA, stearamide MEA, stearamide MIPA, tallamide DEA, tallowamide DEA, tallowamide MEA, undecylenamide DEA, undecylenamide MEA. The condensation reaction may be carried out with free fatty acids or with all types of esters of the fatty acids, such as fats and oils, and particularly methyl esters. The reaction conditions and the raw material sources determine the blend of materials in the end product and the nature of any impurities.

Fatty alcohols are higher molecular weight, nonvolatile, primary alcohols having the general formula:

wherein R is a $C_{8-20}$ alkyl. They can be produced from natural fats and oils by reduction of the fatty acid COOH— grouping to the hydroxyl function. Alternatively, identical or similarly structured fatty alcohols can be produced according to conventional synthetic methods known in the art. Suitable fatty alcohols include, but are not limited to, behenyl alcohol, $C_{9-11}$ alcohols, $C_{12-13}$ alcohols, $C_{12-15}$ alcohols, $C_{12-16}$ alcohols, $C_{14-15}$ alcohols, caprylic alcohol, cetearyl alcohol, coconut alcohol, decyl alcohol, isocetyl alcohol, isostearyl alcohol, lauryl alcohol, oleyl alcohol, palm kernel alcohol, stearyl alcohol, cetyl alcohol, tallow alcohol, tridecyl alcohol or myristyl alcohol.

Glyceryl esters comprise a subgroup of esters which are primarily fatty acid mono- and di-glycerides or triglycerides modified by reaction with other alcohols and the like. Preferred glyceryl esters are mono and diglycerides. Suitable glyceryl esters and derivatives thereof include, but are not limited to, acetylated hydrogenated tallow glyceride, glyceryl behenate, glyceryl caprate, glyceryl caprylate, glyceryl caprylate/caprate, glyceryl dilaurate, glyceryl dioleate, glyceryl erucate, glyceryl hydroxystearate, glyceryl isostearate, glyceryl lanolate, glyceryl laurate, glyceryl linoleate, glyceryl oleate, glyceryl stearate, glyceryl myristate, glyceryl distearate and mixtures thereof, Also useful as amphiphiles in the present invention are long chain glycol esters or mixtures thereof. Included are ethylene glycol esters of fatty acids having from about 8 to about 22 carbon atoms. Fatty esters of the formula RCO—OR' also act as suitable amphiphiles in the compositions of the present invention, where one of R and R' is a $C_{8-22}$ alkyl and the other is a $C_{1-3}$ alkyl.

The amphiphiles of the present invention may also encompass a variety of surface active compounds such as nonionic and cationic surfactants. If incorporated into the compositions of the present invention, these surface active compounds become additional surfactants used as amphiphiles for the purpose of initiating phase separation and are separate and apart from the surfactants of the surfactant system and the alkyl glyceryl sulfonate surfactant of the present invention.

Amphiphiles preferred for use herein include cocamide MEA, cetyl alcohol and stearyl alcohol.

The amphiphiles of the present invention are preferably present in the personal cleansing compositions at levels of from 0 to about 4%, preferably from about 0.5% to about 2%.

Suitable electrolytes include mono-, di- and trivalent inorganic salts as well as organic salts. Surfactant salts themselves are not included in the present electrolyte definition but other salts are. Suitable salts include, but are not limited to, phosphates, sulfates, nitrates, citrates and halides. The counter ions of such salts can be, but are not limited to, sodium, potassium, ammonium, magnesium or other mono-, di and tri valent cation. Electrolytes most preferred for use in the compositions of the present invention include sodium chloride, ammonium chloride, sodium citrate, and magnesium sulfate. It is recognized that these salts may serve as thickening aids or buffering aids in addition to their role as a phase separation initiator. The amount of the electrolyte used will generally depend on the amount of the amphiphile incorporated, but may be used at concentration levels of from about 0.1% to about 4%, preferably from about 0.2% to about 2%.

The amount of phase separation initiator comprising the electrolyte and/or the amphiphile will vary with the type of surfactant and polymer, but is generally present at a level of from about 0.1% to about 5%, preferably from about 0.2% to about 3%.

In view of the essential nature and activity of the phase separation initiators described above, the compositions of the present invention are, preferably, substantially free of materials which would prevent the induction or formation of separate, liquid phases. The term "substantially free", as used here, means that the compositions of the present invention contain no more than about 0.5% of such materials, preferably less than 0.25%, more preferably zero. Such materials typically include ethylene glycol, propylene glycol, ethyl alcohol and the like.

The compositions of the present invention are also preferably substantially free of other ingredients which unduly minimize the formation of separate and distinct liquid phases, especially ingredients which do not provide a significant benefit to the present invention.

c) Antidandruff Agent

The personal cleansing compositions used in the methods of the present invention can additionally comprise a safe and effective amount of an antidandruff agent. The antidandruff agent provides the personal cleansing compositions with antidandruff activity. The antidandruff agent is preferably a crystalline particulate that is insoluble in, and dispersed throughout, the personal cleansing compositions. Effective concentrations of such antidandruff agents generally range from about 0.1% to about 5%, more preferably from about 0.3% to about 5%, by weight of the personal cleansing compositions.

See also U.S. Pat. No. 4,948,576 to Verdicchio et al, and copending U.S. patent application Ser. No. 08/738,211, filed on Oct. 25, 1996, Ser. No. 08/622,222, filed on Mar. 27, 1996 and Ser. No. 08/593,727, all of which are incorporated herein by reference.

Suitable antidandruff agents includes, for example, platelet pyridinethione salt crystal, octopirox, selenium sulfide, ketoconazole and pyridinethione salts. Selenium sulfide is a preferred particulate antidandruff agent for use in the personal cleansing compositions, effective concentrations of which range from about 0.1% to about 5.0%, preferably from about 0.3% to about 2.5%, more preferably from about 0.5% to about 1.5%, by weight of the personal cleansing compositions. Selenium sulfide is generally regarded as a compound having one mole of selenium and two moles of sulfur, although it may also be a cyclic structure, $Se_xS_y$, wherein x+y=8. Average particle diameters for the selenium sulfide (selenium disulfide) are less than 15 um, preferably less than 10 um, as measured by forward laser light scattering device, e.g., Malvern 3600 instrument. Selenium sulfide compounds are well known in the personal cleansing art, and are described, for example in U.S. Pat. No. 2,694,668; U.S. Pat. No. 3,152,046; U.S. Pat. No. 4,089,945; and U.S. Pat. No. 4,885,107, which descriptions are incorporated herein by reference.

Pyridinethione antidandruff agents, especially 1-hydroxy-2-pyridinethione salts, are highly preferred particulate antidandruff agents for use in the personal cleansing compositions, concentrations of which range from about 0.1% to about 3%, preferably about 0.3% to about 2%, by weight of the personal cleansing compositions. Preferred pyridinethione salts are those formed from heavy metals such as zinc, tin, cadmium, magnesium, aluminum and zirconium. Zinc salts are most preferred, especially the zinc salt of 1-hydroxy-2-pyridinethione (zinc pyridinethione, ZPT). Other cations such as sodium may also be suitable.

Pyridinethione antidandruff agents are well known in the personal cleansing art, and are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982, which descriptions are incorporated herein by reference.

Sulfur may also be used as the particulate antidandruff agent in the personal cleansing compositions herein. Effective concentrations of the particulate sulfur are generally from about 1% to about 5%, more preferably from about 2% to about 5%, by weight of the compositions.

Octopirox and related salts and derivatives may also be used as the antidandruff agent in the personal cleansing compositions. Such antidandruff agents are soluble in the personal cleansing composition and, therefore, do not disperse throughout the composition as crystalline particulates as do the other antidandruff agents described hereinbefore. Other antidandruff agents such as azoles may also be used. Examples of azole antidandruff agents are: ketoconazole, itraconazole, fluconazole, miconazole, econazole.

Water soluble non-particulate antidandruff substances whose deposition and retention is enhanced by the water-soluble nitrogen containing polymers described herein include (i.e. deposition polymers).

(a) 1-hydroxy-2-pryidoner of the formula

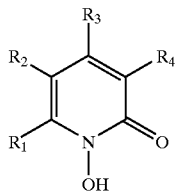

wherein $R_1$ is hydrogen, alkyl of 1 to 17 carbon atoms, cycloalkyl-alkyl of 1 to 4 alkyl carbon atoms, the cycloalkyl groups being optionally substituted by alkyl groups of 1 to 4 carbon atoms, aryl, aralkyl of 1 to 4 alkyl carbon atoms, aryl-alkenyl of 2 to 4 alkenyl carbon atoms, aryloxy-alkyl or arylthio-alkyl of 1 to 4 alkyl carbon atoms, benzhydryl, phenylsulfonyl-alkyl of 1 to 4 alkyl carbon atoms, furyl or furyl-alkenyl of 2 to 4 alkenyl carbon atoms, the aryl groups being optionally substituted by alkyl of 1 to 4 carbon atoms, by alkoxyl of 1 to 4 carbon atoms, by nitrogen, or cyano halogen atoms. $R_2$ is hydrogen, alkyl of 1 to 4 carbon atoms, alkenyl or alkinyl of 2 to 4 carbon atoms, halogen atoms or benzyl. $R_3$ is hydrogen, alkyl of 1 to 4 carbon atoms or phenyl. $R_4$ is hydrogen, alkyl of 1 to 4 carbon atoms, alkenyl of 2 to 4 carbon atoms, methoxy-methyl, halogen or benzyl and/or salts thereof.

These compounds are disclosed and more fully described in U.S. Pat. No. 4,185,106 and such compounds are available commercially from Hoechst Akitengeselfschaft under the trade name Octopirox.

(b) magnesium sulfate adducts of 2,2'-dithiobis(pyridine-1-oxide) of the formula

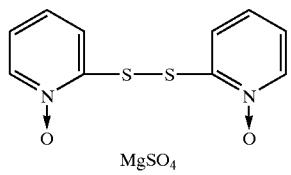

These compounds are available from Olin corporation under the trade name Omadine MDS.

It is preferred that an antidandruff agent be used in combination with a deposition polymer, where such a combination would result in improved deposition and retention of the antidandruff agent.

Additionally, the antidandruff agent can be a heavy metal magnesium or aluminium salts of 1-hydroxy-2-pyridinethione which has the following structural formula in tautomeric form, the sulfur being attached to the No. 2 position in the pyridine ring:

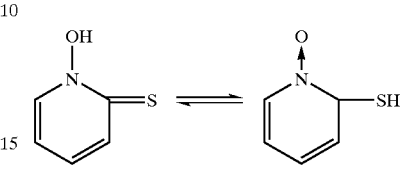

The metal salts represent substitution of the metal cation for the hydrogen of one of the tautomeric forms. Depending, of course, on the valence of the metal involved there may be more than one of the pyridinethione rings in the compound. Suitable heavy metals include zinc, tin, cadmium and zirconium.

The personal cleansing compositions of the invention can optionally contain a antidandruff agent which is a platelet pyridinethione salt crystal. When present, platelet pyridinethione salt crystals are predominantly flat platelets which have a mean sphericity less than about 0.65, preferably between about 0.20 and about 0.65 and a median size of at least about $2\mu$ diameter, expressed as the median equivalent diameter of a sphere of equal volume. It is preferred that the mean particle size be not greater than $15\mu$, measured on the same basis. The median diameters are on a mass basis with 50% of the mass of particles falling on either side of the value given.

The diameter of a sphere of equivalent volume for a particle can be determined by a varieties of sedimentation techniques which are based on Stokes' Law for the settling velocity of a partivle in a fluid. Such techniques are described in Stockham, J. D. and Fochtman, E. G., *Particle Size Analysis*, Ann Arbour Science, 1978, incorporated herein by reference.

The sphericity of a particle is also described by Stockham and Fochtman at page 113 as $$\psi = (d_v/d_s)^2$$

where $d_v$ is the diameter of a sphere of equivalent volume, supra, and $d_s$ is the diameter of a sphere of equivalent area. In the present invention the mean sphericity=$(-d_v/-d_s)^2$ or surface areas of spheres having equivalent volume distribution divided by the actual surface area of particles as measured. See U.S. Pat. No. 4,379,753 to Bolich, Jr incorporated herein by reference.

(d) Co-Surfactants

The surfactant system of the personal cleansing compositions used in the methods of the present invention can comprise, one or more detersive co-surfactants selected from the group consisting of anionic co-surfactant, nonionic co-surfactant, cationic co-surfactant, amphoteric co-surfactant, zwitterionic co-surfactants, and mixtures thereof. The total amount of surfactant present in the personal cleansing composition is preferably at least about 5%, more preferably still at least about 8%, even more preferably at least about 10%, by weight. Furthermore, the total amount of surfactant (i.e., the mid-chain branched surfactant plus co-surfactant) present in the personal cleansing composition will be present at preferably less than about 45%, more preferably less than about 35%, even more preferably less than about 30%, even more preferably less than about 25%, even more preferably less than about 20%, most preferably less than about 15%, by weight.

Anionic Co-surfactant—The personal cleansing compositions used in the methods herein preferably comprise an anionic co-surfactant, and preferably at concentrations of at least about 0.5%, more preferably, at least about 1%, even more preferably at least about 2%, even more preferably still at least about 5%, even more preferably still at least about 8%, most preferably at least about 10%, by weight. Furthermore, amount of anionic co-surfactant present in the personal cleansing composition will be present at preferably less than about 35%, more preferably less than about 30%, even more preferably less than about 25%, by weight of the composition. It is preferred that the total amount of anionic surfactant (i.e. anionic mid-chain branched plus anionic co-surfactant) present in the personal cleansing composition is preferably about 5% or greater, more preferably 8% or greater, even more preferably about 10% or greater, even more preferably still about 12% or greater, by weight of the composition.

Anionic co-surfactants for use in the personal cleansing compositions include alkyl and alkyl ether sulfates. These materials have the respective formulae $ROSO_3M$ and $RO(C_2H_4O)_xSO_3M$, wherein R is alkyl or alkenyl of from about 8 to about 30 carbon atoms, x is 1 to 10, and M is a cation such as ammonium, alkanolamines, such as triethanolamine, monovalent metals, such as sodium and potassium, and polyvalent metal cations, such as magnesium, and calcium. The cation M, of the anionic co-surfactant should be chosen such that the anionic co-surfactant component is water soluble. Solubility will depend upon the particular anionic co-surfactants and cations chosen.

Preferably, R has from about 12 to about 18 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil or tallow, or can be synthetic. Lauryl alcohol and straight chain alcohols derived from coconut oil are preferred herein. Such alcohols are reacted with between about 0 and about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the personal cleansing compositions of the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethyoxylation of from about 1 to about 4 moles of ethylene oxide.

Other suitable anionic co-surfactants are the water-soluble salts of organic, sulfuric acid reaction products of the general formula $[R_1\text{—}SO_3\text{—}M]$ where $R_1$ is selected from the group consisting of a straight or branched chain, saturated aliphatic hydrocarbon radical having from about 8 to about 24, preferably about 10 to about 18, carbon atoms; and M is a cation, as previously described, subject to the same limitations regarding polyvalent metal cations as previously discussed. Examples of such co-surfactants are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10-18}$ n-paraffins.

Still other suitable anionic co-surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other similar anionic co-surfactants are described in U.S. Pat. Nos. 2,486,921; 2,486,922; and 2,396,278.

Other anionic co-surfactants suitable for use in the personal cleansing compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; dioctyl esters of sodium sulfosuccinic acid.

Other suitable anionic co-surfactants include olefin sulfonates having about 10 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mixture of the above type is described more fully in the U.S. Pat. No. 3,332,880, which description is incorporated herein by reference.

Another class of anionic co-surfactants suitable for use in the personal cleansing compositions are the beta-alkyloxy alkane sulfonates. These compounds have the following formula:

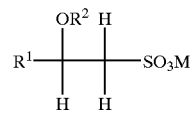

where $R^1$ is a straight chain alkyl group having from about 6 to about 20 carbon atoms, $R^2$ is a lower alkyl group having from about 1 (preferred) to about 3 carbon atoms, and M is a water-soluble cation as hereinbefore described.

Many other anionic co-surfactants suitable for use in the personal cleansing compositions are described in *McCutcheon's, Emulsifiers and Detergents*, 1989 *Annual*, published by M. C. Publishing Co., and in U.S. Pat. No. 3,929,678, which descriptions are incorporated herein by reference.

Preferred anionic co-surfactants for use in the personal cleansing compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric and zwitterionic co-surfactants—The detersive co-surfactant of the personal cleansing compositions used in the methods herein may comprise an amphoteric and/or zwitterionic co-surfactant. Concentrations of such co-surfactants will generally range from about 0.5% to about 20%, preferably from about 1% to about 10%, by weight of the personal cleansing compositions.

Amphoteric co-surfactants for use in the personal cleansing compositions include the derivatives of aliphatic secondary and tertiary amines in which the aliphatic radical is straight or branched and one of the aliphatic substituents contains from about 8 to about 18 carbon atoms and one contains an anionic water solubilizing group, e.g., carboxy, sulfonate, sulfate, phosphate, or phosphonate.

Suitable amphoteric co-surfactants for use in the personal cleansing compositions include long chain tertiary amine oxides of the formula $[R^1R^2R^3N \rightarrow O]$ where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals.

Suitable amphoteric co-surfactants for use in the personal cleansing compositions include long chain tertiary phosphine oxides of the formula $[RR'R'' P \rightarrow O]$ where R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R'' are each alkyl or monohydroxyalkyl groups containing from about 1 to about 3 carbon atoms.

Suitable amphoteric co-surfactants for use in the personal cleansing compositions include long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety.

Zwitterionic co-surfactants for use in the personal cleansing compositions include the derivatives of aliphatic quaternary ammonium, phosphonium, and sulfonium compounds, in which the aliphatic radicals are straight or branched, and wherein one of the aliphatic substituents contains from about 8 to about 18 carbon atoms and one contains an anionic group, e.g., carboxy, sulfonate, sulfate, phosphate, or phosphonate. A general formula for these compounds is:

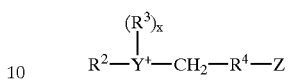

where $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of amphoteric and zwitterionic co-surfactants also include sultaines and amidosultaines. Sultaines and amidosultaines can be used as foam enhancing co-surfactants that are mild to the eye in partial replacement of anionic co-surfactants. Sultaines, including amidosultaines, include for example, cocodimethylpropylsultaine, stearyldimethylpropylsultaine, lauryl-bis-(2-hydroxyethyl)propylsultaine and the like; and the amidosultaines such as cocoamidodimethylpropylsultaine, stearylamidododimethylpropylsultaine, laurylamidobis-(2-hydroxyethyl) propylsultaine, and the like. Preferred are amidohydroxysultaines such as the $C_{12}$–$C_{18}$ hydrocarbyl amidopropyl hydroxysultaines, especially $C_{12}$–$C_{14}$ hydrocarbyl amido propyl hydroxysultaines, e.g., laurylamidopropyl hydroxysultaine and cocamidopropyl hydroxysultaine. Other sultaines are described in U.S. Pat. No. 3,950,417, which descriptions are incorporated herein by reference.

Other suitable amphoteric co-surfactants are the aminoalkanoates of the formula R—NH($CH_2$)$_n$COOM, the iminodialkanoates of the formula R—N[($CH_2$)$_m$COOM]$_2$ and mixtures thereof, wherein n and m are numbers from 1 to 4, R is $C_8$–$C_{22}$ alkyl or alkenyl, and M is hydrogen, alkali metal, alkaline earth metal, ammonium or alkanolammonium.

Examples of suitable aminoalkanoates include n-alkylamino-propionates and n-alkyliminodipropionates, specific examples of which include N-lauryl-beta-amino propionic acid or salts thereof, and N-lauryl-beta-iminodipropionic acid or salts thereof, and mixtures thereof.

Other suitable amphoteric co-surfactants include those represented by the formula:

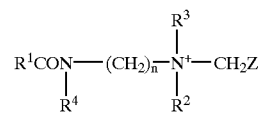

wherein $R^1$ is $C_8$–$C_{22}$ alkyl or alkenyl, preferably $C_{12}$–$C_{16}$, $R^2$ is hydrogen or $CH_2CO_2M$, $R^3$ is $CH_2CH_2OH$ or $CH_2CH_2OCH_2CH_2COOM$, $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation, such as alkali metal (e.g., lithium, sodium, potassium), alkaline earth metal (beryllium, magnesium, calcium, strontium, barium), or ammonium. This type of co-surfactant is sometimes classified as an imidazoline-type amphoteric co-surfactant, although it should be recognized that it does not necessarily have to be derived, directly or indirectly, through an imidazoline intermediate.

Suitable materials of this type are marketed under the trade name MIRANOL and are understood to comprise a complex mixture of species, and can exist in protonated and non-protonated species depending upon pH with respect to species that can have a hydrogen at $R^2$. All such variations and species are meant to be encompassed by the above formula.

Examples of co-surfactants of the above formula are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Commercial amphoteric co-surfactants include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Betaine co-surfactants (zwitterionic) suitable for use in the personal cleansing compositions are those represented by the formula:

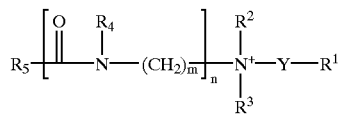

wherein:
$R_1$ is a member selected from the group consisting of

COOM and CH(OH)—CH$_2$SO$_3$M $R_2$ is lower alkyl or hydroxyalkyl;
$R_3$ is lower alkyl or hydroxyalkyl;
$R_4$ is a member selected from the group consisting of hydrogen and lower alkyl;
$R_5$ is higher alkyl or alkenyl;
Y is lower alkyl, preferably methyl;
m is an integer from 2 to 7, preferably from 2 to 3;
n is the integer 1 or 0;
M is hydrogen or a cation, as previously described, such as an alkali metal, alkaline earth metal, or ammonium.

The term "lower alkyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like. It should be understood that the term "higher alkyl or alkenyl" includes mixtures of radicals which may contain one or more intermediate linkages such as ether or polyether linkages or non-functional substituents such as hydroxyl or halogen radicals wherein the radical remains of hydrophobic character.

Examples of co-surfactant betaines of the above formula wherein n is zero which are useful herein include the alkylbetaines such as cocodimethylcarboxymethylbetaine, lauryldimethylcarboxymethylbetaine, lauryl dimethyl-alpha-carboxyethylbetaine, cetyldimethylcarboxymethylbetaine, lauryl-bis-(2-hydroxyethyl) carboxymethylbetaine, stearyl-bis-(2-hydroxypropyl) carboxymethylbetaine, oleyldimethyl-gamma-carboxypropylbetaine, lauryl-bis-(2-hydroxypropyl)alpha-carboxyethylbetaine, etc. The sulfobetaines may be represented by cocodimethylsulfopropylbetaine, stearyldimethylsulfopropylbetaine, lauryl-bis-(2-hydroxyethyl)sulfopropylbetaine, and the like.

Specific examples of amido betaines and amidosulfo betaines useful in the personal cleansing compositions include the amidocarboxybetaines, such as cocoamidodimethylcarboxymethylbetaine, laurylamidodimethylcarboxymethylbetaine, cetylamidodimethylcarboxymethylbetaine, laurylamido-bis-(2-hydroxyethyl)-carboxymethylbetaine, cocoamido-bis-(2-hydroxyethyl)-carboxymethylbetaine, etc. The amido sulfobetaines may be represented by cocoamidodimethyl- sulfopropylbetaine, stearylamidodimethylsulfopropyl- betaine, laurylamido-bis-(2-hydroxyethyl)-sulfopropylbetaine, and the like.

Nonionic co-surfactant—The personal cleansing compositions used in the methods of the present invention may comprise a nonionic co-surfactant as the detersive co-surfactant component therein. Nonionic co-surfactants include those compounds produced by condensation of alkylene oxide groups (hydrophilic in nature) with an organic hydrophobic compound, which may be aliphatic or alkyl aromatic in nature.

Concentrations of such co-surfactants will generally range from about 0.01% to about 20%, preferably from about 1% to about 10%, by weight of the personal cleansing compositions.

Preferred nonionic co-surfactants for use in the personal cleansing compositions include the following:

(1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products;

(3) condensation products of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;

(4) alkyl polysaccharide (APS) co-surfactants (e.g. alkyl polyglycosides), examples of which are described in U.S. Pat. No. 4,565,647, which description is incorporated herein by reference, and which discloses APS co-surfactants having a hydrophobic group with about 6 to about 30 carbon atoms and polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); and (5) polyethylene glycol (PEG) glyceryl fatty esters, such as those of the formula $R(O)OCH^2CH(OH)CH^2(OCH^2CH^2)_nOH$ wherein n is from about 5 to about 200, preferably from about 20 to about 100, and R is an aliphatic hydrocarbyl having from about 8 to about 20 carbon atoms.

Cationic Co-surfactants—Optional cationic co-surfactants for use as conditioning agents in the methods of the present invention will typically contain quaternary nitrogen moieties. Examples of suitable cationic co-surfactants are described in following documents, all of which are incorporated by reference herein in their entirety: M.C. Publishing Co., McCutcheon's, Detergents & Emulsifiers, (North American edition 1979); Schwartz, et al., Surface Active Agents, Their Chemistry and Technology, New York: Interscience Publishers, 1949; U.S. Pat. No. 3,155,591; U.S. Pat. No. 3,929,678; U.S. Pat. No. 3,959,461 and U.S. Pat. No. 4,387,090.

Concentrations of such co-surfactants will generally range from about 0.01% to about 20%, preferably from about 1% to about 10%, by weight of the personal cleansing compositions.

Examples of suitable cationic co-surfactants are those corresponding to the general formula:

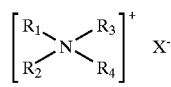

wherein $R_1$, $R_2$, $R_3$, and $R_4$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate nitrate, sulfate, and alkylsulfate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R_1$, $R_2$, $R_3$, and $R_4$ are independently selected from C1 to about C22 alkyl. Especially preferred are cationic materials containing two long alkyl chains and two short alkyl chains or those containing one long alkyl chain and three short alkyl chains. The long alkyl chains in the compounds described in the previous sentence have from about 12 to about 22 carbon atoms, preferably from about 16 to about 22 carbon atoms, and the short alkyl chains in the compounds described in the previous sentence have from 1 to about 3 carbon atoms, preferably from 1 to about 2 carbon atoms.

Form of Personal Cleansing Composition

The personal cleansing compositions used in the methods herein may be of an conventional form. That is, they can be liquids, gels, mousses, solids, bars, pastes and the like. The physical form will be selected depending upon the desired properties and the intended use of the composition.

Aqueous Liquid Carrier

The personal cleansing compositions used in the methods herein may further contain from about 50% to 99.899%, preferably from about 60% to about 95%, more preferably from about 70% to about 85%, by weight of an aqueous liquid carrier in which the other essential and optional compositions components are dissolved, dispersed or suspended.

One essential component of the aqueous liquid carrier is, of course, water. The aqueous liquid carrier, however, may contain other materials which are liquid, or which dissolve in the liquid carrier, at room temperature and which may also serve some other function besides that of a simple filler. Such materials can include, for example, hydrotropes and co-solvents.

Hydrotropes—The aqueous liquid carrier may comprise one or more materials which are hydrotropes. Hydrotropes suitable for use in the compositions herein include the $C_1$–$C_3$ alkyl aryl sulfonates, $C_6$–$C_{12}$ alkanols, $C_1$–$C_6$ carboxylic sulfates and sulfonates, urea, $C_1$–$C_6$ hydrocarboxylates, $C_1$–$C_4$ carboxylates, $C_2$–$C_4$ organic diacids and mixtures of these hydrotrope materials.

Suitable $C_1$–$C_3$ alkyl aryl sulfonates include sodium, potassium, calcium and ammonium xylene sulfonates; sodium, potassium, calcium and ammonium toluene sulfonates; sodium, potassium, calcium and ammonium cumene sulfonates; and sodium, potassium, calcium and ammonium substituted or unsubstituted naphthalene sulfonates and mixtures thereof.

Suitable $C_1$–$C_8$ carboxylic sulfate or sulfonate salts are any water soluble salts or organic compounds comprising 1 to 8 carbon atoms (exclusive of substituent groups), which are substituted with sulfate or sulfonate and have at least one carboxylic group. The substituted organic compound may be cyclic, acylic or aromatic, i.e. benzene derivatives. Preferred alkyl compounds have from 1 to 4 carbon atoms substituted with sulfate or sulfonate and have from 1 to 2 carboxylic groups. Examples of this type of hydrotrope include sulfosuccinate salts, sulfophthalic salts, sulfoacetic salts, m-sulfobenzoic acid salts and diester sulfosuccinates, preferably the sodium or potassium salts as disclosed in U.S. Pat. No. 3,915,903.

Suitable $C_1$–$C_4$ hydrocarboxylates and $C_1$–$C_4$ carboxylates for use herein include acetates and propionates and citrates. Suitable $C_2$–$C_4$ diacids for use herein include succinic, glutaric and adipic acids.

Other compounds which deliver hydrotropic effects suitable for use herein as a hydrotrope include $C_6$–$C_{12}$ alkanols and urea.

Preferred hydrotropes for use herein are sodium, potassium, calcium and ammonium cumene sulfonate; sodium, potassium, calcium and ammonium xylene sulfonate; sodium, potassium, calcium and ammonium toluene sulfonate and mixtures thereof. Most preferred are sodium cumene sulfonate and sodium xylene sulfonate and mixtures thereof. These preferred hydrotrope materials can be present in the composition to the extent of from about 0.1% to 8% by weight.

Co-Solvents—A variety of water-miscible liquids such as lower alkanols, diols, other polyols, ethers, amines, and the like may be used as part of the aqueous liquid carrier. Particularly preferred are the $C_1$–$C_4$ alkanols. Such co-solvents can be present in the compositions herein to the extent of up to about 8%. These co-solvents are different to the solvents used in combination with styling polymers as the co-solvents dissolved, dispersed or suspended any or all of the components of the personal cleansing compositions. Whereas, the solvent is concerned with only dispersing, and preferably dissolving, the styling polymer.

Optional Components

The personal cleansing compositions used in the methods of the present invention may further comprise one or more optional components known for use in shampoo, conditioning and other personal cleansing compositions, provided that the optional components are physically and chemically compatible with the essential component described herein, or do not otherwise unduly impair product stability, aesthetics or performance. Concentrations of such optional components typically range from about 0.001% to about 30% by weight of the personal cleansing compositions, when present.

Optional components include anti static agents, dyes, diluents, emollient oils (such as polyisobutylene, mineral oil, petrolatum and isocetyl stearyl stearate), pearlescent aids, foam boosters, pediculocides, pH adjusting agents, perfumes, preservatives, proteins, antioxidants; chelators and sequestrants; and aesthetic components such as fragrances, colorings, essential oils, skin sensates, astringents, skin soothing agents, skin healing agents and the like, nonlimiting examples of these aesthetic components include panthenol and derivatives (e.g. ethyl panthenol), pantothenic acid and its derivatives, clove oil, menthol, camphor, eucalyptus oil, eugenol, menthyl lactate, witch hazel distillate, allantoin, bisabalol, dipotassium glycyrrhizinate and the like, sunscreens, thickeners, vitamins and derivatives thereof (e.g., ascorbic acid, vitamin E, tocopheryl acetate, retinoic acid, retinol, retinoids, and the like), and viscosity adjusting agents. This list of optional components is not meant to be exclusive, and other optional components can be used.

Laundry Bars

The compositions used in the methods of the present invention may also be in the form of Laundry bars. That is, the compositions are designed for use in hand washing of fabrics and is in the form of a bar.

Detergent surfactant—Laundry bars used in the methods of the present invention typically comprise 10% to about 60%, preferably about 15% to about 40% of an anionic surfactant. A preferred anionic surfactant for use is an alkyl sulfate (AS) having an alkyl chain of from 10 to 20 carbon atoms, a branched-chain alkylbenzene sulfonate (ABS) having an alkyl chain of from 10 to 22 carbon atoms, a linear-chain alkylbenzene sulfonate (LAS) having an alkyl chain of from 10 to 22 carbon atoms, and mixtures thereof.

The alkyl portion of said ABS or LAS surfactant preferably contains from 10 to 16 carbon atoms, more preferably from 10 to 14 carbon atoms. Most preferably, the alkylbenzene sulfonate surfactant is LAS.

The alkyl portion of the AS surfactant preferably contains from 10 to 18 carbon atoms, more preferably from 12 to 16 carbon atoms. The AS surfactant can comprise a mixture of a longer-chain AS, such as one having 16 to 18 carbons, and a shorter-chain alkyl such as one having 11–13 carbons. Preferred AS surfactants include coconut alkyl sulfate, tallow alkylsulfate, and mixtures thereof; most preferably, coconut alkyl sulfate. A preferred anionic surfactant comprises a mixture of AS and alkylbenzene sulfonate. Also preferred are mixtures of AS and LAS surfacants at a ratio of AS:LAS of about 0:100 to 100:0.

The cation for the ABS, LAS and the AS is preferably sodium, although other useful cations include triethanolamine, potassium, ammonium, magnesium, and calcium, or mixtures thereof.

Other optional surfactants include zwitterionic, nonionic, amphoteric surfactants alone or in conjuction with anionic surfactants.

Detergent Builder—The laundry bars used in the methods of the present invention comprise from about 5% to about 60% by weight detergent builder. Preferred laundry bars comprise from about 5% to about 30% builder, more preferably from about 7% to about 20%, by weight of the bar. These detergent builders can be, for example, water-soluble alkali-metal salts of phosphates, pyrophosphates, orthophosphates, tripolyphosphates, higher polyphosphates, and mixtures thereof. A preferred builder is a water-soluble alkali-metal salt of tripolyphosphate, and a mixture of tripolyphosphate and pyrophosphate. The builder can also be a non-phosphate detergent builder. Specific examples of a non-phosphorous, inorganic detergency builder include water-soluble inorganic carbonate and bicarbonate salts. The alkali metal (e.g., sodium and potassium) carbonates, bicarbonates, and silicates are particularly useful herein. Specific preferred examples of builders include sodium tripolyphosphates (STPP) and sodium pyrophosphates (TSPP), and mixtures thereof. Other specifically preferred examples of builders include zeolite and polycarboxylates.

Sodium carbonate is a particularly preferred ingredient in laundry bars, since in addition to its use as a builder, it can also provide alkalinity to the laundry bar for improved detergency, and also can serve as a neutralizing agent for acidic components added in the bar processing. Sodium carbonate is particularly preferred as a neutralizing inorganic salt for an acid precursor of an anionic surfactant used in such laundry bars, such as the alkyl sulfuric acid and alkyl benzene sulfonic acid.

Co-polymers of acrylic acid and maleic acid are preferred as auxiliary builders, since it has been observed that their use in combination with the fabric softening clay and the clay flocculating agent further stabilizes and improves the clay deposition and fabric softening performance.

Optional Laundry Bar Componet

Auxiliary Surfactants—The detergent bars used in the methods of the present invention can contain up to about 70% by weight of optional ingredients commonly used in detergent products. A typical listing of the classes and species optional surfactants, optional builders and other ingredients useful herein appears in U.S. Pat. No. 3,664,961, issued to Norris on May 23, 1972, and EP 550,652, published on Apr. 16, 1992, incorporated herein by reference. The following are representative of such materials, but are not intended to be limiting.

In addition to the auxiliary surfactants mentioned above, a hydrotrope, or mixture of hydrotropes, can be present in the laundry detergent bar. Preferred hydrotropes include the alkali metal, preferably sodium, salts of tolune sulfonate, xylene sulfonate, cumene sulfonate, sulfosuccinate, and mixtures thereof. Preferably, the hydrotrope, in either the acid form or the salt form, and being substantially anhydrous, is added to the linear alkyl benzene sulfonic acid prior to its neutralization. The hydrotrope will preferably be present at from about 0.5% to about 5% of the laundry detergent bar.

Fabric Softening Clay—The fabric softening clay is preferably a smectite-type clay. The smectite-type clays can be described as expandable, three-layer clays; i.e., aluminosilicates and magnesium silicates, having an ion exchange capacity of at least about 50 meq/100 g. of clay. Preferably the clay particles are of a size that they can not be perceived tactilely, so as not to have a gritty feel on the treated fabric of the clothes. The fabric softening clay can be added to the bar to provide about 1% to about 30% by weight of the bar, more preferably from about 5% to about 20%, and most preferably about 8% to 14%.

While any of the smectite-type clays described herein are useful in the present invention, certain clays are preferred. For example, Gelwhite GP is an extremely white form of smectite-type clay and is therefore preferred when formulating white granular detergent compositions. Volclay BC, which is a smectite-type clay mineral containing at least 3% iron (expressed as $Fe_2O_3$) in the crystal lattice, and which has a very high ion exchange capacity, is one of the most efficient and effective clays for use in the instant compositions from the standpoint of product performance. On the other hand, certain smectite-type clays are sufficiently contaminated by other silicate minerals that their ion exchange capacities fall below the requisite range; such clays are of no use in the instant compositions.

Clay Flocculating Agent—It has been found that the use of a clay flocculating agent in a laundry bar containing softening clay provides surprisingly improved softening clay deposition onto the clothes and clothes softening performance, compared to that of laundry bars comprising softening clay alone. The polymeric clay flocculating agent is selected to provide improved deposition of the fabric softening clay. Typically such materials have a high molecular weight, greater than about 100,000. Examples of such materials can include long chain polymers and copolymers derived from monomers such as ethylene oxide, acrylamide, acrylic acid, dimethylamino ethyl methacrylate, vinyl alcohol, vinyl pyrrolidone, and ethylene imine. Gums, like guar gums, are suitable as well. The preferred clay flocculating agent is a poly(ethylene oxide) polymer.

Other Optional Ingredients—A particularly preferred optional component of the laundry bars used in the methods present invention is a detergent chelant. Such chelants are able to sequester and chelate alkali cations (such as sodium, lithium and potassium), alkali metal earth cations (such as magnesium and calcium), and most preferably, heavy metal cations such as iron, manganese, zinc and aluminum. Preferred cations include sodium, magnesium, zinc, and mixtures thereof. The detergent chelant is particularly beneficial for maintaining good cleaning performance and improved surfactant mileage, despite the presence of the softening clay and the clay flocculating agent.

The detergent chelant is preferably a phosphonate chelant, particular one selected from the group consisting of diethylenetriamine penta(methylene phosphonic acid), ethylene diamine tetra(methylene phosphonic acid), and mixtures and salts and complexes thereof, and an acetate chelant, particularly one selected from the group consisting of diethylenetriamine penta(acetic acid), ethylene diamine tetra(acetic acid), and mixtures and salts and complexes thereof. Particularly preferred are sodium, zinc, magnesium, and aluminum salts and complexes of diethylenetriamine penta (methylene phosphonate) diethylenetriamine penta (acetate), and mixtures thereof.

Preferably such salts or complexes have a molar ratio of metal ion to chelant molecule of at least 1:1, preferably at least 2:1.

The detergent chelant can be included in the laundry bar at a level up to about 5%, preferably from about 0.1% to about 3%, more preferably from about 0.2% to about 2%, most preferably from about 0.5% to about 1.0%. Such detergent chelant component can be used beneficially to improve the surfactant mileage of the present laundry bar, meaning that for a given level of anionic surfactant and level of detergent chelant, equivalent sudsing and cleaning performance can be achieved compared to a similar bar containing a higher level of the anionic surfactant but without the detergent chelant.

Another preferred additional component of the laundry bar is fatty alcohol having an alkyl chain of 8 to 22 carbon atoms, more preferably from 12 to 18 carbon atoms. Fatty alcohol is effective at reducing the bar wear rate and smear (mushiness) of the present laundry bars. A preferred fatty alcohol has an alkyl chain predominantly containing from 16 to 18 carbon atoms, so-called "high-cut fatty alcohol," which can exhibit less base odor of fatty alcohol relative to broad cut fatty alcohols. Typically fatty alcohol is contained in the laundry bar at up to a level of 10%, more preferably from about 0.75% to about 6%, most preferably from about 2% to about 5%. The fatty alcohol is generally added to the formulation of the present invention as free fatty alcohol. However, low levels of fatty alcohol can be introduced into the bars as impurities or as unreacted starting material. For example, laundry bars based on coconut fatty alkyl sulfate can contain, as unreacted starting material, from 0.1% to 3.5%, more typically from 2% to 3%, by weight of free coconut fatty alcohol on a coconut fatty alkyl sulfate basis.

Another preferred optional component in the laundry bar is a dye transfer inhibiting (DTI) ingredient to prevent diminishing of color fidelity and intensity in fabrics. A preferred DTI ingredient can include polymeric DTI materials capable of binding fugitives dyes to prevent them from depositing on the fabrics, and decolorization DTI materials capable of decolorizing the fugitives dye by oxidation. An example of a decolorization DTI is hydrogen peroxide or a source of hydrogen peroxide, such as percarbonate or perborate. Non-limiting examples of polymeric DTI materials include polyvinylpyrridine N-oxide, polyvinylpyrrolidone (PVP), PVP-polyvinylimidazole copolymer, and mixtures thereof. Copolymers of N-vinylpyrrolidone and N-vinylimidazole polymers (referred to as "PVPI") are also preferred for use herein.

Another preferred optional component in the laundry bar is a secondary fabric softener component in addition to the softening clay. Such materials can be used at levels of about 0.1% to 5%, more preferably from 0.3% to 3%, and can include: amines of the formula $R_4R_5R_6N$, wherein $R_4$ is $C_5$ to $C_{22}$ hydrocarbyl, $R_5$ and $R_6$ are independently $C_1$ to $C_{10}$ hydrocarbyl. One preferred amine is ditallowmethyl amine; complexes of such amines with fatty acid of the formula $R_7COOH$, wherein $R_7$ is $C_9$ to $C_{22}$ hydrocarbyl, as disclosed in EP No. 0,133,804; complexes of such amines with phosphate esters of the formula $R_8O—P(O)(OH)—OR_9$ and $HO—P(O)(OH)—OR_9$, wherein $R_8$ and $R_9$ are independently $C_1$ to $C_{20}$ alkyl of alkyl ethoxylate of the formula -alkyl-$(OCH_2CH_2)$; cyclic amines such as imidazolines of the general formula 1-(higher alkyl)amido (lower alkyl)-2-(higher alkyl)imidazoline, where higher alkyl is from 12 to 22 carbons and lower alkyl is from 1 to 4 carbons, such as described in UK Patent Application GB 2,173,827; and quaternary ammonium compounds of the formula $R_{10}R_{11}R_{12}R_{13}N^+X^-$, wherein $R_{10}$ is alkyl having 8 to 20 carbons, $R_{11}$ is alkyl having 1 to 10 carbons, $R_{12}$ and $R_{13}$ are alkyl having 1 to 4 carbons, preferably methyl, and X is an anion, preferably Cl⁻ or Br⁻, such as $C_{12-13}$ alkyl trimethyl ammonium chloride.

Yet another optional component in the laundry bar is a bleach component. The bleaching component can be a source of —OOH group, such as sodium perborate monohydrate, sodium perborate tetrahydrate and sodium percarbonate. Sodium percarbonate ($2Na_2CO_3 \cdot 3H_2O_2$) is preferred since it has a dual function of both a source of HOOH and a source of sodium carbonate.

Another optional bleaching component is a peracid per se, such as a formula:

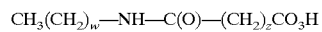

wherein z is from 2 to 4 and w is from 4 to 10. (The compound of the latter formula where z is 4 and w is 8 is hereinafter referred to as NAPAA.) The bleaching component can contain, as a bleaching component stabilizer, a chelating agent of polyaminocarboxylic acids, polyaminocarboxylates such as ethylenediaminotetraacetic acid, diethylenetriaminopentaacetic acid, and ethylenediaminodisuccinic acid, and their salts with water-soluble alkali metals. The bleach components can be added to the bar at a level up to 20%, preferably from about 1% to about 10%, more preferably from about 2% to about 6%.

Sodium sulfate is a well-known filler that is compatible with the compositions of this invention. It can be a by-product of the surfactant sulfation and sulfonation processes, or it can be added separately.

Calcium carbonate (also known as Calcarb) is also a well known and often used component of laundry bars. Such materials are typically used at levels up to 40%, preferably from about 5% to about 25%.

Binding agents for holding the bar together in a cohesive, soluble form can also be used, and include natural and synthetic starches, gums, thickeners, and mixtures thereof.

Soil suspending agents can be used. In the present invention, their use is balanced with the fabric softening clay/clay flocculating agent combination to provide optimum cleaning and fabric softening performance. Soil suspending agents can also include water-soluble salts of carboxymethylcellulose and carboxyhydroxy-methylcellulose. A preferred soil suspending agent is an acrylic/maleic copolymer, commercially available as Sokolan®, from BASF Corp. Other soil suspending agents include polyethylene glycols having a molecular weight of about 400 to 10,000, and ethoxylated mono- and polyamines, and quaternary salts thereof.

Optical brighteners are also preferred optional ingredients in laundry bars of the present invention. Preferred optical brighteners are diamino stilbene, distyrilbiphenyl-type optical brighteners. Preferred as examples of such brighteners are 4,4'-bis {[4-anilino-6-bis(2-hydoxyethyl)amino-1,3,5-trizin-2-yl]amino}stilbene-2,2'-disulfonic acid disodium salt, 4-4'-bis(2-sulfostyryl)biphenyl and 4,4'-bis[(4-anilino-6-morpholino-1,3,5-triazin-2-yl)amino]stilbene-2,2'-disulfonic acid disodium salt. Such optical brighteners, or mixtures thereof, can be used at levels in the bar of from about 0.05%–1.0%.

Dyes, pigments, germicides, and perfumes can also be added to the bar composition.

Processing—The detergent laundry bars used in the methods of the present invention can be processed in conventional soap or detergent bar making equipment with some or all of the following key equipment: blender/mixer, mill or refining plodder, two-stage vacuum plodder, logo printer/cutter, cooling tunnel and wrapper.

In a typical process, the raw materials are mixed in the blender. Alkylbenzene sulfonic acid (when used) is added into a mixture of alkaline inorganic salts (preferably which includes sodium carbonate) and the resulting partially neutralized mixture is mechanically worked to effect homogeneity and complete neutralization of the mixture. Once the neutralization reaction is completed, the alkyl sulfate surfactant is added, followed by the remaining other ingredient materials. The mixing can take from 1 minute to 1 hour, with the usual mixing time being from 2 to 20 minutes. The blender mix is discharged to a surge tank. The product is conveyed from the surge tank to the mill or refining plodder via a multi-worn transfer conveyor.

The alkyl benzene sulfonic acid (HLAS) can be made by well-known processes, such as with $SO_3$ or oleum. It can be preferably to include excess inorganic sulfuric acid ($H_2SO_4$) in the stock of HLAS, which, upon neutralization, helps to increase the temperature of the product due to the heat of neutralization of the inorganic sulfuric acid.

After milling or preliminary plodding, the product is then conveyed to a double stage vacuum plodder, operating at a high vacuum, e.g. 600 to 740 millimeters of mercury vacuum, so that entrapped air is removed. The product is extruded and cut to the desired bar length, and printed with the product brand name.

The printed bar can be cooled, for example in a cooling tunnel, before it is wrapped, cased, and sent to storage.

Examples of compositions of the present invention are listed hereafter by way of exemplification, and not by way of limitation.

EXAMPLES

The following examples illustrate the preparation and performance advantages of the suds boosting polymers containing compositions of the instant invention. Such examples, however, are not necessarily meant to limit or otherwise define the scope of the invention herein. All parts, percentages and ratios used herein are expressed as percent weight unless otherwise specified. In the following Examples, the abbreviations for the various ingredients used for the compositions have the following meanings.

| ABBREVIATIONS | |
|---|---|
| LAS | Sodium linear alkyl benzene sulfonate |
| MLAS | Modified Alkyl Benzene sulfonate |
| $MBAS_x$ | Mid-chain branched primary alkyl (average total carbons = x) sulfate |
| $MBAE_xS_z$ | Mid-chain branched primary alkyl (average total carbons = z) ethoxylate (average EO = x) sulfate, sodium salt |
| $MBAE_x$ | Mid-chain branched primary alkyl (average total carbons = x) ethoxylate (average EO = 5) |
| Endolase | Endoglunase enzyme of activity 3000 CEVU/g sold by NOVO Industries A/S |
| MEA | Monoethanolamine |
| PG | Propanediol |
| BPP | Butoxy - propoxy - propanol |
| EtOH | Ethanol |
| NaOH | Solution of sodium hydroxide |
| NaTS | Sodium toluene sulfonate |
| Citric acid | Anhydrous citric acid |
| CxyFA | $C_{1x}$–$C_{1y}$ fatty acid |
| CxyEz | A $C_{1x-1y}$ branched primary alcohol condensed with an average of z moles of ethylene oxide |
| Carbonate | Anhydrous sodium carbonate with a particle size between 200 μm and 900 μm |
| Citrate | Tri-sodium citrate dihydrate of activity 86.4% with a particle size distribution between 425 μm and 850 μm |
| TFAA | C16–18 alkyl N-methyl glucamide |
| LMFAA | C12–14 alkyl N-methyl glucamide |
| APA | C8–C10 amido propyl dimethyl amine |
| Fatty Acid (C12/14) | C12–C14 fatty acid |
| Fatty Acid (TPK) | Topped palm kernel fatty acid |
| Fatty Acid (RPS) | Rapeseed fatty acid |
| Borax | Na tetraborate decahydrate |
| PAA | Polyacrylic Acid (mw = 4500) |
| PEG | Polyethylene glycol (mw = 4600) |
| MES | Alkyl methyl ester sulfonate |
| SAS | Secondary alkyl sulfate |
| NaPS | Sodium paraffin sulfonate |
| C45AS | Sodium $C_{14}$–$C_{15}$ linear alkyl sulfate |
| CxyAS | Sodium $C_{1x}$–$C_{1y}$ alkyl sulfate (or other salt if specified) |
| CxyEzS | Sodium $C_{1x}$–$C_{1y}$ alkyl sulfate condensed with z moles of ethylene oxide (or other salt if specified) |
| CxyEz | A $C_{1x-1y}$ branched primary alcohol condensed with an average of z moles of ethylene oxide |
| AQA | $R_2.N^+(CH_3)_x((C_2H_4O)yH)z$ with $R_2 = C_8 - C_{18}$ x+z = 3, x = 0 to 3, z = 0 to 3, y = 1 to 15. |
| STPP | Anhydrous sodium tripolyphosphate |

ABBREVIATIONS

| | |
|---|---|
| Zeolite A | Hydrated Sodium Aluminosilicate of formula $Na_{12}(AlO_2SiO_2)_{12}.27H_2O$ having a primary particle size in the range from 0.1 to 10 micrometers |
| NaSKS-6 | Crystalline layered silicate of formula $\delta\text{-}Na_2Si_2O_5$ |
| Carbonate | Anhydrous sodium carbonate with a particle size between 200 μm and 900 μm |
| Bicarbonate | Anhydrous sodium bicarbonate with a particle size distribution between 400 μm and 1200 μm |
| Silicate | Amorphous Sodium Silicate ($SiO_2:Na_2O$; 2.0 ratio) |
| Sulfate | Anhydrous sodium sulfate |
| PAE | ethoxylated (15–18) tetraethylene pentamine ethoxylated polyethylene imine |
| PAEC | methyl quaternized ethoxylated dihexylene triamine |
| MA/AA | Copolymer of 1:4 maleic/acrylic acid, average molecular weight about 70,000. |
| CMC | Sodium carboxymethyl cellulose |
| Protease | Proteolytic enzyme of activity 4 KNPU/g sold by NOVO Industries A/S under the tradename Savinase |
| Cellulase | Cellulytic enzyme of activity 1000 CEVU/g sold by NOVO Industries A/S under the tradename Carezyme |
| Amylase | Amylolytic enzyme of activity 60 KNU/g sold by NOVO Industries A/S under the tradename Termamyl 60T |
| Lipase | Lipolytic enzyme of activity 100 kLU/g sold by NOVO Industries A/S under the tradename Lipolase |
| PB1 | Anhydrous sodium perborate bleach of nominal formula $NaBO_2.H_2O_2$ |
| Percarbonate | Sodium Percarbonate of nominal formula $2Na_2CO_3.3H_2O_2$ |
| NaDCC | Sodium dichloroisocyanurate |
| NOBS | Nonanoyloxybenzene sulfonate, sodium salt |
| TAED | Tetraacetylethylenediamine |
| DTPMP | Diethylene triamine penta (methylene phosphonate), marketed by Monsanto under Trade name Dequest 2060 Photoactivated bleach Sulfonated Zinc Phthalocyanine bleach encapsulated in dextrin soluble polymer |
| Brightener 1 | Disodium 4,4'-bis(2-sulphostyryl)biphenyl |
| Brightener 2 | Disodium 4,4'-bis(4-anilino-6-morpholino-1,3,5-triazin-2-yl)amino) stilbene-2:2'-disulfonate. |
| HEDP | 1,1-hydroxyethane diphosphonic acid |
| SRP 1 | Sulfobenzoyl end capped esters with oxyethylene oxy and terephthaloyl backbone |
| SRP 2 | sulfonated ethoxylated terephthalate polymer |
| SRP 3 | methyl capped ethoxylated terephthalate polymer |
| Silicone antifoam | Polydimethylsiloxane foam controller with siloxane-oxyalkylene copolymer as dispersing agent with a ratio of said foam controller to said dispersing agent of 10:1 to 100:1. |
| SUDS1 | Poly(DMAM-co-DMA) (3:1) Copolymer prepared according to Example 1 below |
| SUDS2 | (DMAM), prepared according to Example 2 below |
| SUDS3 | Poly(DMAM-co-AA) (2:1) Copolymer prepared according to Example 3 below |
| SUDS4 | Poly(DMAM-co-MAA) (2:1) Copolymer prepared according to Example 4 below |
| SUDS5 | Poly(DMAM-co-MAA-co-AA) (4:1:1) Terpolymer prepared according to Example 5 below |
| SUDS6 | Poly(DMAM-co-MAA-co-DMA) (4:1:1) Terpolymer prepared according to Example 6 below |
| SUDS7 | (DMAM), prepared according to Example 7 below |
| SUDS8 | Poly(DMA-co-DMAM) (3:1) Copolymer, prepared according to Example 8 below |
| SUDS9 | zwitterionic polymer prepared according to Example 9 below |
| SUDS10 | zwitterionic polymer prepared according to Example 10 below |
| SUDS11 | Polypeptide comprising Lys, Ala, Glu, Tyr (5:6:2:1) having a molecular weight of approximately 52,000 daltons |
| SUDS12 | Lysozyme |
| SUDS13 | LX1279 available from Baker Petrolite |
| Isofol 16 | Condea trademark for C16 (average) Guerbet alcohols |
| CaCl2 | Calcium chloride |
| MgCl2 | Magnesium chloride |
| DTPA | Diethylene triamine pentaacetic acid |

Example 1
Preparation of Poly(DMAM-co-DMA) (3:1) Copolymer 2-(Dimethylamino)ethyl methacrylate (20.00 g, 127.2 mmol), N,N-dimethylacrylamide (4.20 g 42.4 mmol), 2,2'-azobisisobutyronitrile (0.14 g, 0.85 mmol), 1,4-dioxane (75 ml) and 2-propanol (15 ml) are placed into a 250 ml three-necked round-bottomed flask, fitted with a heating mantle, magnetic stirrer, internal thermometer and argon inlet. The mixture is subjected to three freeze-pump-thaw cycles to remove dissolved oxygen. The mixture is heated for 18 hours with stirring at 65° C. TLC (diethyl ether) indicates consumption of monomer. The mixture is concentrated under vacuum by rotary evaporation to remove the solvent. Water is added to make a 10% solution and the mixture is dialyzed (3500 MWCO) against water, lyophilized and then pulverized in a blender to yield a white powder. NMR is consistent with the desired compound.

Example 2
Preparation of Poly(DMAM) Polymer 2-(Dimethylamino)ethyl methacrylate (3000.00 g, 19.082 mol), 2,2'-azobisisobutyronitrile (15.67 g, 0.095 mol), 1,4-dioxane (10.5 L) and 2-propanol (2.1 L) are placed into a 22 L three-necked round-bottomed flask, fitted with a reflux condenser, heating mantle, mechanical stirrer, internal thermometer and argon inlet. The mixture is sparged with argon for 45 minutes with vigorous stirring to remove dissolved oxygen. The mixture is heated for 18 hours with stirring at 65° C. TLC (diethyl ether) indicates consumption of monomer. The mixture is concentrated under vacuum by rotary evaporation to remove the bulk of solvent. A 50:50 mixture of water:t-butanol is added to dissolve the product and the t-butanol is removed under vacuum by rotary evaporation. Water is added to make a 10% solution and the mixture is lyophilized and then pulverized in a blender to yield a white powder. NMR is consistent with the desired compound.

Example 3
Preparation of Poly(DMAM-co-AA) (2:1) Copolymer 2-(Dimethylamino)ethyl methacrylate (90.00 g, 572.4 mmol), acrylic acid (20.63 g, 286.2 mmol), 2,2'-azobisisobutyronitrile (0.70 g, 4.3 mmol), 1,4-dioxane (345 ml) and 2-propanol (86 ml) are placed into a 1000 ml three-necked round-bottomed flask, fitted with a heating mantle, magnetic stirrer, internal thermometer and argon inlet. The mixture is sparged with nitrogen for 30 minutes to remove dissolved oxygen. The mixture is heated for 18 hours with stirring at 65° C. TLC (diethyl ether) indicates consumption of monomer. The mixture is concentrated under vacuum by rotary evaporation to remove the solvent. Water is added to make a 10% solution and the mixture is lyophilized and then pulverized in a blender to yield an off-white-peach powder. NMR is consistent with the desired compound.

Example 4
Preparation of Poly(DMAM-co-MAA) (2:1) Copolymer 2-(Dimethylamino)ethyl methacrylate (98.00 g, 623.3 mmol), methacrylic acid (26.83 g, 311.7 mmol), 2,2'-azobisisobutyronitrile (0.77 g, 4.7 mmol), 1,4-dioxane (435 ml) and 2-propanol (108 ml) are placed into a 1000 ml three-necked round-bottomed flask, fitted with a heating mantle, magnetic stirrer, internal thermometer and argon inlet. The mixture is sparged with nitrogen for 30 minutes to remove dissolved oxygen. The mixture is heated for 18 hours with stirring at 65° C. TLC (diethyl ether) indicates consumption of monomer. The mixture is concentrated under vacuum by rotary evaporation to remove the solvent.

Water is added to make a 10% solution and the mixture is lyophilized and then pulverized in a blender to yield a white powder. NMR is consistent with the desired compound.

Example 5
Poly(DMAM-co-MAA-co-AA) (4:1:1) Terpolymer

Poly(DMAM-co-MAA-co-AA) (4:1:1). The procedure of Example 4 is repeated with the substitution of an equimolar amount of methacrylic acid with a 1:1 mixture of methacrylic acid and acrylic acid.

Example 6
Poly(DMAM-co-MAA-co-DMA) (4:1:1) Terpolymer

Poly(DMAM-co-MAA-co-AA) (4:1:1). The procedure of Example 4 is repeated with the substitution of an equimolar amount of methacrylic acid with a 1:1 mixture of methacrylic acid and N,N-dimethylacrylamide.

Example 7
Preparation of Poly(DMAM) Polymer

Polyacrylic acid is esterified with 2-(dimethylamino) ethanol using well known methods such as one described in Org. Syn. Coll. Vol. 3 610 (1955).

Example 8
Preparation of Poly(DMA-co-DMAM) (3:1) Copolymer

The procedure of Example 1 is repeated except that 2-(dimethylamino)ethyl methacrylate (6.67 g, 42.4 mmol), N,N-dimethylacrylamide (12.6 g 127.2 mmol) is used instead, to give a ratio in the polymer of DMA to DMAM of 3:1.

Example 9

Preparation of Zwitterionic Polymer
Reaction of (1-Octene/Maleic Anhydride) Copolymer with 1 Equivalent of DMAPA Poly(maleic anhydride-alt-1-octene) (15.00 g) and tetrahydrofuran (200 ml, anhydrous) a placed into a 250 ml three-necked round-bottom flask, fitted with a heating mantle, magnetic stirrer, dropping funnel, internal thermometer and argon inlet. 3-Dimethylaminopropylamine (7.65 g, 74.87 mmol) is added dropwise over 15 minutes, with an exotherm to 30° C. and heavy precipitation. The mixture is stirred for 4 hours at 55° C. The mixture is poured into 3:1 ethyl ether:hexanes to precipitate the product which is dried under vacuum to yield a white powder. NMR is consistent with the desired compound.

Example 10
Reaction of (1-Hexene/Maleic Anhydride) Copolymer with 1 Equivalent of DMAPA Poly(maleic anhydride-alt-1-hexene) (15.00 g) and pyridine (150 ml, anhydrous) are placed into a 250 ml three-necked round-bottom flask, fitted with a heating mantle, magnetic stirrer, dropping funnel, internal thermometer and argon inlet. There is a slight exotherm and the mixture is dark. 3-Dimethylaminopropylamine (9.25 g, 90.53 mmol) is added dropwise over 15 minutes, with an exotherm to 45° C. The mixture is stirred for 4 hours at 80° C. The mixture is concentrated by rotary evaporation, dissolved into water and lyophilized to yield a yellow powder. NMR is consistent with the desired compound.

Example 11

Preparation of LAS Powder for Use as a Structurant

Sodium $C_{12}$ linear alkyl benzene sulfonate (NaLAS) is processed into a powder containing two phases. One of these phases is soluble in the non-aqueous liquid detergent compositions herein and the other phase is insoluble. It is the insoluble fraction which serves to add structure and particle suspending capability to the non-aqueous phase of the compositions herein.

NaLAS powder is produced by taking a slurry of NaLAS in water (approximately 40–50% active) combined with dissolved sodium sulfate (3–15%) and hydrotrope, sodium sulfosuccinate (1–3%). The hydrotrope and sulfate are used to improve the characteristics of the dry powder. A drum dryer is used to dry the slurry into a flake. When the NaLAS is dried with the sodium sulfate, two distinct phases are created within the flake. The insoluble phase creates a network structure of aggregate small particles (0.4–2 um) which allows the finished non-aqueous detergent product to stably suspend solids.

The NaLAS powder prepared according to this example has the following makeup shown below.

| LAS Powder | |
| --- | --- |
| Component | Wt. % |
| NaLAS | 85% |
| Sulfate | 11% |
| Sulfosuccinate | 2% |
| Water | 2.5% |
| Unreacted, etc. | balance to 100% |
| % insoluble LAS | 17% |
| # of phase (via X-ray diffraction) | 2 |

Example 12

Non-aqueous based heavy duty liquid laundry detergent compositions (A to E) which comprise the mid-chain branched surfactants of the present invention are presented below.

| Non-Aqueous Liquid Detergent Composition with Bleach | | | | | |
| --- | --- | --- | --- | --- | --- |
| Component | Wt % A | Wt % B | Wt % C | Wt % D | Wt % E |
| LAS, From Example I | 16 | 13 | 36 | 8 | 2 |
| Mid-branched Surfactant | 22 | 25 | 0 | 30 | 34 |
| BPP | 19 | 19 | 19 | 19 | 19 |
| Sodium citrate dihydrate | 3 | 3 | 3 | 3 | 3 |
| Bleach activator | 5.9 | 5.9 | 5.9 | 5.9 | 5.9 |
| Sodium carbonate | 9 | 9 | 9 | 9 | 9 |
| SUDS3 | 0.2 | 0.5 | 1.0 | 0.1 | 0.5 |
| Maleic-acrylic copolymer | 3 | 3 | 3 | 3 | 3 |
| Colored speckles | 0.4 | 0.4 | 0.4 | 0.4 | 0.4 |
| EDDS | 1 | 1 | 1 | 1 | 1 |
| Cellulase Prills | 0.1 | 0.1 | 0.1 | 0.1 | 0.1 |
| Amylase Prills | 0.4 | 0.4 | 0.4 | 0.4 | 0.4 |
| Ethoxylated diamine quat | 1.3 | 1.3 | 1.3 | 1.3 | 1.3 |
| Sodium Perborate | 15 | 15 | 15 | 15 | 15 |
| Optionals including: brightener, colorant, perfume, thickener, suds suppressor, colored speckles etc. | balance | balance | balance | balance | balance |
| | 100% | 100% | 100% | 100% | 100% |

The resulting compositions are stable, anhydrous heavy-duty liquid laundry detergents which provide excellent stain and soil removal performance when used in normal fabric laundering operations.

Example 13

A non-limiting example of bleach-containing nonaqueous liquid laundry detergent is prepared having the composition as set forth below.

| Component | Wt. % | Range (% wt.) |
|---|---|---|
| Liquid Phase | | |
| LAS | 25.0 | 18–35 |
| $C_{24}E5$ or $MBAF_{14.3}$ | 13.6 | 10–20 |
| Hexylene glycol | 27.3 | 20–30 |
| Perfume | 0.4 | 0–1.0 |
| SUDS1 | 0.2 | 0.01 to 5.0 |
| $MBAE_2S_{14.4}$ | 2.3 | 1–3.0 |
| Solid Phase | | |
| Protease | 0.4 | 0–1.0 |
| Citrate | 4.3 | 3–6 |
| PB1 | 3.4 | 2–7 |
| NOBS | 8.0 | 2–12 |
| Carbonate | 13.9 | 5–20 |
| DTPA | 0.9 | 0–1.5 |
| Brightener 1 | 0.4 | 0–0.6 |
| silicone antifoam | 0.1 | 0–0.3 |
| Minors | Balance | — |

The resulting composition is an anhydrous heavy duty liquid laundry detergent which provides excellent stain and soil removal performance when used in normal fabric laundering operations.

Example 14

Liquid detergent compositions are made according to the following.

| | A | B | C | D |
|---|---|---|---|---|
| $C_{25}$ AE3S | 2 | 8 | 17 | 5 |
| $MBAS_{14.4}$ | 15 | 12 | 0 | 8 |
| $C_{12}$–$C_{14}$ alkyldimethyl amine oxide | — | — | — | 2 |
| SUDS2 | 0.1 | 0.2 | 2.0 | 0.7 |
| $C_{25}$ AS | 6 | 4 | 6 | 8 |
| $C_{24}$ N-methyl glucamide | 5 | 4 | 3 | 3 |
| $C_{24}$ AE5 | 6 | 1 | 1 | 1 |
| $C_{12}$–$C_{18}$ fatty acid | 11 | 4 | 4 | 3 |
| Citric acid | 1 | 3 | 3 | 2 |
| DTPMP | 1 | 1 | 1 | 0.5 |
| MEA | 8 | 5 | 5 | 2 |
| NaOH | 1 | 2.5 | 1 | 1.5 |
| PG | 14.5 | 13.1 | 10.0 | 8 |
| EtOH | 1.8 | 4.7 | 5.4 | 1 |
| Amylase (300 KNU/g) | 0.1 | 0.1 | 0.1 | 0.1 |
| Lipase D96/L (100 KNU/g) | 0.15 | 0.15 | 0.15 | 0.15 |
| Protease (35 g/l) | 0.5 | 0.5 | 0.5 | 0.5) |
| Endolase | 0.05 | 0.05 | 0.05 | 0.05 |
| Cellulase | 0.09 | 0.09 | 0.09 | 0.09 |
| Terephthalate-based polymer | 0.5 | — | 0.3 | 0.3 |
| Boric acid | 2.4 | 2.8 | 2.8 | 2.4 |
| Sodium xylene sulfonate | — | 3 | — | — |
| 2-butyl-octanol | 1 | 1 | 1 | 1 |
| Branched silicone | 0.3 | 0.3 | 0.3 | 0.3 |
| Water & minors | | | | Up to 100% |

The above liquid detergent compositions (A–D) are found to be very efficient in the removal of a wide range of stains and soils from fabrics under various usage conditions.

The Following Examples illustrate aqueous based liquid detergent compositions according to the present invention.

Example 15

Aqueous based heavy duty liquid laundry detergent compositions F to J which comprise the mid-chain branched surfactants of the present invention are presented below.

| Ingredient | F | G | H | I | J |
|---|---|---|---|---|---|
| MBAE1.8S14.4 | 10 | 12 | 14 | 16 | 20 |
| Na C25AE1.8S | 10 | 8 | 6 | 4 | 0 |
| C23E9 | 2 | 2 | 2 | 2 | 2 |
| LMFAA | 5 | 5 | 5 | 5 | 0 |
| SUDS3 | 0.01 | 0.2 | 1.0 | 1.5 | 0.8 |
| Citric acid builder | 3 | 3 | 3 | 3 | 5 |
| Fatty acid builder | 2 | 2 | 2 | 2 | 0 |
| PAE | 1 | 1 | 1.2 | 1.2 | 0.5 |
| PG | 8 | 8 | 8 | 8 | 4.5 |
| EtOH | 4 | 4 | 4 | 4 | 2 |
| Boric acid | 3.5 | 3.5 | 3.5 | 3.5 | 2 |
| Sodium Cumene Sulfonate | 3 | 3 | 3 | 3 | 0 |
| pH = | 8.0 | 8.0 | 8.0 | 8.0 | 7.0 |
| Enzymes, dyes, water | balance | balance | balance | balance | balance |
| | 100% | 100% | 100% | 100% | 100% |

Example 16

The following aqueous liquid laundry detergent compositions K to O are prepared in accord with the invention:

| | K | L | M | N | O |
|---|---|---|---|---|---|
| MBAE1.8S14.4 and/or MBAS14.4 | 0 | 7–12 | 12–17 | 17–22 | 1–35 |
| Any combination of: C25 AExS*Na (x = 1.8–2.5) C25 AS (linear to high 2-alkyl) C14–17 NaPS C12–16 SAS C18 1,4 disulfate LAS C12–16 MES | 15–21 | 10–15 | 5–10 | 0–5 | 0–25 |
| LMFAA | 0–3.5 | 0–3.5 | 0–3.5 | 0–3.5 | 0–8 |
| C23E9 or C23E6.5 | 0–2 | 0–2 | 0–2 | 0–2 | 0–8 |
| SUDS13 | 0.15 | 0.35 | 0.55 | 1.75 | 0.3 |
| APA | 0.5 | 0.5 | 0.5 | 0.5 | 0.5–2 |
| Citric Acid | 5 | 5 | 5 | 5 | 0–8 |
| Fatty Acid (TPK or C12/14) | 2 | 2 | 2 | 2 | 0–14 |
| EtOH | 4 | 4 | 4 | 4 | 0–8 |
| PG | 6 | 6 | 6 | 6 | 0–10 |
| MEA | 1 | 1 | 1 | 1 | 0–3 |
| NaOH | 3 | 3 | 3 | 3 | 0–7 |
| Na TS | 2.3 | 2.3 | 2.3 | 2.3 | 0–4 |
| Na formate | 0.1 | 0.1 | 0.1 | 0.1 | 0–1 |
| Borax | 2.5 | 2.5 | 2.5 | 2.5 | 0–5 |
| Protease | 0.9 | 0.9 | 0.9 | 0.9 | 0–1.3 |
| Lipase | 0.06 | 0.06 | 0.06 | 0.06 | 0–0.3 |
| Amylase | 0.15 | 0.15 | 0.15 | 0.15 | 0–0.4 |
| Cellulase | 0.05 | 0.05 | 0.05 | 0.05 | 0–0.2 |
| PAE | 0–0.6 | 0–0.6 | 0–0.6 | 0–0.6 | 0–2.5 |
| PIE | 1.2 | 1.2 | 1.2 | 1.2 | 0–2.5 |
| PAEC | 0–0.4 | 0–0.4 | 0–0.4 | 0–0.4 | 0–2 |
| SRP 2 | 0.2 | 0.2 | 0.2 | 0.2 | 0–0.5 |
| Brightener 1 or 2 | 0.15 | 0.15 | 0.15 | 0.15 | 0–0.5 |
| Silicone antifoam | 0.12 | 0.12 | 0.12 | 0.12 | 0–0.3 |
| Fumed Silica | 0.0015 | 0.0015 | 0.0015 | 0.0015 | 0–0.003 |
| Perfume | 0.3 | 0.3 | 0.3 | 0.3 | 0–0.6 |
| Dye | 0.0013 | 0.0013 | 0.0013 | 0.0013 | 0–0.003 |
| Moisture/minors | Balance | Balance | Balance | Balance | Balance |
| Product pH (10% in DI water) | 7.7 | 7.7 | 7.7 | 7.7 | 6–9.5 |

Various bar compositions can be made using the method described above.

Example 17

|  | A | B | C | D | E | F | G | H | I |
|---|---|---|---|---|---|---|---|---|---|
|  |  |  |  |  | (weight percent) |  |  |  |  |
| NaCFAS($C_{12-18}$) | 15.75 | 15.75 | 19.13 | 11.20 | 22.50 | 13.50 |  |  |  |
| Na($C_{12-18}$)LAS | 6.75 | 6.75 | 3.38 | 8.80 |  |  | 19.00 | 15.00 | 21.00 |
| $Na_2CO_3$ | 15.00 | 5.00 | 15.00 | 15.00 | 10.0 | 3.00 | 13.0 | 8.00 | 10.0 |
| DTPP[1] | 0.70 | 0.70 | 0.70 | 0.70 | 0.70 | 0.70 | 0.60 |  | 0.60 |
| SUDS13 |  | 0.5 |  |  |  |  |  |  | 0.1 |
| SUDS3 | 0.2 |  |  | 0.25 |  | 0.8 |  | 0.15 | 0.2 |
| SUDS12 |  |  | 0.2 |  |  |  |  | 0.2 |  |
| SUDS1 |  |  |  |  | 0.2 |  | 0.2 | 0.2 | 0.2 |
| PEO-300M[2] |  |  |  |  | 0.30 |  |  | 0.30 |  |
| PEO-600M |  |  |  |  |  | 0.20 | 0.20 |  |  |
| Bentonite clay |  |  | 10.0 |  |  | 10.0 |  | 5.0 |  |
| Sokolan CP-5[3] | 0.40 | 0.70 | 0.40 | 0.70 | 0.40 | 1.00 |  | 0.20 |  |
| TSPP | 5.00 |  | 5.00 |  | 5.00 |  | 5.00 | 5.00 |  |
| STPP | 5.00 | 10.00 | 5.00 | 10.00 | 10.00 | 15.00 |  |  |  |
| Zeolite | 1.25 | 1.25 | 1.25 | 1.25 | 1.25 | 1.25 |  |  |  |
| Sodium laurate |  |  |  |  |  | 9.00 |  |  |  |
| SRP-A[4] | 0.30 | 0.30 | 0.30 | 0.30 | 0.30 | 0.30 | 0.22 |  | 0.22 |
| Protease enzyme[5] |  |  |  |  | 0.08 | 0.12 |  | 0.08 | 0.08 |
| Amylase enzyme[6] |  |  |  | 0.80 |  |  |  | 0.80 |  |
| Lipase enzyme |  |  |  |  |  | 0.10 |  | 0.10 |  |
| Cellulase enzyme[7] |  |  |  |  |  | 0.15 |  |  | 0.15 |
|  |  |  |  |  | Balance[8] |  |  |  |  |

[1]Sodium diethylenetriamine penta (phosphonate)
[2]PEO is poly(ethylene oxide) having a molecular weight as indicated.
[3]Sokolan CP-5 is maleic-acrylic copolymer
[4]SRP-A is
$NaO_3S(CH_2CH_2O)_2$—C(O)—$(C_6H_4)$—C(O)O—[—$CH_2CRH$—O—C(O)—$(C_6H_4)$—C(O)O—]$_4$—
—[—$CH_2CRH$—O—C(O)—$(C_6H_4)SO_3Na$—C(O)O—]$_1$—$CH_2CH_2OCH_2CH_2SO_3Na$,
wherein R is H or $CH_3$ in a ratio of about 1.8:1.
[5]Protease activity at 1 Au/gm stock.
[6]Amylase activity at 100,000 amu/gm stock.
[7]Carezyme ® cellulase, supplied by Novo Nordisk, activity at 5000 Cevu/gm stock.
[8]Balance comprises water (about 2% to 8%, including water of hydration), sodium sulfate, calcium carbonate, and other minor ingredients.

Example 18

The following compositions were made by mixing the listed ingredients in the listed proportions. These compositions were used neat to clean marble and dilute to clean lacquered wooden floors. Excellent cleaning and surface safety performance was observed.

|  | A | B | C | D | E | F | G | H |
|---|---|---|---|---|---|---|---|---|
| MLAS | 3.0 | 3.0 | 5.0 | 3.2 | 3.2 | 3.2 | 8.0 | 8.0 |
| Dobanol ® 23-3 | 1.0 | 1.0 | 1.5 | 1.3 | 1.3 | 1.5 | 3.0 | 3.5 |
| Empilan KBE21+ | 2.0 | 2.0 | 2.5 | 1.9 | 1.9 | 2.0 | 5.0 | 6.0 |
| NaPS | 2.0 | 1.5 | 1.2 | 1.2 | 1.0 | 1.7 | 3.0 | 2.5 |
| SUDS5 | 0.1 | 2.5 | 0.1 | 0.05 | 0.2 | 0.3 | 0.5 | 0.25 |
| NaCS | 1.2 | 3.0 | 2.2 | 2.0 | 2.0 | 1.5 | 4.0 | 5.0 |
| MgSO4 | 0.20 | 0.9 | 0.30 | 0.50 | 1.3 | 2.0 | 1.0 | 3.0 |
| Citrate | 0.3 | 1.0 | 0.5 | 0.75 | 1.8 | 3.0 | 1.5 | 6.0 |
| NaHCO3 | 0.06 | 0.1 | — | 0.1 | — | 0.2 | — | — |
| Na2HPO4 | — | — | 0.1 | — | 0.3 | — | — | — |
| Na2H2P2O7 | — | — | — | — | — | — | 0.2 | 0.5 |
| pH | 8.0 | 7.5 | 7.0 | 7.25 | 8.0 | 7.4 | 7.5 | 7.2 |
| Water and Minors |  |  |  | q.s. to 100% |  |  |  |  |

As used hereinabove:
NaPS stands for Na paraffin sulphonate
NaCS stands for Na cumene sulphonate
Dobanol ® 23-3 is a C12–13 alcohol ethoxylated with an average ethoxylation degree of 3.
Empilan KBE21 is a C12–14 alcohol ethoxylated with an average ethoxylation degree of 21.

Example 19

|  | I | J | K | L | M | N |
|---|---|---|---|---|---|---|
| C13–15 EO30 | 1 | — | — | — | — | — |
| C12–14 EO20 | — | — | 1 | 1.7 | — | — |
| C12–14PO3EO7 | — | — | — | — | — | 2 |
| C12–14 EO10 | — | — | — | — | 2 | — |
| C10–12 EO10 | — | 1.5 | — | — | — | — |
| SUDS7 | 0.2 | 0.1 | 0.3 | 0.5 | 0.2 | 0.1 |
| MLAS | — | — | 2.4 | — | 2.4 | 2.4 |
| C11EO5 | — | — | — | 5 | — | — |
| C12–14 EOS | 4.2 | 3.0 | 3.6 | — | 3.6 | 3.6 |
| C9–11 EO4 | — | 3.0 | — | — | — | — |
| C12-OH | — | 0.3 | — | — | — | — |
| 2-Hexyl decanol | — | — | — | 0.4 | — | — |
| 2-Butyl octanol | 0.3 | — | 0.3 | — | 0.3 | 0.3 |
| MBAS | — | — | 1.0 | — | 1.0 | 1.0 |
| MBAES | 1.0 | 1.3 | — | 1.5 | — | — |
| Citrate | 0.7 | 1.0 | 0.7 | 1.0 | 0.7 | 0.7 |
| Na2CO3 | 0.6 | 0.7 | 0.6 | 0.3 | 0.6 | 0.6 |

Example 20

The following compositions were made by mixing the listed ingredients in the listed proportions:

|  | Weight % | | | |
|---|---|---|---|---|
| Ingredients | FF | GG | HH | II |
| MLAS | 4 | — | 3 | 4 |
| Alcohol ethoxylate 30EO (1) | 2 | — | — | 2 |

-continued

| Ingredients | Weight % | | | |
|---|---|---|---|---|
| | FF | GG | HH | II |
| Alcohol ethoxylate 12EO (2) | — | 3 | — | — |
| Alcohol benzene ethoxylate 10EO (4) | — | — | 3 | — |
| SUDS8 | 0.1 | 0.2 | 0.2 | 0.5 |
| Citric acid | 2 | 2 | 2 | 3 |
| Butylcarbitol[R] | 4 | 4 | 4 | 7 |
| n-butoxypropoxypropanol | — | — | — | 2.5 |
| Triethanolamine | 1 | 1 | 2 | 1 |
| water & minors | q.s. to 100% | | | |

In the examples hereinabove, (1) is a highly ethoxylated nonionic surfactant wherein R is a mixture of $C_{13}$ and $C_{15}$ alkyl chains and n is 30. (2) is a highly ethoxylated nonionic surfactant wherein R is a mixture of $C_{13}$ and $C_{15}$ alkyl chains and n is 12. (3) is a lower ethoxylated nonionic surfactant wherein n is 7. (4) is a highly ethoxylated nonionic surfactant wherein R is a mixture of $C_{19}$ and $C_{21}$ alkyl benzene chains and n is 10.

Compositions FF-MM described hereinabove can be used neat or diluted. In a method according to the present invention, these compositions are diluted in 65 times their weight of water and applied to a hard surface.

Example 21

The following compositions were tested for their cleaning performance when used diluted on greasy soil.

The following compositions were made by mixing the listed ingredients in the listed proportions:

| Ingredients | Weight % | | |
|---|---|---|---|
| | NN | OO | PP |
| Sodium paraffin sulfonate | 1.0 | 3 | 3 |
| Alcohol ethoxylate 7EO | 4 | — | — |
| Alcohol ethoxylate 30EO | — | 3 | 2 |
| C12–14 EO21 alcohol ethoxylate | 1.0 | — | — |
| SUDS3 | 0.2 | 0.3 | 4.0 |
| MLAS | 5.0 | 0 | 2 |
| Sodium Citrate | 3 | 3 | 3 |
| Butylcarbitol[R] | 4 | 4 | 4 |
| Triethanolamine | 1 | 1 | 1 |
| water & minors | up to 100% | | |

Example 22

A Shampoo Composition

| Components | Weight % | |
|---|---|---|
| | A | B |
| TEA C12–C14 Alkyl Sulfate | 10.00 | — |
| NH4 C12–C14 Alkyl (Ethoxy)3 Sulfate | — | 7.90 |
| SUDS1 | 0.2 | 1.0 |
| Cocamide MEA | 3.00 | 1.50 |
| Dimethicone DC-200* | 3.00 | 3.00 |
| Ethylene Glycol Disterate | 1.50 | 1.50 |
| Citric acid | 0.60 | 0.60 |
| Trisodium citrate | 0.30 | — |
| Q.S. Color, preservative, Perfume and water | q.s. to 100% | q.s. to 100% |

Example 23

The following are personal cleansing compositions of the present invention.

| Components | Weight % | |
|---|---|---|
| | C | D |
| Ammonium Lauryl Sulfate | 2.5 | 9.5 |
| Ammonium Laureth (3) Sulfate | 8.5 | 8.5 |
| JAGUAR C-17[1] | 0.5 | 0.5 |
| MBAS | 6.0 | — |
| SUDS9 | 1.0 | 0.3 |
| Coconut Monoethanol Amide | 1.0 | 1.0 |
| Ethylene Glycol Distearate | 2.0 | 2.0 |
| Isocetyl Stearoyl Stearate | 1.0 | 1.0 |
| Tricetyl Methyl Ammonium Chloride | 0.5 | 0.5 |
| Polydimethylsiloxane[2] | 2.0 | 2.0 |
| Cetyl Alcohol | 0.4 | 0.4 |
| Stearyl Alcohol | 0.2 | 0.2 |
| Perfume | 1.0 | 1.0 |
| Color Solution | 0.6 | 0.6 |
| Preservative | 0.4 | 0.4 |
| Water and Minors | q.s to 100% | q.s to 100% |

[1]Tradename for guar hydroxypropyltrimonium chloride, a cationic polymer available from Rhone-Poulenc (Cranbury, NJ, USA).
[2]A 40/60 weight ratio blend of polydimethylsiloxane gum (GE SE 76, available from General Electric Co., Silicone Products Div., Waterford, NY, USA) and polydimethylsiloxane fluid bout 350 centistokes).

The composition can provide excellent in-use hair cleaning and conditioning. As an alternative, the JAGUAR C-17 can be replaced with LUVIQUAT FC 370.

Example 24

The following are personal cleansing compositions of the present invention.

| Component | Weight % | |
|---|---|---|
| | E | F |
| Ammonium Lauryl Sulfate | 4.2 | 2.2 |
| Ammonium Laureth (3) Sulfate | 9.2 | 9.2 |
| POLYMER LR 400[1] | 1.0 | 1.0 |
| MBAS | — | 6.0 |
| Coconut Monoethanol Amide | 1.0 | 1.0 |
| Ethylene Glycol Distearate | 2.0 | 2.0 |
| Light Mineral Oil | 1.0 | 1.0 |
| Tricetyl Methyl Ammonium Chloride | 0.5 | 0.5 |
| SUDS1 | 0.75 | 1.25 |
| Polydimethylsiloxane[2] | 1.5 | 1.5 |
| Cetyl Alcohol | 0.4 | 0.4 |
| Stearyl Alcohol | 0.2 | 0.2 |
| Perfume | 1.2 | 1.2 |
| Color Solution | 0.6 | 0.6 |
| Preservative | 0.4 | 0.4 |
| Water and Minors | q.s. to 100% | q.s. to 100% |

[1]Cellulose, 2-[2-hydroxy-3-(trimethyl ammonio)propoxy] ethyl ether, chloride, a cationic polymer available from Amerchol Corp. (Edison, NJ, USA).
[2]A 40/60 weight ratio blend of polydimethylsiloxane gum (GE SE 76, available from General Electric Co., Silicone Products Div., Waterford, NY, USA) and polydimethylsiloxane fluid (about 350 centistokes).

The composition can provide excellent in-use hair cleaning and conditioning

Example 25

The following is an example of a personal cleansing composition of the present invention wherein the cationic polymer and anionic surfactant component form a complex coacervate phase.

| Component | Weight % G |
|---|---|
| Ammonium Laureth (3) Sulfate | 4.0 |
| LUVIQUAT FC 370[1] | 0.5 |
| BAS[2] | 13.5 |
| Coconut Monoethanol Amide | 1.0 |
| Ethylene Glycol Distearate | 2.0 |
| Light Mineral Oil | 0.5 |
| SUDS8 | 0.45 |
| Tricetyl Methyl Ammonium Chloride | 0.5 |
| Polydimethylsiloxane[2] | 3.0 |
| Cetyl Alcohol | 0.4 |
| Stearyl Alcohol | 0.2 |
| Perfume | 1.0 |
| Color Solution | 0.6 |
| Preservative | 0.4 |
| Water and Minors | 73.8 |

[1]Tradename of BASF Wyandotte Corporation (Parsippany, NJ, USA) for copolymer of vinyl pyrrolidone and methyl vinyl imidazolium chloride.
[2]The Mid-Chain Branched surfactants according to example II.
[3]A 40/60 weight ratio blend of polydimethylsiloxane gum (GE SE 76, available from General Electric Co., Silicone Products Div., Waterford, NY, USA) and polydimethylsiloxane fluid (about 350 centistokes).

The composition can provide excellent in-use hair cleaning and conditioning. As an alternative, the LUVIQUAT FC 370 can be replaced with JAGUAR C-17.

Example 26

The following is an example of a personal cleansing composition of the present invention.

| Component | Weight % H |
|---|---|
| Cocoamidopropyl Betaine | 4.0 |
| Ammonium Laureth (3) Sulfate | 8.0 |
| Coconut Monoethanol Amide | 2.0 |
| Ethylene Glycol Distearate | 2.0 |
| Polymer JR-125[1] | 1.0 |
| MBAS | 4.0 |
| SUDS2 | 0.2 |
| Isopropyl Isosterate | 1.0 |
| Tricetyl Methyl Ammonium Chloride | 0.5 |
| Polydimethyisiloxane[2] | 1.5 |
| Cetyl Alcohol | 0.4 |
| Stearyl Alcohol | 0.2 |
| Perfume | 1.0 |
| Color Solution | 0.6 |
| Preservative | 0.4 |
| Water and Minors | q.s. to 100% |

[1]Cellulose, 2-[2-hydroxy-3-(trimethyl ammmonio)propoxy] ethyl ether, chloride, available from Amerchol Corp. (Edison, NJ, USA).
[2]VISCASIL 12,500 cS silicone fluid, available from General Electric (Waterford, NY, USA).

Example 27

The following are personal cleansing compositions of the present invention.

| | Weight % | |
|---|---|---|
| Component | I | J |
| Ammonium Lauryl Sulfate | 8.5 | 2.0 |
| Ammonium Laureth (3) Sulfate | 4.0 | 4.0 |
| Polymer LM-200[1] | 1.0 | 1.0 |
| MBAS | 5.0 | 11.5 |

| | Weight % | |
|---|---|---|
| Component | I | J |
| Light Mineral Oil | 1.0 | 1.0 |
| Coconut Monoethanol Amide | 1.0 | 1.0 |
| Ethylene Glycol Distearate | 2.0 | 2.0 |
| SUDS6 | 0.6 | 0.1 |
| Tricetyl Methyl Ammonium Chloride | 0.5 | 0.5 |
| Polydimethylsiloxane[2] | 3.0 | 3.0 |
| Cetyl Alcohol | 0.4 | 0.4 |
| Stearyl Alcohol | 0.2 | 0.2 |
| Perfume | 1.0 | 1.0 |
| Color Solution | 0.6 | 0.6 |
| Preservative | 0.4 | 0.4 |
| Water and Minors | q.s. to 100% | q.s. to 100% |

[1]Polyquaternium 24, a polymeric quaternary ammonium salt of hydroxyethyl cellulose reacted with lauryl dimethyl ammonium-substituted epoxide, available from Amerchol Corp. (Edison, NJ, USA).
[2]A 40/60 weight ratio blend of polydimethylsiloxane gum (GE SE 76, available from General Electric Co., Silicone Products Div., Waterford, NY, USA) and polydimethylsiloxane fluid (about 350 centistokes).

Example 28

The following is a personal cleansing composition of the present invention wherein the cationic polymer and anionic surfactant component form a complex coacervate phase.

| Component | Weight % K |
|---|---|
| Ammonium Laureth (3) Sulfate | 8.5 |
| GAFQUAT 755N[1] | 0.5 |
| FLEXAN 130[3] | 0.5 |
| Coconut Monoethanol Amide | 1.0 |
| Ethylene Glycol Distearate | 2.0 |
| MBAS | 8.5 |
| Isocetyl Stearoyl Stearate | 1.0 |
| Tricetyl Methyl Ammonium Chloride | 0.5 |
| Polydimethylsiloxane[2] | 2.0 |
| Cetyl Alcohol | 0.4 |
| SUDS5 | 0.1 |
| Stearyl Alcohol | 0.2 |
| Perfume | 1.0 |
| Color Solution | 0.6 |
| Preservative | 0.4 |
| Water and Minors | q.s. to 100% |

[1]Copolymer of 1-vinyl-2-pyrrolidone and dimethylaminoethylmethacrylate, available from GAF Corp., Wayne, NJ, USA.
[2]VISCASIL, 600,000 cS, from General Electric, Waterford, NY, USA.
[3]Sodium polystyrene sulfonate, an anionic polymer available from National Starch and Chemical Corp., Bridgewater, NJ, USA.

The composition can provide excellent in-use hair cleaning and conditioning.

The example compositions hereof can be made by preparing a premix of the entire amount of silicone conditioning agent to be incorporated into the personal cleansing, along with sufficient ammonium sulfate and cetyl and stearyl alcohol such that the premix comprises about 30% silicone conditioning agent, about 69% surfactant, and about 1% of the alcohols. The premix ingredients are heated and stirred at 72° C. for about 10 minutes and the premix is then conventionally mixed with the remaining hot (72° C.) ingredients. The composition is then pumped through a high shear mixer and cooled.

Example 29

The following examples, (L to Z), further describe and demonstrate embodiments within the scope of the present invention. The examples are given solely for the purpose of illustration and are not to be construed as limitations of the present invention, as many variations thereof are possible without departing from the spirit and scope of the invention. These exemplified embodiments of the shampoo compositions of the present invention provide cleansing of hair and improved hair conditioning performance. Ingredients are hereinafter identified by chemical, trade, or CTFA name.

Preparation The shampoo compositions of the present invention can be prepared by using conventional mixing and formulating techniques. The shampoo compositions illustrated hereinafter in Examples L to Z are prepared in the following manner.

About one-third to all of the total sulfate surfactant (added as a 25% solution) is added to a jacketed mix tank and heated to about 74° C. with slow agitation to form a surfactant solution. Cocamide MEA and fatty alcohol, as applicable, are added to the tank and allowed to disperse. Ethylene glycol distearate (EGDS), as applicable, is then added to the mixing vessel, and melted. After the EGDS is well dispersed (usually about 5 to 20 minutes) polyethylene glycol and the preservative, if used are added and mixed into the surfactant solution. This mixture is passed through a heat exchanger where it is cooled to about 35° C. and collected in a finishing tank. As a result of this cooling step, the ethylene glycol distearate crystallizes to form a crystalline network in the product. The remainder of the surfactant and other ingredients including the silicone emulsions are added to the finishing tank with ample agitation to insure a homogeneous mixture. A sufficient amount of the silicone emulsions are added to provide the desired level of dimethicone in the final product. Water dispersible polymers are typically dispersed in water as a 1% to 10% solution before addition to the final mix. Once all ingredients have been added, ammonium xylene sulfonate or additional sodium chloride can be added to the mixture to thin or thicken respectively to achieve a desired product viscosity. Preferred viscosities range from about 2500 to about 9000 cS at 25° C. (as measured by a Wells-Brookfield cone and plate viscometer at 15/s).

| Component | L | M | N | O | P |
|---|---|---|---|---|---|
| Ammonium BAS | 2 | 4 | 4 | 5 | 4 |
| Ammonium BAES | 8 | 6 | 12 | 10 | 12 |
| Cocamidopropylbetaine | 0 | 0 | 2.5 | 0 | 1 |
| Jaguar C17[5] | 0.05 | 0 | 0.05 | 0.30 | 0.15 |
| SUDS3 | 0.2 | 2.5 | 0.2 | 0.15 | 0.5 |
| Cocamide MEA | 0.5 | 0.5 | 0.80 | 0.80 | 0 |
| Cetyl Alcohol | 0 | 0 | 0.42 | 0.42 | 0.42 |
| Stearyl Alcohol | 0 | 0 | 0.18 | 0.18 | 0.18 |
| Ethylene Glycol Distearate | 1.50 | 1.50 | 1.50 | 1.50 | 1.50 |
| EP Silicone[1] | 3.0 | 2.5 | 3.0 | 2.0 | 3.0 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | q.s. to 100% | | | | |

| Component | Q | R | S | T | U |
|---|---|---|---|---|---|
| Ammonium BAES | 9.00 | 9.00 | 14.0 | 14.85 | 12.50 |
| Cocamidopropylbetaine | 1.70 | 1.70 | 2.70 | 1.85 | 4.20 |
| Polyquaternium-10[3] | 0.05 | 0.02 | 0.15 | 0.15 | 0.15 |
| Cocamide MEA | 0.80 | 0.80 | 0.80 | 0.80 | 0 |
| SUDS2 | 0.2 | 0.36 | 0.42 | 1.0 | 0.15 |
| Cetyl Alcohol | 0 | 0 | 0.42 | 0.42 | 0.42 |
| Stearyl Alcohol | 0 | 0 | 0.18 | 0.18 | 0.18 |
| Ethylene Glycol Distearate | 1.50 | 1.50 | 1.50 | 1.50 | 1.50 |
| EP Silicone[4] | 3.0 | 2.5 | 3.0 | 2.0 | 3.0 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | q.s. to 100% | | | | |

| Component | V | W | X | Y | Z |
|---|---|---|---|---|---|
| Ammonium BAES | 14.0 | 14.00 | 14.00 | 9.00 | 9.00 |
| Cocamidopropylbetaine | 2.70 | 2.70 | 2.70 | 1.70 | 1.70 |
| Polyquaternium-10[6] | 0. | 0.15 | 0.15 | 0.05 | 0.02 |
| Cocamide MEA | 0.80 | 0.80 | 0 | 0.80 | 0.80 |
| Cetyl Alcohol | 0 | 0.42 | 0 | 0 | 0 |
| SUDS9 | 0.2 | 0.36 | 0.58 | 0.37 | 1.25 |
| Stearyl Alcohol | 0 | 0.18 | 0 | 0 | 0 |
| Ethylene Glycol Distearate | 0 | 0 | 0 | 1.50 | 1.50 |
| Carbopol 981[2] | 0.50 | 0.50 | 0.50 | 0 | 0 |
| EP Silicone[1] | 3.0 | 2.5 | 3.0 | 2.0 | 3.0 |
| Perfume Solution | 0.70 | 0.70 | 0.70 | 0.70 | 0.70 |
| DMDM Hydantoin | 0.37 | 0.37 | 0.37 | 0.37 | 0.37 |
| Color Solution (ppm) | 64 | 64 | 64 | 64 | 64 |
| Water and Minors | q.s. to 100% | | | | |

[1]EP Silicone is an experimental emulsion polymerized polydimethyl siloxane of about 97,000 csk with particle size of approximately 300 nm made via linear feedstock available from Dow Corning (2-1520; 13556-34).
[2]Carbopol 981 is a crosslinked polyacrylate available from B.F. Goodrich.
[3]Polyquaternium-10 is JR30M, a cationic cellulose derived polymer available from Amerchol.
[4]EP Silicone is an experimental emulsion polymerized polydimethyl siloxane of about 335,000 csk with particle size of approximately 500 nm made via linear feedstock available from Dow Corning (2-1520; PB106004).
[5]Jaguar C17 is a cationic polymer available from Rhone-Poulenc
[6]Polyquaternium-10 is JR400, a cationic cellulose derived polymer available from Amerchol.

Example 30

A Shampoo Having the Following Formula is Prepared

| Component | % weight |
|---|---|
| | AA |
| BAS | 17 |
| Zinc Pyridinethione* | 2.0 |
| Coconut Monoethanolamide | 3.0 |
| Ethylene Glycol Distereate | 5.0 |
| Sodium Citrate | 0.5 |
| SUDS7 | 0.3 |
| Citric Acid | 0.2 |
| Color solution | 0.1 |
| Perfume | 0.5 |
| Water | q.s. to 100.00% |
| | BB |
| Triethanolamine alkyl sulfate | 10% |
| BAS | 9 |
| Zinc Pyridinethione* | 2.0 |
| Coconut Monoethanolamide | 2.0 |
| SUDS1 | 0.33 |
| Triethanolamine | 3.0 |
| Magnesium/Aluminium Silicate | 0.5 |
| Hydroxy Methyl Cellulose | 0.6 |
| Color solution | 0.1 |
| Perfume | 0.3 |
| Water | q.s. to 100.00% |
| | CC |
| Sodium Alkyl Glyceryl Sulfonate | 5% |
| BAS | 15 |
| Zinc Pyridinethione* | 2.0 |
| SUDS2 | 0.2 |
| Sodium Chloride | 5.0 |
| Sodium N-Lauryl Sarcosinate | 12.0 |
| N-Cocoyl Sarcosine Acid | 1.0 |
| Lauric Diethanolamide | 2.0 |
| Color solution | 0.12 |
| Perfume | 0.5 |
| Water | q.s. to 100.00% |

*The Zinc pyridinethione salt crystals prepared according to the method described in U.S. Pat. No. 4,379,753 to Bolich.

Example 31

The compositions illustrated in Example 31 (DD to TT), illustrate specific embodiments of the shampoo compositions of the present invention, but are not intended to be limiting thereof. Other modifications can be undertaken by the skilled artisan without departing from the spirit and scope of this invention. These exemplified embodiments of the shampoo compositions of the present invention provide excellent cleansing of hair and dandruff control.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

| Component | DD | EE | FF | GG | HH |
|---|---|---|---|---|---|
| Ammonium Laureth Sulfate | 15.00 | 15.00 | 15.00 | 15.00 | 7.50 |
| BAS | 5.00 | 5.00 | 5.00 | 5.00 | 2.50 |
| Sodium Lauroyl Sarcosinate | 1.50 | 1.50 | 1.50 | 1.50 | 0.75 |
| Ethylene Glycol Distearate | 1.50 | 1.50 | 1.50 | 1.50 | 1.50 |
| SUDS3 | 0.2 | 0.55 | 0.75 | 0.8 | 1.25 |
| Zinc Pyrithione | 1.00 | 1.00 | 1.00 | — | 1.00 |
| Selenium Disulfide | — | — | — | 1.00 | — |
| Jaguar C17S | 0.10 | 0.05 | 0.50 | 0.10 | 0.10 |
| Fragrance | q.s. | q.s. | q.s. | q.s. | q.s. |
| Color | q.s. | q.s. | q.s. | q.s. | q.s. |
| pH adjustment (Mono/Di sodium Phosphate) | q.s. | q.s. | q.s. | q.s. | q.s. |
| viscosity adjustment (Sodium Chloride, | q.s. | q.s. | q.s. | q.s. | q.s. |
| preservative (DMDM Hydantoin); Water | q.s. | q.s. | q.s. | q.s. | q.s. |

| Component | JJ | KK | LL | MM | NN |
|---|---|---|---|---|---|
| BAES | 7.50 | 15.00 | 15.00 | 10.00 | 10.00 |
| BAS | 2.50 | 5.00 | 5.00 | 2.50 | 2.50 |
| Cocamidopropyl Betaine | — | — | — | 2.50 | 2.50 |
| Sodium Lauroyl Sarcosinate | 0.75 | — | — | — | — |
| Ethylene Glycol Distearate | 1.50 | 1.50 | 1.50 | 1.50 | 1.50 |
| SUDS6 | 0.1 | 0.85 | 0.15 | 0.2 | 0.3 |
| Ketoconazole | 1.00 | 1.00 | 1.00 | 1.00 | 1.00 |
| Jaguar C13S | — | 0.10 | — | 0.10 | — |
| Jaguar C17S | 0.05 | — | 0.10 | — | 0.10 |
| Fragrance | q.s. | q.s. | q.s. | q.s. | q.s. |
| Color | q.s. | q.s. | q.s. | q.s. | q.s. |
| pH adjustment (Mono/Di sodium Phosphate) | q.s. | q.s. | q.s. | q.s. | q.s. |
| Sodium Sulfate, PEG-600, Ammonium Xylene Sulfonate) | q.s. | q.s. | q.s. | q.s. | q.s. |
| preservative (DMDM Hydantoin) Water | q.s. | q.s. | q.s. | q.s. | q.s. |

| Component | OO | PP | QQ | RR | SS | TT |
|---|---|---|---|---|---|---|
| Ammonium Laureth Sulfate | 0 | 15.00 | 0 | 15.00 | 15.00 | 0 |
| BAS | 5.00 | 5.00 | 5.00 | 5.00 | 5.00 | 5.00 |
| BAES | 15.00 | 0 | 15.00 | 0 | 0 | 15.00 |
| Cocamidopropyl Betaine | 2.00 | — | — | — | — | — |
| Sodium Lauroyl Sarcosinate | — | 1.50 | 1.50 | — | — | — |
| Sodium Cocoyl Glutamate | — | — | — | — | — | 1.50 |
| SUDS5 | 0.2 | 0.9 | 0.1 | 0.2 | 0.2 | 1.5 |
| Ethylene Glycol Distearate | 1.50 | 1.50 | 1.50 | 1.50 | 1.50 | 1.50 |
| Stearyl Alcohol | — | — | — | — | — | — |
| Zinc Pyrithione | 1.00 | 0.30 | 0.30 | 0.30 | 0.30 | 1.00 |
| Jaguar C13S | 0.20 | — | — | 0.10 | 0.05 | — |
| Jaguar C17S | — | 0.10 | 0.05 | — | — | 0.10 |
| Fragrance | q.s. | q.s. | q.s. | q.s. | q.s. | q.s. |
| Color | q.s. | q.s. | q.s. | q.s. | q.s. | q.s. |
| pH adjustment (Mono/Di sodium Phosphate) | q.s. | q.s. | q.s. | q.s. | q.s. | q.s. |
| viscosity adjustment (Sodium Chloride,) | q.s. | q.s. | q.s. | q.s. | q.s. | q.s. |
| preservative (DMDM Hydantoin) | q.s. | q.s. | q.s. | q.s. | q.s. | q.s. |
| Water | q.s. | q.s. | q.s. | q.s. | q.s. | q.s. |

In preparing each of the compositions described in Examples DD to TT, about one-third of the surfactant (added as 25 wt % solution) is added to a jacketed mix tank and heated to about 74° C. with slow agitation to form a surfactant solution. Salts (sodium chloride) and pH modifiers (disodium phosphate, monosodium phosphate) are added to the tank and allowed to disperse. Ethylene glycol distearate (EGDS) is added to the mixing vessel and allowed to melt. After the EGDS is melted and dispersed (e.g., after about 5–20 minutes), preservative and additional viscosity modifier are added to the surfactant solution. The resulting mixture is passed through a heat exchanger where it is cooled to about 35° C. and collected in a finishing tank. As a result of this cooling step, the EGDS crystallizes to form a crystalline network in the product. The remainder of the surfactant and other components are added to the finishing tank with agitation to ensure a homogeneous mixture. Cationic guar polymer is dispersed in water as a 0.5–2.5% aqueous solution before addition to the final mix. Once all components have been added, viscosity and pH modifiers are added to the mixture to adjust product viscosity and pH to the extent desired.

Each exemplified composition provides excellent hair cleansing, lathering, antimicrobial agent deposition on the scalp and dandruff control.

Example 32

| Component | A | B | C |
|---|---|---|---|
| BAES | 14.00 | 14.00 | 14.00 |
| Cocamidopropyl Betaine | — | 2.50 | 2.50 |
| Cocoamphodiacetate | 2.50 | — | — |
| Cocamide MEA | 1.00 | 1.00 | 1.00 |
| SUDS12 | 0.2 | 0.2 | 0.6 |
| Ethylene Glycol Distearate | 1.50 | 1.50 | 1.50 |
| Cetyl Alcohol | 0.42 | 0.42 | 0.42 |
| Stearyl Alcohol | 0.18 | 0.18 | 0.18 |
| Zinc Pyrithione | 1.00 | 1.00 | 1.00 |
| Jaguar C13S | 0.15 | 0.15 | — |
| Jaguar C17S | — | — | 0.15 |
| Fragrance | q.s. | q.s. | q.s. |
| Color | q.s. | q.s. | q.s. |
| pH adjustment (Mono/Di sodium Phosphate) | q.s. | q.s. | q.s. |
| viscosity adjustment (Sodium Chloride, | q.s. | q.s. | q.s. |
| preservative (DMDM Hydantoin); Water | q.s. | q.s. | q.s. |

In preparing each of the compositions described in (A to C), from 50% to 100% by weight of the detersive surfactants are added to a jacketed mix tank and heated to about 74° C. with slow agitation to form a surfactant solution. If used, pH modifiers (monosodium phosphate, disodium phosphate) are added to the tank and allowed to disperse. Ethylene glycol distearate (EGDS) and fatty alcohols (cetyl alcohol, stearyl alcohol) are then added to the mixing vessel and allowed to melt. After the EGDS is melted and dispersed (usually about 5–10 minutes), preservative (if used) is added and mixed into the surfactant solution. Additional viscosity modifier are added to the surfactant solution if necessary. The resulting mixture is passed through a heat exchanger where it is cooled to about 35° C. and collected in a finishing tank. As a result of this cooling step, the EGDS crystallizes to form a crystalline network in the product. Any remaining surfactant and other components are added to the finishing tank with agitation to ensure a homogeneous mixture. Cationic guar polymer is dispersed in water as a 0.5–2.5% aqueous solution before addition to the final mix. Once all components have been added, viscosity and pH modifiers are added to the mixture to adjust product viscosity and pH to the extent desired.

Each exemplified composition provides excellent hair cleansing, lathering, antimicrobial agent deposition on the scalp, and dandruff control.

Example 33

| Component | Weight % | | | | |
|---|---|---|---|---|---|
| | UU | VV | WW | XX | YY |
| BAS | 2.0 | 2.0 | 3.0 | 2.0 | 3.0 |
| Cocamidopropyl Betaine FB | 6.0 | 6.0 | 9.0 | 6.0 | 9.0 |
| Alkyl Glyceryl Sulfonate | 10.0 | 10.0 | 6.0 | 10.0 | 6.0 |
| Mixture A | 3.0 | 6.0 | — | — | — |
| Mixture B | — | — | 3.0 | — | 6.0 |
| Mixture C | — | — | — | 3.0 | — |
| SUDS3 | 0.2 | 0.2 | 0.3 | 0.9 | 0.5 |
| Dihydrogenated Tallowamidoethyl Hydroxyethylmonium Methosulfate (1) | 0.25 | 0.50 | — | 0.25 | — |
| Ditallowamidoethyl Hydroxypropylmonium Methosulfate (2) | — | — | .25 | — | 0.25 |
| Polyquaternium-16 (Luviquat 905) | — | — | — | 0.25 | — |
| Monosodium Phosphate | 0.1 | 0.1 | 0.1 | 0.1 | 0.1 |
| Disodium Phosphate | 0.2 | 0.2 | 0.2 | 0.2 | 0.2 |
| Glycol Distearate | 2.0 | 2.0 | 2.0 | 2.0 | 2.0 |
| Cocomonoethanol amide | 0.6 | 0.6 | 0.6 | 0.6 | 0.6 |
| Fragrance | 1.0 | 1.0 | 1.0 | 1.0 | 1.0 |
| Cetyl Alcohol | 0.42 | 0.42 | 0.42 | 0.42 | 0.60 |
| Stearyl Alcohol | 0.18 | 0.18 | 0.18 | 0.18 | — |
| PEG-150 Pentaerythrityl Tetrastearate | 0.1 | 0.1 | 0.1 | 0.1 | 0.1 |
| Polyquaternium 10 (JR30M) | 0.3 | — | — | 0.1 | — |
| Polyquaternium 10 (JR400) | — | 0.3 | — | — | — |
| Polyquaternium 10 (JR125) | — | — | 0.3 | — | 0.1 |
| Dimethicone | — | 0.3 | 0.3 | — | — |
| DMDM Hydantoin | 0.2 | 0.2 | 0.2 | 0.2 | 0.2 |
| Water | qs 100 | qs 100 | qs 100 | qs 100 | qs 100 |

(1) Available under the tradename Varisoft 110 from Sherex Chemical Co. (Dublin, Ohio, USA)
(2) Available under the tradename Varisoft 238 from Sherex Chemical Co. (Dublin, Ohio, USA)

-continued

| Component | Weight % | | | | |
|---|---|---|---|---|---|
| | ZZ | AAA | BBB | CCC | DDD |
| BAES | 4.0 | 5.0 | 6.0 | 3.0 | 4.0 |
| SUDS1 | 0.2 | 0.2 | 0.25 | 1.0 | 2.5 |
| BAS | 1.0 | 1.0 | 1.0 | 1.0 | 1.0 |
| Ammonium Laureth Sulfate | 5.5 | 4.5 | 3.5 | 3.5 | 4.5 |
| Sodium Lauroampho-acetate | 7.5 | 7.5 | 7.5 | 8.5 | 7.5 |
| Mixture A | 4.0 | 6.0 | — | — | 4.0 |
| Mixture B | — | — | 4.0 | — | — |
| Mixture C | — | — | — | 4.0 | — |
| Dihydrogenated Tallowamidoethyl Hydroxyethylmonium Methosulfate (1) | 1.0 | — | — | — | — |
| Ditallowamidoethyl Hydroxypropylmonium Methosulfate (2) | — | 0.75 | — | — | — |
| Ditallow Dimethyl Ammonium Chloride (3) | — | — | 1.0 | — | 1.0 |
| Ditallowamidoethyl Hydroxyethylmonium Methosulfate (4) | — | — | — | 0.75 | — |
| Polyquaternium-16 (Luviquat 905) | — | — | — | 0.25 | — |
| Monosodium Phosphate | 0.1 | 0.1 | 0.1 | 0.1 | 0.1 |
| Disodium Phosphate | 0.2 | 0.2 | 0.2 | 0.2 | 0.2 |
| Glycol Distearate | 2.0 | 2.0 | 2.0 | 2.0 | 2.0 |
| Cocomonoethanol amide | 0.6 | 0.6 | 0.6 | 0.6 | 0.6 |
| Fragrance | 1.0 | 0.8 | 1.0 | 1.0 | 1.0 |
| Cetyl Alcohol | 0.42 | 0.42 | 0.42 | 0.42 | 0.42 |
| Stearyl Alcohol | 0.18 | 0.18 | 0.18 | 0.18 | 0.18 |
| PEG-150 Pentaerythrityl Tetrastearate | 0.08 | 0.1 | 0.1 | 0.1 | 0.1 |
| Polyquaternium 10 (JR30M) | 0.3 | — | — | 0.1 | 0.3 |
| Polyquaternium 10 (JR400) | — | 0.3 | — | — | — |
| Polyquaternium 10 (JR125) | — | — | 0.3 | — | — |
| Dimethicone | — | 0.5 | 0.3 | — | — |
| DMDM Hydantoin | 0.2 | 0.2 | 0.2 | 0.2 | 0.2 |
| Water | qs 100 | qs 100 | qs 100 | qs 100 | qs 100 |

(1) Available under the tradename Varisoft 110 from Sherex Chemical Co. (Dublin, Ohio, USA)
(2) Available under the tradename Varisoft 238 from Sherex Chemical Co. (Dublin, Ohio, USA)
(3) Available under the tradename Adogen 442-110P from Witco (Dublin, Ohio, USA)
(4) Available under the tradename Varisoft 222 from Sherex Chemical Co. (Dublin, Ohio, USA)

| Component | Weight % | | | | |
|---|---|---|---|---|---|
| | EEE | FFF | GGG | HHH | III |
| BAES | 2.0 | 3.0 | 5.0 | 2.0 | 3.0 |
| BAS | — | 1.0 | — | 1.0 | 1.0 |
| Ammonium Laureth Sulfate | 0 | 6.5 | 4.0 | 7.0 | 6.0 |
| Cocamidopropyl Betaine FB | 6.0 | — | 4.7 | — | — |
| Sodium Lauroampho-acetate | — | 7.5 | — | 7.5 | 7.5 |
| SUDS10 | 0.2 | 0.2 | 5.0 | 0.3 | 1.2 |
| Alkyl Glyceryl Sulfonate | 10.0 | — | — | — | — |
| Mixture A | — | — | — | 4.0 | — |
| Mixture C | — | — | — | — | 4.0 |
| Mixture D | 6.0 | 4.0 | 8.0 | — | — |
| Dihydrogenated Tallowamidoethyl Hydroxyethylmonium Methosulfate (1) | 0.25 | — | — | 0.5 | — |
| Ditallow Dimethyl Ammonium Chloride (3) | — | 1.0 | — | — | — |
| Di(partially hardened

| | | | | | |
|---|---|---|---|---|---|
| soyoylethyl) Hydroxyethylmonium Methosulfate (5) | — | — | 0.75 | — | 1.0 |
| Polyquaternium-16 (Luviquat 905) | — | — | — | 0.25 | — |
| Monosodium Phosphate | 0.1 | 0.1 | 0.1 | 0.1 | 0.1 |
| Disodium Phosphate | 0.2 | 0.2 | 0.2 | 0.2 | 0.2 |
| Glycol Distearate | 2.0 | 2.0 | 2.0 | 2.0 | 2.0 |
| Cocomonoethanol amide | 0.6 | 0.6 | 0.6 | 0.6 | 0.6 |
| Fragrance | 1.0 | 1.0 | 1.0 | 1.0 | 1.0 |
| Cetyl Alcohol | 0.42 | 0.42 | 0.42 | 0.42 | 0.42 |
| Stearyl Alcohol | 0.18 | 0.18 | 0.18 | 0.18 | 0.18 |
| PEG-150 Pentaerythrityl Tetrastearate | 0.10 | 0.08 | 1.0 | 0.10 | 0.08 |
| Polyquaternium 10 (JR30M) | — | — | 0.3 | — | — |
| Polyquaternium 10 (JR400) | — | 0.3 | — | — | — |
| Polyquaternium 10 (JR125) | 0.3 | — | — | — | — |
| Guar Hydroxypropyltri-monium Chloride | — | — | — | 0.25 | 0.5 |
| Dimethicone | — | 0.5 | — | — | — |
| DMDM Hydantoin | 0.2 | 0.2 | 0.2 | 0.2 | 0.2 |
| Water | qs 100 | qs 100 | qs 100 | qs 100 | qs 100 |

(1) Available under the tradename Varisoft 110 from Sherex Chemical Co. (Dublin, Ohio, USA)
(3) Available under the tradename Adogen 442-110P from Witco Corporation (Dublin, Ohio, USA)
(5) Available under the tradename Armocare EQ-S from Akzo-Nobel Chemicals Inc. (Chicago, Illinois, USA)

| Mixture A. | w/w ratio |
|---|---|
| Styling Polymer: t-butyl acrylate/2-ethylhexyl methacrylate (90/10 w/w) | 40 |
| Volatile Solvent: isododecane | 60 |

| Mixture B. | w/w ratio |
|---|---|
| Styling Polymer: t-butyl acrylate/2-ethylhexyl methacrylate (90/10 w/w) | 50 |
| Volatile Solvent: isododecane | 50 |

| Mixture C. | w/w ratio |
|---|---|
| Styling Polymer: t-butyl acrylate/2-ethylhexyl methacrylate/PDMS macromer (81/910 w/w) | 40 |
| Volatile Solvent: isododecane | 60 |

| Mixture D. | w/w ratio |
|---|---|
| Styling Polymer: vinyl pyrrolidone/vinyl acetate (5/95 w/w) | 40 |
| Volatile Solvent: diethyl succinate | 60 |

Example 34

The compositions of the present invention, in general, can be made by mixing together at elevated temperature, e.g., about 72° C. water and surfactants along with any solids (e.g., amphiphiles) that need to be melted, to speed mixing into the personal cleansing composition. Additional ingredients including the electrolytes can be added either to this hot premix or after cooling the premix. The nonionic or anionic polymers can be added as a water solution after cooling the premix. The ingredients are mixed thoroughly at the elevated temperature and then pumped through a high shear mill and then through a heat exchanger to cool them to ambient temperature. The silicone may be emulsified at room temperature in concentrated surfactant and then added to the cooled product. Alternately, for example, the silicone conditioning agent can be mixed with anionic surfactant and fatty alcohol, such as cetyl and stearyl alcohols, at elevated temperature, to form a premix containing dispersed silicone. The premix can then be added to and mixed with the remaining materials of the personal cleansing composition, pumped through a high shear mill, and cooled.

The personal cleansing compositions illustrated in Example XXII (JJJ to QQQ) illustrate specific embodiments of the personal cleansing compositions of the present invention, but are not intended to be limiting thereof. Other modifications can be undertaken by the skilled artisan without departing from the spirit and scope of this invention. These exemplified embodiments of the personal cleansing compositions of the present invention provide cleansing of hair and/or skin and improved conditioning.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

| Ingredients | JJJ | KKK | LLL | MMM | NNN |
|---|---|---|---|---|---|
| BAES | 5.00 | — | — | — | — |
| BAS | 5.00 | 7.50 | 7.50 | 7.50 | 7.50 |
| Sodium alkyl glycerol sulfonate | 2.50 | 2.50 | 2.50 | 2.50 | 2.50 |
| Cocoamidopropyl Betaine | — | — | — | — | — |
| SUDS7 | 0.2 | 0.2 | 0.6 | 0.5 | 0.25 |
| Glycol Distearate | 2.00 | 1.50 | 2.00 | 2.00 | 2.00 |
| Cocomonoethanol amide | 0.60 | 0.85 | 0.85 | 0.85 | 0.85 |
| Cetyl Alcohol | 0.42 | 0.42 | 0.42 | 0.42 | 0.42 |
| Stearyl Alcohol | 0.18 | 0.18 | 0.18 | 0.18 | 0.18 |
| EDTA (ethylenediamine tetra acetic acid) | 0.10 | 0.10 | 0.10 | 0.10 | 0.10 |
| Monosodium phosphate | 0.10 | 0.10 | 0.10 | 0.10 | 0.10 |
| Disodium phosphate | 0.20 | 0.20 | 0.20 | 0.20 | 0.20 |
| Sodium Benzoate | 0.25 | 0.25 | 0.25 | 0.25 | 0.25 |
| Hydroxyethylcellulose[1] | 0.10 | 0.25 | — | — | — |
| Hydroxypropyl Guar[2] | — | — | 0.25 | — | — |
| Hydroxyethylethylcellulose[3] | — | — | — | 0.25 | — |
| Polystyrene Sulfonate | — | — | — | — | 0.25 |
| Tricetyl methylammonium chloride | 0.58 | — | — | — | — |
| Perfume | 0.60 | 0.60 | 0.60 | 0.60 | 0.60 |
| Dimethicone | 1.00 | 1.50 | 1.50 | 1.50 | 1.50 |
| Glydant | 0.20 | 0.20 | 0.20 | 0.20 | 0.20 |
| NaCl | 0.20 | 0.30 | 0.30 | 1. | 0.30 |
| Water and minors | q.s. to 100% | | | | |

| Ingredients | OOO | PPP | QQQ |
|---|---|---|---|
| BAES | — | 9.00 | 8.00 |
| BAS | 6.00 | — | — |
| Sodium alkyl glycerol sulfonate | 1.00 | 2.50 | — |
| SUDS8 | 0.2 | 0.2 | 0.2 |
| Cocoamidopropyl Betaine | — | 2.50 | — |
| Glycol Distearate | 1.50 | 1.50 | 2.00 |
| Cocomonoethanol amide | 0.85 | 0.85 | — |
| Cetyl Alcohol | 0.42 | 0.42 | 0.40 |
| Stearyl Alcohol | 0.18 | 0.18 | 0.18 |
| EDTA (ethylenediamine tetra acetic acid) | 0.10 | 0.10 | 0.10 |
| Monosodium phosphate | 0.10 | 0.10 | 0.10 |
| Disodium phosphate | 0.20 | 0.20 | 0.20 |
| Sodium Benzoate | 0.25 | 0.25 | 0.25 |
| Hydroxyethylcellulose[1] | 0.25 | 0.25 | 0.25 |
| Hydroxypropyl Guar[2] | — | — | — |
| Hydroxyethylethylcellulose[3] | — | — | — |
| Polystyrene Sulfonate | — | — | — |
| Tricetyl methylammonium chloride | — | — | — |
| Perfume | 0.60 | 0.60 | 0.60 |
| Dimethicone | 1.50 | 1.50 | — |
| Glydant | 0.20 | 0.20 | 0.20 |
| Sodium Lauroamphoacetate | — | — | 3.60 |
| Polyquaternium-10 | — | — | 0.20 |
| NaCl | 0.30 | 0.30 | — |
| Water and minors | q.s. to 100% | | |

[1]Natrosol 250 HHR from Aqualon
[2]Jaguar HP 60 from Rhone-Poulene
[3]Bermocoll E411 FQ from Akzo Nobel The following are non-limiting examples of liquid detergent compositions comprising the polymeric suds extenders according to the present invention.

Example 35

TABLE I

| Ingredients | weight % | | |
|---|---|---|---|
| | A | B | C |
| $C_{12}$–$C_{15}$ Alkyl sulphate | — | 28.0 | 25.0 |
| $C_{12}$–$C_{13}$ Alkyl ($E_{0.6-3}$) sulfate | 30 | — | — |
| $C_{12}$ Amine oxide | 5.0 | 3.0 | 7.0 |
| $C_{12}$–$C_{14}$ Betaine | 3.0 | — | 1.0 |
| $C_{12}$–$C_{14}$ Polyhydroxy fatty acid amide | — | 1.5 | — |
| $C_{10}$ Alcohol Ethoxylate $E_9$[1] | 2.0 | — | 4.0 |
| Diamine[2] | 1.0 | — | 7.0 |
| $Mg^{2+}$ (as $MgCl_2$) | 0.25 | — | — |
| Citrate (cit2K3) | 0.25 | — | — |
| Polymeric suds booster[3] | 1.25 | 2.6 | 0.9 |
| Minors and water[4] | balance | balance | balance |
| pH of a 10% aqueous solution | 9 | 10 | 10 |

[1]$E_9$ Ethoxylated Alcohols as sold by the Shell Oil Co.
[2]1,3-diaminopentane sold as Dytek EP.
[3]Polypeptide comprising Lys, Ala, Glu, Tyr (5:6:2:1) having a molecular weight of approximately 52,000 daltons.
[4]Includes perfumes, dyes, ethanol, etc.

Example 36

TABLE II

| Ingredients | weight % | | |
|---|---|---|---|
| | A | B | C |
| $C_{12}$–$C_{13}$ Alkyl ($E_{0.6-3}$) sulfate | — | 15.0 | 10.0 |
| Paraffin sulfonate | 20.0 | — | — |
| Na $C_{12}$–$C_{13}$ linear alkylbenzene sulfonate | 5.0 | 15.0 | 12.0 |
| $C_{12}$–$C_{14}$ Betaine | 3.0 | 1.0 | — |
| $C_{12}$–$C_{14}$ Polyhydroxy fatty acid amide | 3.0 | — | 1.0 |
| $C_{10}$ Alcohol Ethoxylate $E_9$[1] | — | — | 20.0 |
| Diamine[2] | 1.0 | — | 7.0 |
| DTPA[3] | — | 0.2 | — |
| $Mg^{2+}$ (as $MgCl_2$) | 1.0 | — | — |
| $Ca^{2+}$ (as $Ca(citrate)_2$) | — | 0.5 | — |
| Protease[4] | 0.01 | — | 0.05 |
| Amylase[5] | — | 0.05 | 0.05 |
| Hydrotrope[6] | 2.0 | 1.5 | 3.0 |
| Polymeric suds booster[7] | 0.5 | 3.0 | 0.5 |
| Minors and water[8] | balance | balance | balance |
| pH of a 10% aqueous solution | 9.3 | 8.5 | 11 |

[1]$E_9$ Ethoxylated Alcohols as sold by the Shell Oil Co.
[2]1,3-bis(methylamino)cyclohexane.
[3]Diethylenetriaminepentaacetate.
[4]Suitable protease enzymes include Savinase ®; Maxatase ®; Maxacal ®; Maxapem ®; subtilisin BPN and BPN'; Protease B; Protease A; Protease D; Primase ®; Durazym ®; Opticlean ®; and Optimase ®; and Alcalase ®.
[5]Suitable amylase enzymes include Termamyl ®, Fungamyl ®; Duramyl ®; BAN ®, and the amylases as described in W095/26397 and in co-pending application by Novo Nordisk PCT/DK/96/00056.
[6]Suitable hydrotropes include sodium, potassium, ammonium or water-soluble substituted ammonium salts of toluene sulfonic acid, naphthalene sulfonic acid, cumene sulfonic acid, xylene sulfonic acid.
[7]Poly(DMAM-co-AA) (2:1) Copolymer of Example 3
[8]Includes perfumes, dyes, ethanol, etc.

Example 37

TABLE III

| Ingredients | weight % | | | |
|---|---|---|---|---|
| | A | B | C | D |
| $C_{12}$–$C_{15}$ Alkyl ($E_1$) sulfate | — | 30.0 | — | — |
| $C_{12}$–$C_{15}$ Alkyl ($E_{1.4}$) sulfate | 30.0 | — | 27.0 | — |
| $C_{12}$–$C_{15}$ Alkyl ($E_{2.2}$) sulfate | — | — | — | 15 |
| $C_{12}$ Amine oxide | 5.0 | 5.0 | 5.0 | 3.0 |
| $C_{12}$–$C_{14}$ Betaine | 3.0 | 3.0 | — | — |
| $C_{10}$ Alcohol Ethoxylate $E_9$[1] | 2.0 | 2.0 | 2.0 | 2.0 |
| Diamine[2] | 1.0 | 2.0 | 4.0 | 2.0 |
| $Mg^{2+}$ (as $MgCl_2$) | 0.25 | 0.25 | — | — |
| $Ca^{2+}$ (as $Ca(citrate)_2$) | — | 0.4 | — | — |
| Polymeric suds booster[3] | 0.5 | 1.0 | 0.75 | 5.0 |
| Minors and water[4] | balance | balance | balance | balance |
| pH of a 10% aqueous solution | 7.4 | 7.6 | 7.4 | 7.8 |

[1]$E_9$ Ethoxylated Alcohols as sold by the Shell Oil Co.
[2]1,3-diaminopentane sold as Dytek EP.
[3]LX1279 available from Baker Petrolite.
[4]Includes perfumes, dyes, ethanol, etc.

Example 38

TABLE IV

| Ingredients | weight % | | |
|---|---|---|---|
| | A | B | C |
| $C_{12}$–$C_{13}$ Alkyl ($E_{0.6-3}$) sulfate | — | 15.0 | 10.0 |
| Paraffin sulfonate | 20.0 | — | — |
| Na $C_{12}$–$C_{13}$ linear alkylbenzene sulfonate | 5.0 | 15.0 | 12.0 |
| $C_{12}$–$C_{14}$ Betaine | 3.0 | 1.0 | — |
| $C_{12}$–$C_{14}$ Polyhydroxy fatty acid amide | 3.0 | — | 1.0 |
| $C_{10}$ Alcohol Ethoxylate $E_9$[1] | — | — | 20.0 |
| Diamine[2] | 1.0 | — | 7.0 |
| $Mg^{2+}$ (as $MgCl_2$) | 1.0 | — | — |
| $Ca^{2+}$ (as $Ca(citrate)_2$) | — | 0.5 | — |
| Protease[3] | 0.1 | — | — |
| Amylase[4] | — | 0.02 | — |
| Lipase[5] | — | — | 0.025 |
| DTPA[6] | — | 0.3 | — |
| Citrate (cit2K3) | 0.65 | — | — |
| Polymeric suds booster[7] | 1.5 | 2.2 | 3.0 |
| Minors and water[8] | balance | balance | balance |
| pH of a 10% aqueous solution | 9.3 | 8.5 | 11 |

[1]$E_9$ Ethoxylated Alcohols as sold by the Shell Oil Co.
[2]1,3-bis(methylamino)cyclohexane.
[3]Suitable protease enzymes include Savinase ®; Maxatase ®; Maxacal ®; Maxapem 15 ®; subtilisin BPN and BPN'; Protease B; Protease A; Protease D; Primase ®; Durazym ®; Opticlean ®; and Optimase ®; and Alcalase ®.
[4]Suitable amylase enzymes include Termamyl ®, Fungamyl ®; Duramyl ®; BAN ®, and the amylases as described in W095/26397 and in co-pending application by Novo Nordisk PCT/DK/96/00056.
[5]Suitable lipase enzymes include Amano-P; M1 Lipase ®; Lipomax ®; Lipolase ®; D96L - lipolytic enzyme variant of the native lipase derived from *Humicola lanuginosa* as described in U.S. patent application Ser. No. 08/341,826; and the *Humicola lanuginosa* strain DSM 4106
[6]Diethylenetriaminepentaacetate.
[7]Lysozyme.
[8]Includes perfumes, dyes, ethanol, etc.

Example 39

TABLE V

| Ingredients | weight % | | |
|---|---|---|---|
| | A | B | C |
| $C_{12}$–$C_{13}$ Alkyl ($E_{0.6-3}$) sulfate | — | 27.0 | — |
| $C_{12}$–$C_{14}$ Betaine | 2.0 | 2.0 | — |
| $C_{14}$ Amine oxide | 2.0 | 5.0 | 7.0 |
| $C_{12}$–$C_{14}$ Poloxy fatty acid amide | 2.0 | — | — |
| $C_{10}$ Alcohol Ethoxylate $E_9$[1] | 1.0 | — | 2.0 |

TABLE V-continued

| Ingredients | weight % | | |
|---|---|---|---|
| | A | B | C |
| Hydrotrope | — | — | 5.0 |
| Diamine[2] | 4.0 | 2.0 | 5.0 |
| Ca$^{2+}$ (as Ca(citrate)$_2$) | — | 0.1 | 0.1 |
| Protease[3] | — | 0.06 | 0.1 |
| Amylase[4] | 0.005 | — | 0.05 |
| Lipase[5] | — | 0.05 | — |
| DTPA[6] | — | 0.1 | 0.1 |
| Citrate (cit2K3) | 0.3 | — | — |
| Polymeric suds booster[7] | 0.5 | 0.8 | 2.5 |
| Minors and water[8] | balance | balance | balance |
| pH of a 10% aqueous solution | 10 | 9 | 9.2 |

[1]E$_9$ Ethoxylated Alcohols as sold by the Shell Oil Co.
[2]1,3-diaminopentane sold as Dytek EP.
[3]Suitable protease enzymes include Savinase ®; Maxatase ®; Maxacal ®; Maxapem 15 ®; subtilisin BPN and BPN'; Protease B; Protease A; Protease D; Primase ®; Durazym ®; Opticlean ®; and Optimase ®; and Alcalase ®.
[4]Suitable amylase enzymes include Termamyl ®, Fungamyl ®; Duramyl ®; BAN ®, and the amylases as described in WO95/26397 and in co-pending application by Novo Nordisk PCT/DK/96/00056.
[5]Suitable lipase enzymes include Amano-P; M1 Lipase ®; Lipomax ®; Lipolase ®; D96L - lipolytic enzyme variant of the native lipase derived from *Humicola lanuginosa* as described in U.S. patent application Ser. No. 08/341,826; and the *Humicola lanuginosa* strain DSM 4106
[6]Diethylenetriaminepentaacetate.
[7]Poly(DMAM) homopolymer of Example 2.
[8]Includes perfumes, dyes, ethanol, etc.

Example 40

TABLE VI

| Ingredients | weight % | | |
|---|---|---|---|
| | A | B | C |
| C$_{12}$–C$_{13}$ Alkyl (E$_{1.4}$) sulfate | 33.29 | 24.0 | — |
| C$_{12}$–C$_{13}$ Alkyl (E$_{0.6}$) sulfate | — | — | 26.26 |
| C$_{12}$–C$_{14}$ Polyhydroxy fatty acid amide | 4.2 | 3.0 | 1.37 |
| C$_{14}$ Amine oxide | 4.8 | 2.0 | 1.73 |
| C$_{11}$ Alcohol Ethoxylate E$_9$[1] | 1.0 | 4.0 | 4.56 |
| C$_{12}$–C$_{14}$ Betaine | — | 2.0 | 1.73 |
| MgCl$_2$ | 0.72 | 0.47 | 0.46 |
| Calcium citrate | 0.35 | — | — |
| Polymeric suds booster[2] | 0.5 | 1.0 | 2.0 |
| Minors and water[3] | balance | balance | balance |
| pH of a 10% aqueous solution | 7.4 | 7.8 | 7.8 |

[1]E$_9$ Ethoxylated Alcohols as sold by the Shell Oil Co.
[2]Dimethylaminoethyl methacrylate/dimethylacrylamide copolymer according to any one of Examples 1.
[3]Includes perfumes, dyes, ethanol, etc.

Example 41

| | A | B | C | D | E |
|---|---|---|---|---|---|
| AE0.6S[1] | 28.80 | 28.80 | 26.09 | 26.09 | 26.09 |
| Amine oxide[2] | 7.20 | 7.20 | 6.50 | 6.50 | 6.50 |
| Citric acid | 3.00 | — | — | — | — |
| Maleic acid | — | 2.50 | — | — | — |
| Suds boosting polymer[3] | 0.22 | 0.22 | 0.20 | 0.20 | 0.20 |
| Sodium Cumene Sulfonate | 3.30 | 3.30 | 3.50 | 3.50 | 3.50 |
| Ethanol 40B | 6.50 | 6.50 | 6.50 | 6.50 | 6.50 |
| C10E8 | — | — | 3.00 | 3.00 | 3.00 |
| C11E9[4] | 3.33 | 3.33 | — | — | — |
| Diamine[5] | 0.55 | 0.55 | 0.50 | 0.50 | 0.50 |
| Perfume | 0.31 | 0.31 | — | — | — |
| Water | BAL. | BAL. | BAL. | BAL. | BAL. |
| Viscosity (cps @ 70F) | 330 | 330 | 150 | 330 | 650 |
| pH @ 10% | 9.0 | 9.0 | 8.3 | 9.0 | 9.0 |

| | F | G | H | I | J |
|---|---|---|---|---|---|
| AE0.6S[1] | 26 | 26 | 26 | 26 | 26 |
| Amine oxide[2] | 6.5 | 6.5 | 7.5 | 7.5 | 7.5 |
| Citric acid | 3.0 | — | 2.5 | — | 3.0 |
| Maleic acid | — | 2.5 | — | 3.0 | — |
| C10E8[6] | 3 | 3 | 4.5 | 4.5 | 4.5 |
| Diamine[5] | 0.5 | 0.5 | 1.25 | 0 | 1.25 |
| Diamine[7] | 0 | 0 | 0 | 1 | 0 |
| Suds boosting polymer[3] | 0 | 0.2 | 0.5 | 0.5 | 0.5 |
| Sodium cumene sulphonate | 3.5 | 3.5 | 2 | 2 | 2 |
| Ethanol | 8 | 8 | 8 | 8 | 8 |
| pH | 9 | 9 | 9 | 8 | 10 |

[1]C12–13 alkyl ethoxy sulfonate containing an average of 0.6 ethoxy groups.
[2]C$_{12}$–C$_{14}$ Amine oxide.
[3]Polymer is (N,N-dimethylamino)ethyl methacrylate homopolymer
[4]C11 Alkyl ethoxylated surfactant containing 9 ethoxy groups.
[5]1,3 bis(methylamine)-cyclohexane.
[6]C10 Alkyl ethoxylated surfactant containing 8 ethoxy groups.
[7]1,3 pentane diamine.

Example 42

Skin feel is determined by the modified acid phosphatase, or MAP method. This method describes a rapid screening enzyme assay which predicts skin mildness of surfactant systems by measuring acid phosphatase inhibition as a result of exposure to surfactants.

Procedure

Equipment 96 well flat bottom microtiter plate,

Finnipipette (Labsystems) digital multichannel pipette (50–300 ul) with reservoir and tips, Eppendorf repeater pipette with tips (1.25 and 5 ml), gloves plate shaker plate reader(EL312 microplate by Bio Tek Instruments-Bio Kinetics Reader)

microtiter plate heating block pH meter

Gilson pipetman pipettes (10–100 ul; 100–1000 ul) with tips

Reagents purified acid phosphatase (typically, potato, type II lyophilized, from Sigma, P3752)

Disodium p-nitrophenylphosphate (typically, Sigma 104 phosphatase substrate)

citric acid (reagent grade)

sodium citrate (reagent grade)

HPLC grade water (or distilled/deionized/high quality water (HQW))

water hardness concentrate (3:1 Ca++/Mg++, ITC supply)

Sodium hydroxide (0.5N NaOH)

Predried porcine stratum corneum

Preparation of Solutions:

Prepare enzyme solution by making a 1–2 mg/ml solution (to give O.D. at 405 nm of 1.2–1.7 with a target of 1.5) of purified acid phosphatase (0.5–1.0 units of activity/mg at room temperature) in HPLC water and keep on ice. Make fresh prior to use.

Prepare citrate buffer at pH4.5 by combining 0.82 g citric acid, 2.25 g sodium citrate, and Q.S. to 100 ml with HPLC water.

Prepare substrate/buffer solution: 3.0 mM p-nitrophenylphosphatase (F.W.263) in 10 mM citrate buffer @pH 4.5 (add 8 mg PNPP in 10 ml citrate buffer.

Prepare development solution: 0.5N NaOH.

Make 7 gpg water: Add 0.6 ml of hardness concentrate to 1000 ml of HPLC water

Partitioning Followed by Extraction of Surfactants Into Stratum Corneum

Place the surfactant solution (300 g) at the desired water hardness in a 115F waterbath to get to temperature.

Cut and weigh the predried porcine stratum corneum to get approximately the same size by weight sample from the same piece of pigskin for the treatments to be tested and compared.

Place the pigskins in the appropriate solutions, making sure the pigskins stay at the bottom of beaker to insure all surface is exposed to solution, and let soak for 30 minutes at the 115 F. temperature.

After the soak, the pigskin is rinsed (or placed) in fresh room temperature 0 gpg water for 30 seconds.

After the rinse the pigskin is placed in a clean 15 ml vial and HQW (12–14 ml) is added to the vial and aluminum foil is placed on the top of vial before lid is screwed on.

The vial is placed in the 115F waterbath for 2 hours and during the 2 hours inverted every ½ hr.

After the extraction for 2 hrs the pigskin is removed and discarded and the extract is evaporated to dryness using dry $N_2$(overnight drying).

Reconstitute the dried extract with 0.4 ml HQW and place back into waterbath set at 50–55C to insure surfactant goes in solution—the solution should be clear.

Addition of Surfactants to Microtiter Wells

Place empty microtiter plate on pre-heated plate warming block (115F).

Place thermometer in plate and wait for temperature to reach @ 113F.

Add 50 ul of the heated extracted surfactant solutions (400 ul) to designated wells. Add 50 ul of 115F water (hardness in which soak was conducted) to control wells and the blanks. Generally, blanks are run as the first well in each row. (see Appendix II for template setup)

Add 25 ul of the enzyme solution to each well except blanks (the control will have enzyme, but no surfactant, and will show the highest enzyme activity) as quickly as possible (<30 sec.). Add 25 ul of the 115F water (hardness in which soak was conducted) to the blanks. Once enzyme added to first well set timer for five minutes.

Move microtiter plate to plate shaker. Shake for 30 seconds.

Return microtiter plate to plate warming block for the duration of the five minutes. After the five minutes remove from heating block.

Add 75 ul of the substrate/buffer solution to each well using the multi-channel pipette. This step activates the enzyme to liberate product, so the solution must be added as quickly and as accurately as possible (<30 sec.). Activate wells of a single row first before adding solution to wells of the next row.

After 3 minutes, quickly add 100 ul of 0.5N NaOH to each well using the multi-channel pipette. This step stops the reaction and develops the color for the spectrophotometric measurement at 405 nm using the plate reader, so this solution must also be added as quickly and as accurately as possible (<30 sec.). The color will be stable for up to 30 minutes if the plate is covered.

Obtain absorbance results using plate reader set at 405 nm.

Background Correction

Some surfactants may interfere at 405 nm and background correction is required for these materials. The correction is made by simply redoing the above 8 steps with the exception of adding the enzyme solution. This is replaced with 25 ul of water. Read wells at 405 nm and subtract background absorbance values from absorbances (average) derived from corresponding reacted wells. A background subtraction should be performed for every surfactant and product tested.

Calculation

Subtract blank absorbance value from control absorbance value to obtain the absorbance of the control wells (maximum enzyme introduced in the experiment). Subtract surfactant absorbance backgrounds from appropriate surfactant-acid phosphatase absorbances to obtain absorbance of surfactant wells.

Derive Ratio of Inhibition (or % enzyme deactivation) for each concentration as follows:

[1−(absorbance of surfactant/absorbance of control)]*100

Reporting

Re compare to a control product. An increase in % deactivation corresponds to greater product harshness outside the standard deviation of test method (+/−4%).

Effect of Including Polymeric Suds Booster in an LDL Composition

The LDL composition tested has the formula

| | |
|---|---|
| AE0.6S | 26.6 |
| Amine Oxide | 6.60 |
| C11E9/C10E8 | 3.1 |
| Diamine | 0.5 |
| Polymer | 0.22 |
| water minors | qs to 100% |

The polymer used is the polymer of Example 2 above. MAP results are in % deactivation

| Hardness, in grains per gallon | LDL with 0.22% polymer | LDL with nil-polmer |
|---|---|---|
| 2 gpg | 27B | 46 |
| 7 gpg | 37BC | 50 |

This result clearly shows the mildness benefit gained from including the suds boosting polymers of the present invention.

What is claimed is:

1. A method for manually cleaning an object comprising the step of manually washing said object in and contacting a user's hands with a washing solution comprising water and a detergent composition comprising a polymeric suds stabilizer and a diamine, wherein said diamine has a molecular weight of less than or equal to 400 g/mol; and said suds stabilizer is selected from the group consisting of:
(a) polymers comprising at least one monomeric unit of the formula:

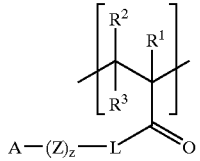

wherein each of $R^1$, $R^2$ and $R^3$ are independently selected from the group consisting of hydrogen, $C_1$ to $C_6$ alkyl, and mixtures thereof; L is selected from the group consisting of O, $NR^6$, $SR^7R^8$ and mixtures thereof, wherein $R^6$ is selected from the group consisting of hydrogen, $C_1$ to $C_8$ alkyl and mixtures thereof; each of $R^7$ and $R^8$ are independently hydrogen, O, $C_1$ to $C_8$ alkyl and mixtures thereof, or $SR^7R^8$ form a heterocyclic ring containing from 4 to 7 carbon atoms, optionally containing additional hetero atoms and optionally substituted; Z is selected from the group consisting of: —($CH_2$)—, ($CH_2$—CH=CH)—, —($CH_2$—CHOH)—, ($CH_2$—$CHNR^6$)—, —($CH_2$—$CHR^{14}$—O)— and mixtures thereof; wherein $R^{14}$ is selected from the group consisting of hydrogen, $C_1$ to $C_6$ alkyl and mixtures thereof; z is an integer selected from about 0 to about 12; A is $NR^6R^5$, wherein each of $R^4$ and $R^5$ are independently selected from the group consisting of hydrogen, $C_1$ to $C_8$ alkyl, and mixtures thereof, or $NR^4R^5$ form an heterocyclic ring containing from 4 to 7 carbon atoms, optionally containing additional hetero atoms, optionally fused to a benzene ring, and optionally substituted by $C_1$ to $C_8$ hydrocarbyl; and wherein said polymeric suds stabilizer has a molecular weight of from about 1,000 to about 2,000,000 daltons;
(b) a proteinaceous suds stabilizer, said proteinaceous suds stabilizer having an isoelectric point of from about 7.5 to about 11.5
(c) a zwitterionic polymeric suds stabilizer; and
(d) mixtured thereof;
wherein said suds stabilizer is mild, suds enhancing and suds stabilizing such that suds produced by said solution is maintained for an extended period of time by said suds stabilizer and a user's hands, after submersion in a solution containing said suds stabilizer, are not irritated.

2. The method according to claim 1 wherein said polymeric suds stabilizer comprises a molecular weight of from about 5,000 to About 1,000,000.

3. The method according to claim 1 wherein said polymeric suds stabilizer comprises polymers having at least one monomeric unit of the formula:

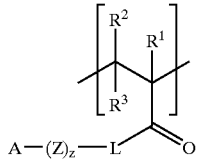

wherein each of $R^1$, $R^2$, $R^3$, L, Z, z and A are as hereinbefore defined.

4. The method according to claim 1 wherein said zwitterionic polymeric suds stabilizer has the formula:

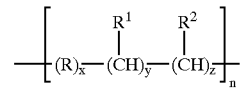

wherein R is $C_1$–$C_{12}$ linear alkylene, $C_1$–$C_{12}$ branched alkylene, and mixtures thereof; $R^1$ is a unit capable of having a negative charge at a pH of from about 4 to about 12; $R^2$ is a unit capable of having a positive charge at a pH of from about 4 to about 12; n has a value such that said zwitterionic polymers suds stabilizer has an average molecular weight of from about 1,000 to about 2,000,000 daltons; x is from 0 to 6; y is 0 or 1; and z is 0 or 1.

5. The method according to claim 1 wherein said polymeric suds stabilizer is selected from the group consisting of a homopolymer, a copolymer, a terpolymer and mixtures thereof.

6. The method according to claim 1 wherein said composition further comprises a detersive surfactant selected from the group consisting of anionic surfactants, nonionic surfactants, amphoteric surfactants, zwitterionic surfactants, cationic surfactants, and mixtures thereof.

7. The method according to claim 6 wherein said detersive surfactant is an anionic surfactant having skin irritating characteristics and is selected from the group consisting of $C_8$–$C_{18}$ alkyl benzene sulfonates, $C_8$–$C_{18}$ alkyl sulfates containing from 0 to 3 ethenoxy groups in the molecule, $C_8$–$C_{25}$ olefin sulfonates, $C_{10}$–$C_{20}$ paraffin sulfonates, $C_8$–$C_9$ alkyl phenol ethoxamer sulfates, and mixtures thereof.

8. The method according to claim 1 wherein said diamine is selected from the group consisting of dimethyl aminopropyl amine, 1,6-hexane diamine, 1,3 propane diamine, 2-methyl 1,5 pentane diamine, 1,3-pentanediamine, 1,3-diaminobutane, 1,2-bis(2-aminoethoxy)ethane, isophorone diamine, 1,3-bis(methylamine)-cyclohexane and mixtures thereof.

9. The method according to claim 1 wherein said composition further comprises an anionic surfactant, an amine oxide, an enzyme and mixtures thereof, wherein said enzyme is selected from the group consisting of amylase, protease and mixtures thereof.

10. The method according to claim 9 wherein said composition further comprises an effective amount of magnesium ions.

11. The method according to claim 1 wherein said composition is in a form selected from the group consisting of granules, tablets, liquids, liquid-gels, gels, microemulsion, thixatropic liquid, bars, pastes, powders and mixtures thereof.

12. The method according to claim 1 wherein said composition is a hand dishwashing composition.

13. The method according to claim 1 wherein said method reduces irritation to skin caused by said detergent composition.

14. The method according to claim 1 wherein said proteinaceous suds stabilizer comprises at least about 10% by weight of one or more amino acids which are protonated at a pH of less than about 11.

15. A method for manually cleaning an object comprising the steps of:
(a) washing said object with a washing solution comprising water and a detergent composition comprising:

(i) a suds stabilizer comprising units capable of having a cationic charge at a pH of from about 4 to about 12, provided that said suds stabilizer has an average cationic charge density of at least about 1 unit per 100 daltons molecular weight at a pH of from about 4 to about 12; and (ii) a diamine having a molecular weight of less than or equal to 400 g/mol; and (b) contacting said practitioner's hands with said solution while practicing said washing step, wherein suds produced by said solution are maintained by said suds stabilizer and said practitioner's hands are not irritated.

16. The method according to claim 15 wherein said polymeric suds stabilizer further comprises:
   i) units capable of having an anionic charge at a pH of from about 4 to about 12:
   ii) units capable of having an anionic charge and a cationic charge at a pH of from about 4 to about 12;
   iii) units having no charge at a pH of from about 4 to about 12; and
   iv) mixtures thereof.

17. The method according to claim 15 wherein said polymeric suds stabilizer has an average molecular weight of from about 1,000 to about 2,000,000 daltons.

18. The method according to claim 15 wherein said polymeric suds stabilizer is a polymer comprising at lest one monomeric unit of the formula:

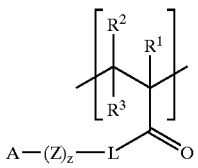

wherein wherein each of $R^1$, $R^2$ and $R^3$ are independently selected from the group consisting of hydrogen, $C_1$ to $C_6$ alkyl, and mixtures thereof; L is selected from the group consisting of O, $NR^6$, $SR^7R^8$ and mixtures thereof, wherein $R^6$ is selected from the group consisting of hydrogen, $C_1$ to $C_8$ alkyl and mixtures thereof; each of $R^7$ and $R^8$ are independently hydrogen, O, $C_1$ to $C_8$ alkyl and mixtures thereof, or $SR^7R^8$ form a heterocyclic ring containing from 4 to 7 carbon atoms, optionally containing additional hetero atoms and optionally substituted; Z is selected from the group consisting of: —$(CH_2)$—, $(CH_2$—$CH$=$CH)$—, —$(CH_2$—$CHOH)$—, $(CH_2$—$CHNR^6)$—, —$(CH_2$—$CHR^{14}$—$O)$— and mixtures thereof; wherein $R^{14}$ is selected from the group consisting of hydrogen, $C_1$ to $C_6$ alkyl and mixtures thereof; z is an integer selected from about 0 to about 12; A is $NR^4R^5$, wherein each of $R^4$ and $R^5$ are independently selected from the group consisting of hydrogen, $C_1$ to $C_8$ alkyl, and mixtures thereof, or $NR^4R^5$ form an heterocyclic ring containing from 4 to 7 carbon atoms, optionally containing additional hetero atoms, optionally fused to a benzene ring, and optionally substituted by $C_1$ to $C_8$ hydrocarbyl; and wherein said polymeric suds stabilizer has a molecular weight of from about 1,000 to about 2,000,000 daltons.

19. The method according to claim 15 wherein said polymeric suds stabilizer is a zwitterionic polymeric suds stabilizer of the formula:

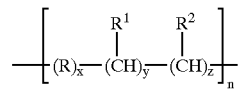

wherein R is $C_1$–$C_{12}$ linear alkylene, $C_1$–$C_{12}$ branched alkylene, and mixtures thereof; $R^1$ is a nit capable of having a negative charge at a pH of from about 4 to about 12; $R^2$ is a unit capable of having a positive charge at a pH of from about 4 to about 12; n has a value such that said zwitterionic polymers suds stabilizer has an average molecular weight of from about 1,000 to about 2,000,000 daltons; x is from 0 to 6; y is 0 or 1; and z is 0 or 1.

20. The method according to claim 15 wherein said proteinaceous suds stabilizer comprises at least about 10% by weight of one or more amino acids which are protonated at a pH of less than about 11.

21. The method according to claim 15 wherein said polymeric suds stabilizer is selected from the group consisting of a homopolymer, a copolymer, a terpolymer and mixtures thereof.

22. The method according to claim 15 wherein said composition further comprise a detersive surfactant selected from the group consisting of anionic surfactants, nonionic surfactants, amphoteric surfactants, zwitterionic surfactants, cationic surfactants, and mixtures thereof.

23. The method according to claim 22 wherein said detersive surfactant is an anionic surfactant having skin irritating characteristics and is selected from the group consisting of $C_8$–$C_{18}$ aklyl benzene sulfonates, $C_8$–$C_{18}$ alkyl sulfates containing from 0 to 3 ethenoxy groups in the molecule, $C_8$–$C_{25}$ olefin sulfonates, $C_{10}$–$C_{20}$ paraffin sulfonates, $C_8$–$C_9$ alkyl phenol ethoxamer sulfates, and mixtures thereof.

24. The method according to claim 15 wherein said diamine is selected from the group consisting of dimethyl aminopropyl amine, 1,6-hexane diamine 1,3 propane diamine, 2-methyl 1,5 pentane diamine, 1,3-pentanediamine, 1,3-diaminobutane, 1,2-bis(2-aminoethoxy)ethane, isophorone diamine, 1,3-bis (methylamine)-cyclohexane and mixtures thereof.

25. The method according to claim 15 wherein said composition further comprises an anionic surfactant, an amine oxide, an enzyme and mixtures thereof, wherein said enzyme is selected from the group consisting of amylase, protease and mixtures thereof.

26. The method according to claim 25 wherein said composition further comprises an effective amount of magnesium ions.

27. The method according to claim 15 wherein said composition is in a form selected from the group consisting of granules, tablets, liquids, liquid-gels, gels, microemulsion, thixatropic liquid, bars, pastes, powders and mixtures thereof.

28. The method according to claim 15 wherein said composition is a hand dishwashing composition.

29. The method according to claim 15 wherein said method reduces irritation to skin caused by said detergent composition.

* * * * *